(12) United States Patent
Zalevsky et al.

(10) Patent No.: US 10,398,314 B2
(45) Date of Patent: *Sep. 3, 2019

(54) METHOD AND SYSTEM FOR NON-INVASIVELY MONITORING BIOLOGICAL OR BIOCHEMICAL PARAMETERS OF INDIVIDUAL

(71) Applicants: BAR ILAN UNIVERSITY, Ramat Gan (IL); UNIVERSITAT DE VALENCIA, Valencia (ES)

(72) Inventors: Zeev Zalevsky, Rosh HaAyin (IL); Javier Garcia, Valencia (ES); Yevgeny Beiderman, Netanya (IL); Israel Margalit, Ramat Gan (IL); Nisim Nisan Ozana, Rehovot (IL); Nadav Arbel, Ramat Gan (IL); Vicente Mico, Valencia (ES); Martin Sanz Sabater, Valencia (ES); Yael Bishitz, Har Chevron (IL); Asaf Shahmoon, Petach Tikva (IL)

(73) Assignees: BAR ILAN UNIVERSITY, Ramat Gan (IL); UNIVERSITAT DE VALENCIA, Valencia (ES)

( * ) Notice: Subject to any disclaimer, the term of this patent is extended or adjusted under 35 U.S.C. 154(b) by 213 days.

This patent is subject to a terminal disclaimer.

(21) Appl. No.: 15/483,828

(22) Filed: Apr. 10, 2017

(65) Prior Publication Data
US 2017/0209047 A1 Jul. 27, 2017

Related U.S. Application Data

(63) Continuation of application No. 14/168,730, filed on Jan. 30, 2014, now Pat. No. 9,636,041, which is a
(Continued)

(51) Int. Cl.
A61B 3/16 (2006.01)
A61B 5/00 (2006.01)
(Continued)

(52) U.S. Cl.
CPC ............ *A61B 3/165* (2013.01); *A61B 3/0008* (2013.01); *A61B 3/102* (2013.01); *A61B 5/0051* (2013.01);
(Continued)

(58) Field of Classification Search
CPC ..... A61B 5/0803; A61B 5/14542; A61B 3/16; A61B 5/4875; A61B 5/01; A61B 5/0261;
(Continued)

(56) References Cited

U.S. PATENT DOCUMENTS

RE40,316 E  5/2008 Gobeli et al.
2002/0016533 A1  2/2002 Marchitto et al.
(Continued)

FOREIGN PATENT DOCUMENTS

EP  2156785 A  2/2010
FR  2756047 A1  5/1998
(Continued)

OTHER PUBLICATIONS

Anand, Arun et al., Speckle-Based Optical Sensor for Low Field Faraday Rotation Measurement, IEEE Sensors Journal, Feb. 2013, vol. 13, No. 2, 723-727.
(Continued)

*Primary Examiner* — Mark Bockelman
(74) *Attorney, Agent, or Firm* — Browdy and Neimark, PLLC

(57) ABSTRACT

A system and method monitoring conditions of a subject's body including a control unit receiving image data and data indicative of an external stimulation applied to the body during collection of the image data therefrom, a memory
(Continued)

utility, and a processor utility. The image data is indicative of a sequence of speckle patterns generated by the body according to a certain sampling time pattern. The processor utility performs processing the image data utilizing the data indicative of the applied external field(s), including determining a spatial correlation function between successive speckle patterns in the sequence, and determining a time varying spatial correlation function in the form of a time-varying function of a feature of the correlation function indicative of a change of the speckle pattern over time; selecting a parameter of the time-varying spatial correlation function, and applying a model to the parameter to determine a corresponding body condition; and generating output data indicative of the corresponding body condition.

16 Claims, 33 Drawing Sheets

Related U.S. Application Data continuation-in-part of application No. PCT/IL2013/050658, filed on Aug. 1, 2013, which is a continuation of application No. 13/564,381, filed on Aug. 1, 2012, now Pat. No. 9,668,672.

(60) Provisional application No. 61/678,131, filed on Aug. 1, 2012.

(51) Int. Cl.

| | |
|---|---|
| *A61B 5/024* | (2006.01) |
| *A61B 5/1455* | (2006.01) |
| *A61B 3/10* | (2006.01) |
| *A61B 3/00* | (2006.01) |
| *A61B 5/021* | (2006.01) |
| *A61B 5/026* | (2006.01) |
| *A61B 5/145* | (2006.01) |
| *A61B 5/02* | (2006.01) |

(52) U.S. Cl.
CPC .......... *A61B 5/0059* (2013.01); *A61B 5/0066* (2013.01); *A61B 5/0261* (2013.01); *A61B 5/02108* (2013.01); *A61B 5/02116* (2013.01); *A61B 5/02416* (2013.01); *A61B 5/1455* (2013.01); *A61B 5/14532* (2013.01); *A61B 5/7275* (2013.01); *A61B 5/02035* (2013.01); *A61B 5/14542* (2013.01); *A61B 5/4504* (2013.01)

(58) Field of Classification Search
CPC . A61B 5/02416; A61B 3/0008; A61B 5/0066; A61B 5/02028; A61B 5/7278; A61B 5/14507; A61B 3/102; A61B 5/0295; A61B 5/1455; A61B 5/14532; A61B 5/14546; A61B 3/165; A61B 5/7275; A61B 5/0059; A61B 5/02116; A61B 5/02108; A61B 5/0051; A61B 5/4504; A61B 5/02035
See application file for complete search history.

(56) References Cited

U.S. PATENT DOCUMENTS

| | | | |
|---|---|---|---|
| 2002/0049372 | A1 | 4/2002 | Diab |
| 2002/0183601 | A1 | 12/2002 | Tearney et al. |
| 2003/0209834 | A1 | 11/2003 | Hay et al. |
| 2004/0152989 | A1 | 8/2004 | Puttappa et al. |
| 2005/0049468 | A1 | 3/2005 | Carlson et al. |
| 2006/0025659 | A1 | 2/2006 | Kiguchi et al. |
| 2008/0026235 | A1 | 10/2008 | Tearney et al. |
| 2009/0209834 | A1 | 8/2009 | Fine |
| 2010/0046897 | A1 | 2/2010 | Toriya et al. |
| 2011/0013002 | A1 | 1/2011 | Thompson et al. |
| 2013/0144137 | A1 | 6/2013 | Zalevsky et al. |
| 2014/0020611 | A1 | 1/2014 | Sakamoto et al. |

FOREIGN PATENT DOCUMENTS

| | | |
|---|---|---|
| JP | 2006042955 | 2/2006 |
| JP | 2007244533 A | 9/2007 |
| JP | 2010508056 | 3/2010 |
| WO | 2000060350 A2 | 10/2000 |
| WO | 0150955 A1 | 7/2001 |
| WO | 02036015 A1 | 5/2002 |
| WO | 2008053474 | 5/2008 |
| WO | 2008053474 A2 | 5/2008 |
| WO | 2009013738 A1 | 1/2009 |
| WO | 2009151610 A2 | 12/2009 |
| WO | 2010105197 A2 | 9/2010 |
| WO | 2012101644 A2 | 8/2012 |

OTHER PUBLICATIONS

Shenhav, Asaf et al., Optical sensor for remote estimation of alcohol concentration in blood stream, Optics Communications, Oct. 23, 2012, vol. 289, 149-157—Abstract only attached.

Beiderman, Yevgeny et al., Optical Remote Continuous Sensing of Intraocular Pressure Variations, Proc. of SPIE, 2012, vol. 8209, 820908-1 to 8—Abstract only attached.

Asejczyk-Widlicka, et al., "Fluctuations in intraocular pressure and the potential effect on aberrations of the eye", Br J Ophthalmol ; 91:1054-1058 (2007).

De la Torre-Ibarra, et al. "Double-shot depth-resolved displacement field measurement using phase-contrast spectral optical coherence tomography", Opt. Express 14: 9643-9656, (2006).

T. Matsumoto et al., Measurement by holographic interferometry of the deformation of the eye accompanying changes in intraocular pressure Appl. Opt. 17:3538-3539 (1978).

Yevgeny Beiderman et al: "Remote estimation of blood pulse pressure via temporal tracking of reflected secondary speckless pattern" Journal of Biomedical Optics, 15(6):061707-0617077 (2010).

International Search Report for PCT/IL2013/050658, dated Dec. 17, 2013.

Ozana et al "Improved noncontact optical sensor for detection of glucose concentration and indication of dehydration level", Biomedical Optics Express, 5 (6) 1926-1940 (2014).

Koller "A magneto-optical tachometer based on the Faraday effect", Physics Individual Project Siemens-Westinghouse Competition, 1 (Oct. 2000).

Yu-Lung et al, "A polarimetric glucose sensor using a liquid-crystal polarization modulator driven by a sinusoidal signal", Optics Communications 259 : 40-48, (Jan. 2006).

Jang et al, "Double Lock& Amplifier Faraday Rotation Glucometer" IEEE 26th Annual northeast Bioengineering conference, Storrs, University of Connecticut, 107-108 (Apr. 2000).

Clarke "Development and optimization of an integrated Faraday modulator and compensator design for continuous polarimetric glucose monitoring" (May 2013).

International Search Report, dated Jun. 8, 2015, in corresponding application No. PCT/IL2015050100.

Supplemental European Search Report dated Jan. 11, 2018 for European patent application No. EP15743506.

Ponticorvo Adrien et al: "Laser speckle contrast imaging of blood flow in rat retinas using an endoscope" International Society for Optical Engineering, SPIE, vol. 18, No. 9, Sep. 1, 2013, p. 90501.

Youngwoon Choi et al: Scanner-Free and Wide-Field Endoscopic Imaging by Using a Single Multimode Optical Fiber, Physical Review Letters, vol. 109, No. 20, Nov. 12, 2012, pp. 2003901-1.

Ozana Nisan et al: "Demonstration of a Remote Optical Measurement Configuration That Correlates with Breathing, Heart Rate, Pulse Pressure, Blood Coagulation, and Blood Oxygenation", Proceeding of the IEEE, New York, US, vol. 103, No. 2, Feb. 1, 2015, pp. 248-262.

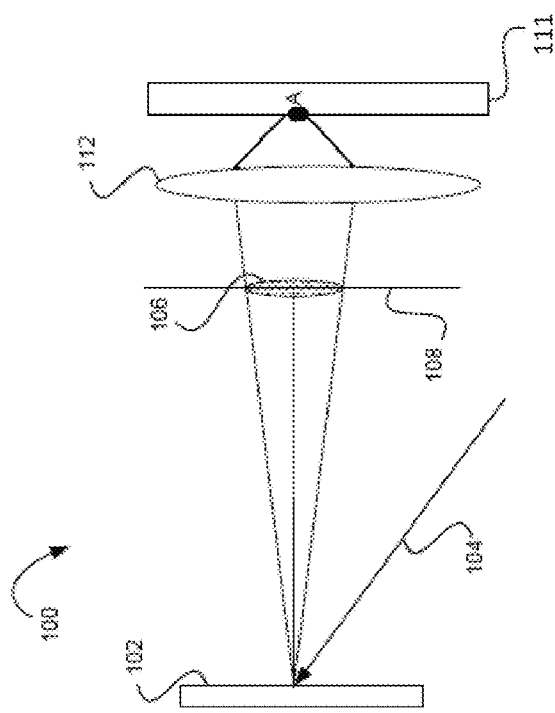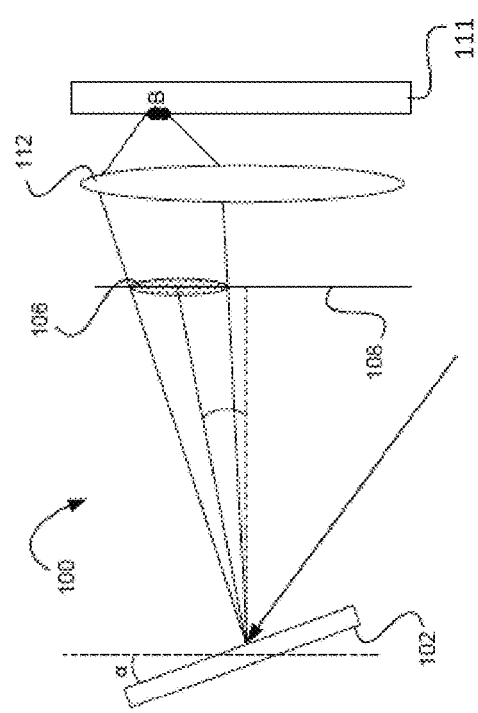

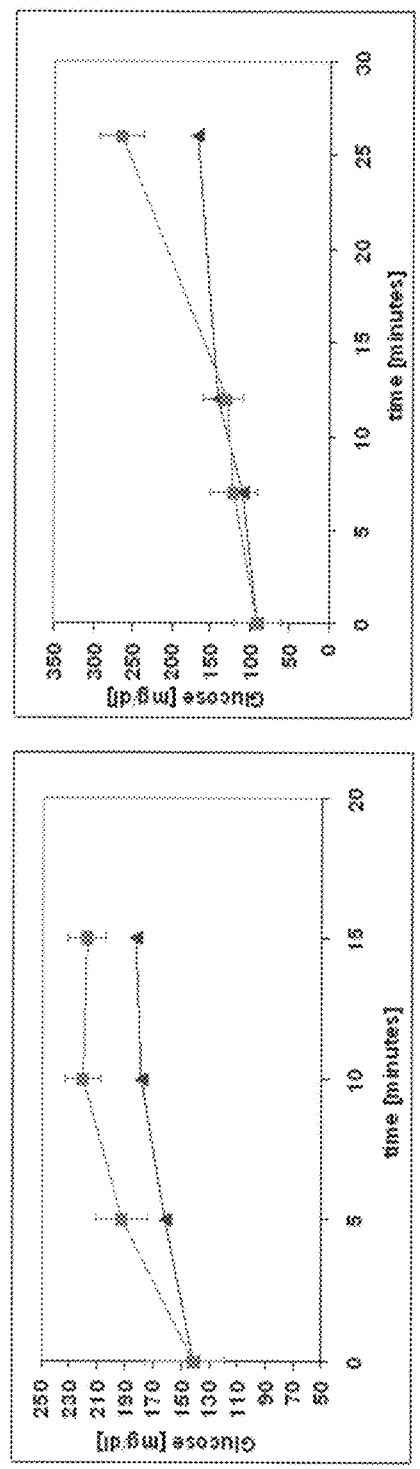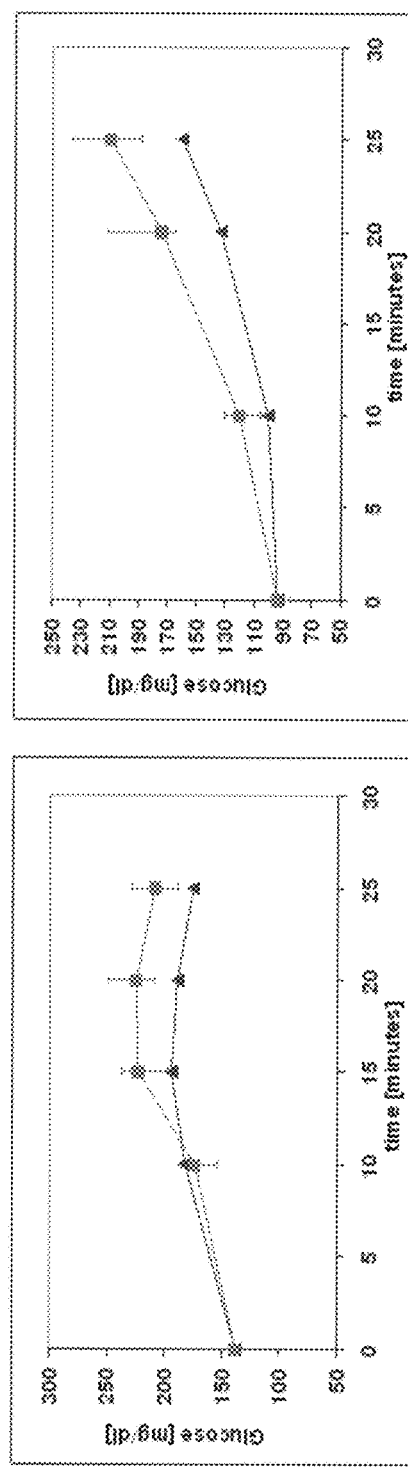
Fig. 8A  Fig. 8B  Fig. 8C  Fig. 8D

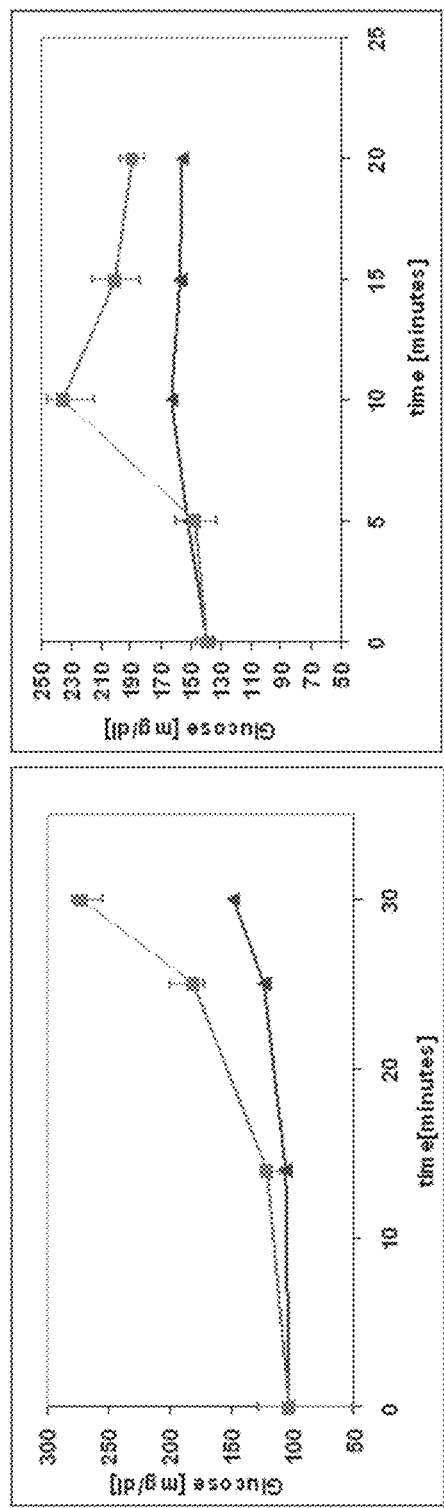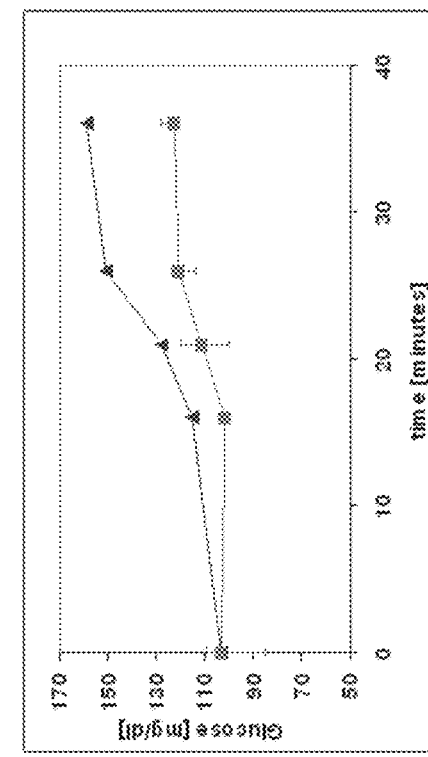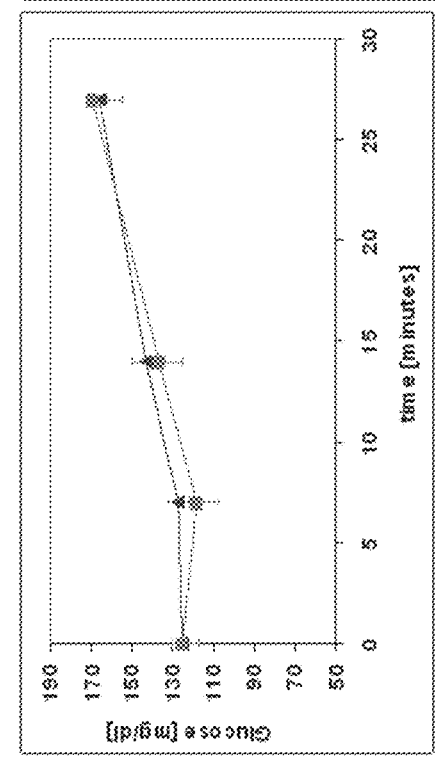
Fig. 10A  Fig. 10B  Fig. 10C  Fig. 10D

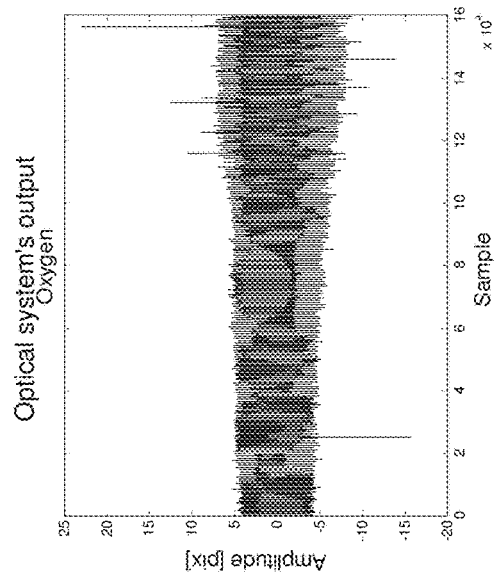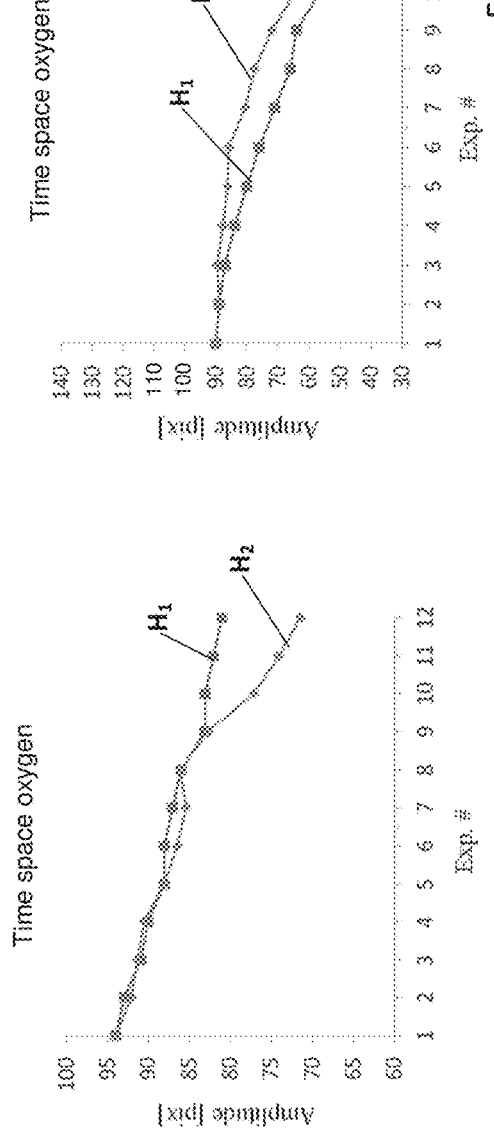
FIG. 27A
FIG. 27B
FIG. 27C

METHOD AND SYSTEM FOR NON-INVASIVELY MONITORING BIOLOGICAL OR BIOCHEMICAL PARAMETERS OF INDIVIDUAL

FIELD OF THE INVENTION

This invention relates to a method and system for non-invasively monitoring biological or biochemical parameters and conditions of an individual. The present invention is particularly useful for monitoring various parameters and conditions relating to biological fluids such as blood, e.g. glucose concentration in blood, breathing, blood oxymetry, blood coagulation, as well as for monitoring parameters related to an internal organ being inspected.

BACKGROUND

The human body contains many fluids having vital functions within the body. For example, blood flowing in the circulatory system delivers necessary substances such as nutrients and oxygen to cells, and transports metabolic waste products away from those cells. Another fluid is the aqueous humor in the eyes. The aqueous humor maintains the intraocular pressure and inflates the globe of the eye, provides nutrition (e.g. amino acids and glucose) for the avascular ocular tissues, posterior cornea, trabecular meshwork, lens, and anterior vitreous.

Some properties of these bodily fluids are known to be indicative of a condition of the person's body, and determination of such properties may be used in order to monitor a person's health. For example, the blood glucose level (also referred to as blood glucose concentration) being too high or too low can be indicative of a malfunction of the digestive system, such as diabetes mellitus. Blood oxygen level is typically monitored to identify oxygen saturation condition that enables identification of hypoxemia as well allows estimation of hemoglobin in blood. Blood alcohol level (also referred to as blood alcohol concentration) is indicative of alcohol consumption and may be used to determine detrimental effects of alcohol on the gastrointestinal, cardiovascular and central nervous systems. Blood alcohol level is also indicative of impairment in a person's judgment and his ability to perform certain actions, such as driving a vehicle. In the eye, an important property of the aqueous humor is its pressure. This property is commonly called "intraocular pressure". A high intraocular pressure may be indicative of disorders in the eye, such as glaucoma, iritis, and retinal detachment.

In the field of measuring blood-related parameters, such as glucose level and oxygen saturation, many non-invasive techniques have been devised, including impedance-based techniques and optical. For example, in glucose meters based on near infrared spectroscopy, a tissue is illuminated with light in the infrared spectrum, and the light reflected by the tissue and/or the light transmitted through the tissue is measured. The portion of light that is reflected and/or transmitted is indicative of the blood glucose level. Such glucose meters are used for tissue investigation in different depths varying from 1 to 100 millimeters or 10 to 50 micrometers. Some glucose meters use Raman spectroscopy to measure scattered light that has been influenced by the oscillation and rotation caused by glucose. Glucose meters based on photo-acoustic spectroscopy measure parameters of an acoustic pressure wave created by rapid heating of the sampled area. Other glucose meters measure changes in the scattering and the polarization parameters of light caused by glucose. Femtosecond pulse interferometry can be used to determine glucose concentration, by measuring the group refraction index of a glucose solution using a time delay of femtosecond order in a time-of-flight method. Optical coherence tomography can be used to measure and analyze the interference pattern between the coherently backscattered light from specific layers of tissues and a reference beam.

With regard to blood alcohol level, alcohol level is usually examined by determining blood alcohol concentration (BAC) in breath and blood of the affected person. The principle of BAC measurement is based on the fact that alcohol, taken orally, goes into the body system. Equilibrium distribution of alcohol into the different parts of the body mainly liver, kidney, brain, and lungs is attained very rapidly. The ratio of alcohol in the blood to alcohol in alveolar air is approximately 2,100:1 at 34° C., the temperature at which the breath leaves the mouth. Thus, the extent of alcohol intoxication or alcohol consumption is monitored by examining BAC in breath and blood of the affected person, but the obvious choice is blood, an absolute level can be obtained only by drawing a sample of blood. There are several methods for the estimation of BACs using iodometric titrations, breath analyzer, and biosensors.

With regard to intraocular pressure, the most commonly used ophthalmic device for measuring IOP, and current gold standard, is called applanation tonometer known as Goldmann tonometer. It is based on the assumption that the eye is a perfect sphere. Thus, the force required to achieve a fixed degree of applanation (3.06 mm in diameter) when the tonometer head directly applanates the cornea is converted into millimeters of mercury (mmHg) providing the IOP resisting this deformation. Despite of its accuracy and precision, Goldmann tonometry mainly suffers from inter-individual variations due to difference in corneal thickness and rigidity while being an invasive (contact) technique with limitations for monitoring the IOP over time. Note also that this standard method, which involves touching the cornea, also consequently necessitates the use of anesthetic eye drops. As alternative, one can measure the area of applanation when a given constant force is applied to the eye. This can be accomplished, for instance, by blowing from a given distance with a standard blast of air into the eye and measuring the applanation area of the cornea. Using this procedure, the contact in the measurement is avoided but the technique still remains unpractical for monitoring IOP at large periods of time, that is, it fails when identifying peaks and IOP variations.

This single measurement working principle of classical tonometers has encouraged researchers to develop new ways of continuous IOP monitoring. Some examples are the use of sensing contact lenses, some sort of implants with telemetric pressure transducers and devices based on optical principles. The latter is described for example in the following publications: Asejczyk-Widlicka, M., Pierscionek, B. K., *Fluctuations in intraocular pressure and the potential effect on aberrations of the eye*, Br. J. Ophthalmol. 91, 1054-1058, 2007; De la Torre-Ibarra, M. H., Ruiz, P. D., Huntley, J. M., *Double-shot depth-resolved displacement field measurement using phase-contrast spectral optical coherence tomography*, Opt. Express 14, 9643-9656, 2006; Matsumoto, T., Nagata, R., Saishin, M., Matsuda, T., Nakao, S., *Measurement by holographic interferometry of the deformation of the eye accompanying changes in intraocular pressure*, Appl. Opt. 17, 3538-3539, 1978.

GENERAL DESCRIPTION

The present invention aims at providing a novel technique for non-invasively and contactless monitoring one or more parameters/conditions of a subject by analyzing image data corresponding to defocused images of secondary speckle pattern responses of the subject varying over time in response to coherent illumination. More specifically, the invention is used for monitoring/measuring parameters/properties of bodily fluids, such as blood, aqueous humor, cerebrospinal fluid in the cranium, and is therefore described below with respect to this specific medical application. Also, as will be described below, the principles of the present invention may be utilized in an endoscope-based system for monitoring one or more biomedical parameters/conditions of (or related to) an internal organ by analyzing image data corresponding to defocused images of secondary speckle pattern generated at a surface of the internal organ. For example, the present disclosure may be used for monitoring (measuring) one or more parameters (properties) of fluid streams within organs as well as for detecting different types of infections, e.g. retinal diseases, cancer cells and etc. It should be understood that the term "organ" may also be contemplated as a portion of an organ in the following description. For example, an organ in the meaning of the present disclosure may refer to a blood vessel or to a tumor cell within an organ. Further, the term "internal organ" may refer generally to an organ/tissue in a subject's body i.e. accessible by invasive techniques involving incision of the skin or by non-invasive techniques which do not involve incision of the skin such as endoscopy or puncture, etc.

The present invention makes use of the imaging technique disclosed in PCT Patent Publication WO2009/013738 developed by co-inventors of the present application and assigned to the assignee of the present application. This technique is aimed at determining a motion of an object by an optical system, a so-called "opto-phone". According to this technique, a coherent speckle pattern propagating from an object is imaged, using an imaging system focused on a plane displaced from the object.

The inventors have now identified that various biological or biochemical conditions of a subject's body affect a motion of the respective body portion. For example, the glucose level and alcohol level in blood affect, inter alia, the viscosity of blood. A change in the blood's viscosity affects the friction between the blood fluid and the vessel walls, and therefore produces a unique vibration profile in the blood vessel and on the skin proximal to the blood vessel. In addition, some of the above mentioned chemicals, such as alcohol, affect the rate and shape of the heart pulsation which can be extracted using the proposed optical technique. The present invention is thus based on the understanding that there is a defined relation between a motion of the body portion (resulting from a motion of a bodily fluid in said portion) and one or more properties of the fluid. The inventors have therefore developed a novel technique that utilizes relations between various parameters, characterizing a change in detected speckle pattern from the body over time, and the body conditions.

Thus, the present invention generally provides an optical technique for monitoring/measuring various parameters/conditions of a subject (an individual) that affect an optical response of a region of interest in the subject's body to incident light due to motion effects in said region of interest. The motion effects can be determined by analyzing the optical response being in the form of a sequence of speckle patterns returned from a portion of the subject's body in response to illumination thereof by coherent light according to a certain sampling time pattern.

According to the invention, speckle pattern is detected over time with a certain sampling rate, and variations of the speckle pattern images are determined. More specifically, a spatial correlation function between successively sampled frames (images) is determined. The correlation function typically has a Gaussian-like spatial profile and can therefore be described by a "correlation peak" whose temporal variations correspond to a change in the speckle pattern over time. This may be a change in a position (shift) of the speckle pattern in the detector plane causing the change in the spatial position of the correlation peak (the shift of the speckle pattern in time shifts also the obtained spatial correlation peak), and/or a change in the shape or distribution of the speckle pattern causing the change in the correlation peak value. Then, the change in location and/or value of the peak of the spatial correlation function over time (corresponding to the change in the speckle pattern as a result of motion of the corresponding body portion being imaged) is analyzed in accordance with the condition/property to be determined. To this end, the invention utilizes predetermined models, each model presenting a relation between one or more parameters of the time varying spatial correlation function (e.g. the time varying position of the spatial correlation peak or the time varying value of this peak) and a biological or biochemical property/condition of the body. Thus, appropriate one or more parameters of the temporal change in some features of the spatial correlation function (as the temporal change in the position of the peak of the spatial correlation function or in its value) are determined and then the selected model is applied to determine biological or biochemical property/condition.

With reference to blood, the inventors have found that human blood vessels vibrate due to variable (from systolic to diastolic) blood pressure. The human wrist may be one possible spot for blood vessels observation and vibration analysis, especially for heart beat monitoring. As the motion of the blood vessels is a function of blood pressure change, appropriate detection of the blood vessels' movement provides for determining various properties/conditions of the blood, such as those related to blood pressure, namely blood pulse pressure (the difference between the systolic and diastolic pressures), as well as blood flow volume (relative), pulse wave velocity, substance concentration in blood, etc.

A vibration profile of a blood vessel is a unique one. It is characterized by many individual properties, such as vessel elasticity, human fat layer, blood viscosity etc. Therefore any change of one of these properties can distort this profile. For example, the glucose level and alcohol level in blood affect, inter alia, the viscosity of blood. A change in the blood's viscosity affects the friction between the blood fluid and the vessel walls, and therefore produces a unique vibration profile in the blood vessel and on the skin proximal to the blood vessel. In addition, some of the above mentioned chemicals, such as alcohol, affect the rate and shape of the heart pulsation, which can extracted using the proposed optical technique.

According to some embodiments of the present invention, there is provided an optical technique to monitor substance concentration/level in blood based on determining and analyzing a change in the speckle pattern over time caused by skin vibrations due to blood flux pulsation. The secondary speckle pattern's spatial correlation function is indicative of the motion of a region of human skin (e.g. skin on the wrist) illuminated by a spot of laser beam, and can be therefore used to determine the substance concentration/level in blood. One or more properties of the blood can be extracted by determining parameters in the time varying characteristics of features in the spatial correlation function of the speckle pattern (features as the position of the correlation peak or its value) generated in response to coherent illumination of the skin portion. For example, the inventors have shown that at least one parameter of the temporal change in the spatial correlation function is in good agreement with the blood glucose level estimated by a conventional measurement technique. Also, the inventors have shown that parameter(s) of the temporal change in the spatial correlation function is in good agreement with blood alcohol level measured by a conventional technique.

With reference to aqueous humor, the inventors have found that intraocular pressure affects the vibration of the eye (e.g. sclera, iris, eye lid), and that a relation exists between intraocular pressure and some parameters of the temporal change in the spatial correlation function of a secondary speckle pattern generated in response to coherent illumination of the eye (the temporal change in the spatial correlation function being indicative of the eye's vibration over time). Therefore, according to some embodiments of the present invention, there is provided a technique for measuring intraocular pressure based on detection and analysis of the temporal change in the spatial correlation function.

According to some further embodiments of the present invention, beams of several wavelengths (generally, at least two wavelengths) may be used to (simultaneously or successively) illuminate the region of interest, and the secondary speckle pattern (and the corresponding time varying spatial correlation function) is determined for each wavelength separately. The time varying spatial correlation function is determined for each wavelength, and a relation between these two or more functions is determined, or a relation (e.g. ratio) between selected parameters of the different time varying spatial correlation functions is determined, as the case may be. More specifically, the time varying spatial correlation function for each wavelength is used (e.g. the change in the position of the spatial correlation peak with time), and the two functions, corresponding to the two different wavelengths are divided one by the other; then the so-obtained time varying ratio is utilized to define the parameter of interest (e.g. the width of peaks, the standard deviation of background noise, etc.), for determination of the blood parameter using one or more appropriate models. This can be useful, for example, in the estimation of blood oxygen level which today is done by pulse oxymetry based on determination of the ratio of transmission of the blood in two predefined wavelengths.

Therefore, according to an aspect of some embodiments of the present invention, there is provided a system for use in monitoring one or more conditions of a subject's body. The system includes a control unit, which includes an input port, a memory utility, and a processor utility. The input port is configured for receiving image data in the form of a sequence of speckle patterns generated by a portion of the subject's body according to a certain sampling time pattern.

The memory utility is configured for storing one or more predetermined models, the model comprising data indicative of a relation between one or more measurable parameters and one or more conditions of the subject's body. The processor utility configured and operable for carrying out the following: processing the image data and determining a spatial correlation function between successive speckle patterns in the sequence, and determining a time varying spatial correlation function in the form of a time-varying function of at least one feature of the correlation function, the time-varying spatial correlation function being indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

The at least one feature of the correlation function comprises at least one of the following: a position of a peak of the correlation unit, and a value of a peak of the correlation function.

The at least one parameter of the time varying function may comprise at least one of the following: pulse size, positive pulse size, positive pulse amplitude, distance between peak polarities, ratio between main and secondary peak positions, ratio between main and secondary peak amplitudes, ratio between positive and negative peak amplitudes, and standard deviation of background noise. The one or more body conditions to be monitored include one or more of the following: blood glucose concentration, intraocular pressure (IOP), and bone fracture, blood alcohol concentration, blood pulse pressure, coagulation of blood, temperature, flow velocity and volume.

According to a second aspect of some of the embodiments of the present invention, there is provided a system for use in monitoring one or more conditions of a subject's body. The system includes an imaging device, an external field generator, and a control unit. The imaging device is configured for imaging a predetermined portion of the subject's body, the imaging device comprising a coherent light source for illuminating said portion of the subject's body with a predetermined number of wavelengths according to a certain sampling time pattern, and a pixel detector array configured and operable for detecting secondary speckle pattern generated by the illuminated portion of the body and generating measured image data indicative of the detected secondary speckle pattern. The control unit is configured and operable for receiving the measured image data and data indicative of the external stimulation applied to the region of interest during the imaging, the control unit comprising: a memory utility for storing one or more predetermined models, the model comprising data indicative of a relation between one or more measurable parameter and one or more conditions of the subject's body; and a processor utility configured and operable for: processing the image data utilizing the data indicative of a waveform of the applied stimulation, and determining a spatial correlation function between successive speckle patterns in the sequence, and determining a time varying spatial correlation function in the form of a time-varying function of at least one feature of the correlation function, the time-varying spatial correlation function being indicative of a change of the speckle pattern over time; selecting at least one parameter of the time-varying spatial correlation function, and applying to said at least one parameter one or more of the models to determine one or more corresponding body conditions; and generating output data indicative of said one or more corresponding body conditions.

According to a further aspect of some embodiments of the present invention, there is provided a method for use in monitoring one or more conditions of a subject's body, the method comprising: providing input data indicative of an external stimulation applied to a portion of the subject's body under optical measurements, providing image data measured by a pixel detector array and being in the form of a sequence of speckle patterns generated by the portion of the subject's body in response to illumination thereof by coherent light according to a certain sampling time pattern and application of said external stimulation; providing one or more predetermined models, the model comprising data indicative of a relation between one or more measurable parameters and one or more conditions of the subject's body; processing the image data utilizing said data indicative of a waveform of the applied external stimulation, wherein said processing comprises determining a spatial correlation function between successive speckle patterns in the sequence, and determining a time-varying spatial correlation function in the form of a time-varying function of at least one feature of the correlation function, the time-varying spatial correlation function being indicative of a change of the speckle pattern over time; analyzing the time-varying spatial correlation function and selecting at least one parameter of the time-varying function in accordance with one or more body conditions to be determined; and analyzing said at least one selected parameter using one or more of the models to determine one or more corresponding body conditions, and generating output data indicative thereof.

In some embodiments of the present invention, said one or more conditions of a subject's body are associated with one or more properties of at least one bodily fluid.

Optionally, said at least bodily fluid comprises at least one of blood and aqueous humor.

The technique of the present invention provides for measuring various bio-chemical parameters of a subject, by properly obtaining data indicative of a shift in a speckle pattern (resulting from de-focused imaging) caused by motion/vibrations within a region of interest of the subject's body, and properly analyzing data indicative of the vibration profile. Several such parameters can be measured simultaneously. In a case of heart beats rate, the time between the beats (between two highest amplitudes in the local time slot) is identified. In a case of breathing, a biased sinusoidal profile at slow frequency (less than 0.5 Hz) is identified, being easily separated from heart beats rate by the shape and the frequency (also by analyzing the frequency domain diagram). For the blood pulse pressure measurements, the difference in the dynamic range of the heart beat peak (the difference between the positive and the negative peaks of the vibration profile) is identified. For the oximetry monitoring, the standard deviation of the 10 seconds time window in the vibration profile is determined. For performing the coagulation analysis, a collection of each pulse profile one over another in the same time domain is first constructed, being something similar to "eye" diagram used in communication equipment (eye diagram is an indicator of the quality of signals in high-speed digital transmissions). For construction of the "eye" diagram, each one of the OCG (Opto cardiography) pulses is cut from the time vibration vector according to the shape and all of the pulses are pasted one on another (i.e. construction of an "eye diagram" shape), and this step is repeated for every optical sample.

In the embodiments of the invention in which the external stimulation is applied, this may be a temporally periodic stimulation, e.g. a magnetic field or an acoustic pressure field (e.g. for measuring glucose concentration, IOP, bones fractures), the position of the correlation peak between adjacent speckle images is determined and the temporal chart of the change in the position of the correlation peak is obtained. Then, the Fourier transform of this temporal chart is determined and its spectrum is obtained, thereby enabling to examine the amplitude value of the spectrum at the stimulation frequency of the external simulator. In some embodiments, the external stimulation is a DC field, such as a magnetic field generated by a permanent magnet. This may be used for glucose concentration measurement. In this case, the main peak of the measured function selected for examination is the peak of the highest amplitude corresponding to the glucose response.

As indicated above, the invention can be used together with a conventional imaging system such as endoscope of any suitable configuration for inspecting/measuring internal organs of a subject. Endoscopes are the common medical instrumentation to perform medical inspection of internal organs. There are two main types of endoscopes: flexible and rigid.

The flexible endoscopes are being constructed out of a bundle of single mode fibers while each fiber in the bundle transmits backwards spatial information corresponding to a single spatial point, i.e. a single pixel. The fibers bundle may go into the body while the imaging camera is located outside. Interface optics adapts the photonic information coming out of the bundle to the detection camera. The reason for using single mode fiber for each fiber in the bundle rather than multi mode fibers (capable of transmitting spatial information that is corresponding to plurality of pixels) is related to the fact that when inserting the endoscope and while navigating it inside the body it may be bent. When multi mode fibers are bent the spatial modes are coupled to each other and the image is strongly distorted. The typical diameter of a single mode fiber in the bundle is about 30 μm (this is the diameter of its cladding, the core has diameter of about 8-9 μm). The typical number of fibers in the bundle is about 10,000-30,000. Typical overall diameter (of the entire bundle) is about 3 mm-5 mm.

For example, an endoscope utilizing a multicore fiber is described in US Patent Publication US 2010/0046897 which discloses an endoscope system including an image fiber with an image fiber main body made of a plurality of cores for forming pixels and a cladding common thereto; and an optical system connected to an eyepiece side of the image fiber for causing laser light to enter the image fiber and for taking in an image from the image fiber, in which the image fiber has the cores arranged substantially uniformly over a cross-section of the image fiber main body, the cross-section being perpendicular to a longitudinal direction of the image fiber main body.

Thus, according to yet another aspect of the invention, there is provided a monitoring system for use inspecting an internal organ, the system comprising an imaging device for imaging a predetermined portion of the subject's body, and a control unit. The imaging device comprises a coherent light source for illuminating said portion of the subject's body with a predetermined number of wavelengths according to a certain sampling time pattern, and a pixel detector array configured and operable for detecting secondary speckle pattern generated by the illuminated portion of the body and generating measured image data indicative of the detected secondary speckle pattern. Generally, the imaging device may have any suitable known configuration. In some embodiments, the imaging device comprises a multicore fiber configured for transferring light between a proximal end and a distal end of the multicore fiber which is intended to be placed in proximity of the internal organ. The control unit is configured and operable as described above for receiving and analyzing the measured image data, using one or more predetermined models comprising data indicative of a relation between one or more measurable parameter and one or more conditions of the subject's body, to determine a spatial correlation function between successive speckle patterns in the sequence.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2A-2B are schematic drawings illustrating the principles of the technique for measuring motion of an object used in the measurement unit of the system of FIG. 1A or 1B;

FIGS. 8A-8D are graphs illustrating the change in a second test subject's blood glucose level and the corresponding change in the amplitude of positive peak (parameter 1 of FIG. 6A);

FIGS. 10A-10D are graphs illustrating the change in a fourth test subject's blood glucose level and the corresponding change in the amplitude of positive peak (parameter 1 of FIG. 6A);

FIGS. 27A to 27C present the experimental results for oxygen saturation measurements utilizing the system of the invention exemplified in FIG. 1B, obtained for two saturation level experiments and compared with a reference measurement obtained using a convention pulse oxymeter;

DETAILED DESCRIPTION OF EMBODIMENTS

Figure 1A:
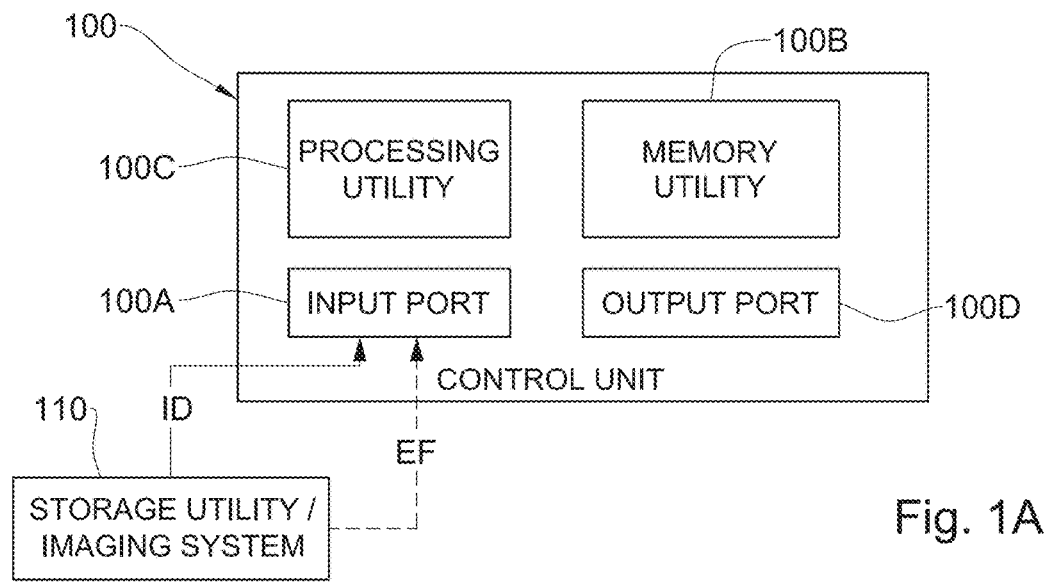
FIG. 1A is a block diagram of a system of the present invention for monitoring a subject's condition by measuring one or more biological or biochemical parameters/conditions of the subject.

Referring now to the drawings, FIG. 1A is a block diagram of a system, generally designated 100, configured and operable according to the invention for use in monitoring one or more conditions of a subject's body. The system 100 is configured as a computer system and includes input port/utility 100A for receiving input data including image data ID; a memory utility 100B for storing one or more predetermined models; a processor utility 100C; and an output data utility 100D, for example associated with a display. As shown in the figure in dashed lines, input data may also include data indicative of a predetermined external field EF applied to a region of interest of the subject's body during measurements (during imaging). This will be described more specifically further below with reference to FIG. 11A.

The system 100 is connectable (via wires or wireless signal transmission) to an imaging system or to a data storage utility, generally at 110, for receiving the input image data which is measured data in the form of a sequence of speckle patterns generated by a pixel detector array being indicative of an optical response of a portion of the subject's body to illumination by coherent light according to a certain sampling time pattern. The imaging system 110 may be a motion measurement system configured generally similar to that of the above-indicated PCT Patent Publication WO2009/013738.

As mentioned above and will be described more specifically further below, the input data may also include data about an external field or stimulus applied to the region under measurements, which data may also be received directly from a measurement system (a so-called "on-line mode) or from the storage utility ("off-line" mode). In this case, the imaging system is associated with an external field generator which is some applications (e.g. when the external field is an acoustic pressure field useful for the IOP, bone fracture measurements, etc.) operates as a so-called vibration/motion affecting unit.

The memory utility 100B stores one or more predetermined models indicative of a relation between one or more measurable parameters and one or more conditions of the subject's body. The processor utility 100C is preprogrammed for processing the image data and utilizing one or more selected models to generate output data indicative of the one or more corresponding body conditions. To this end, the processor utility analyzes the image data and determines a spatial correlation function between successive speckle patterns in the sequence, and a time varying spatial correlation function in the form of a time-varying function of at least one feature of the correlation function. The time-varying spatial correlation function is indicative of a change of the speckle pattern over time. Then, at least one parameter of the time-varying spatial correlation function is selected, and one or more of the models is applied to this at least one parameter to determine one or more corresponding body conditions.

Figure 1B:
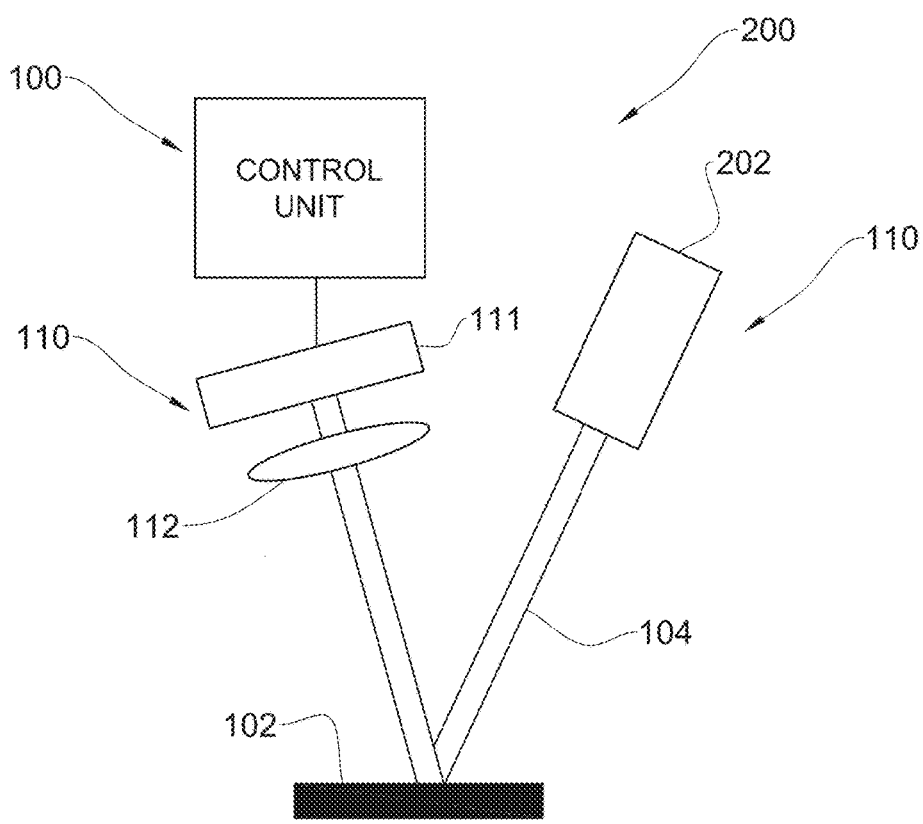
FIG. 1B is a schematic illustration of the system of the invention used together with an imaging system for measuring a motion of a portion of the subject's body.

Referring now to FIG. 1B, there is schematically illustrated a system 200 for use in monitoring the subject's body condition(s), e.g. measuring at least one property of a bodily fluid, including a measurement unit 110 and a control unit configured as the above-described system 100. The measurement unit 110 includes a source of coherent light 202 (e.g. laser source), an imaging unit having a pixel detector array (PDA) 111 and an imaging optics (e.g. single lens) 112. The control unit 100 is connectable via wires or wireless signal transmission (e.g. RF, IR, acoustic) to the output of the PDA 111, and in some applications the same or additional control unit may include an illumination controller for selecting appropriate wavelength(s) for illumination.

The source of coherent light 202 emits a light beam 104 to illuminate the object 102 during a certain time period (continuously or by multiple timely separated sessions). The object constitutes a body region of a subject (e.g. individual) whose movement is affected by a change in the body condition, typically a flow of a fluid of interest (i.e. a fluid having a property that is to be measured). The object's diffusive surface responds to coherent illumination by a speckle pattern which propagates toward the imaging optics 112 and is captured by the PDA 111 during said certain time period, to generate output measured data.

As shown more specifically in FIGS. 2A and 2B, the imaging unit is configured for focusing coherent light on a plane 108 which is displaced from a plane of an object 102 to be monitored. In other words, the back focal plane of the lens 112 is displaced from the object plane thus producing a defocused image of the object. A coherent light beam 104 (e.g., a laser beam) illuminates an object 102, and a secondary speckle pattern is formed as the reflection/scattering of the coherent light beam 104 from the object 102. The secondary speckle pattern is generated because of the diffusive surface of the object 102. The speckle pattern propagates toward the in-focus plane 108, where it takes a form 106. The speckle pattern propagates in a direction along the optical axis of the system, is collected by the imaging lens 112 and is collected by the PDA 111.

If the object 102 moves in the transverse direction (i.e. into and out of the page, or up and down), the detected speckle pattern changes phase. If the object 102 moves in the axial direction (toward and away from imaging lens 112), the detected speckle pattern changes scale. If the object 102 tilts (as shown in FIG. 2B), then the speckle pattern in the PDA plane shifts position. The scale and shape change as well as the position shift of the speckle pattern are detectable by the PDA, thereby allowing detection of the object's motion along the axial direction and tilting.

With reference to tilting, in FIG. 2A the speckle pattern is detected in the region A of the PDA 110, while in FIG. 2B following the tilt on the object's surface by an angle α, the speckle pattern illuminates and is detected by a region B of the PDA 111. The relative shift of speckle pattern due to the displacement of the object's surface (the object 102) can be estimated as $$\beta = \frac{4\pi \tan\alpha}{\lambda} \approx \frac{4\pi\alpha}{\lambda} \quad (1)$$

where β is proportional to the relative shift δ of the speckle pattern (i.e. the distance between points A and B), α is the tilting angle of object's surface, and λ is the optical wavelength. Assuming that the change in the angle is small enough, a linear proportion is obtained between the relative shift and the angle of tilting.

In light of the above, it can be seen that the object's movement causes changes in properties/profile (phase, magnification, position) of the speckle pattern detected by the PDA 110. Therefore, monitoring a change in the speckle pattern over time is associated with the movement of the object 102 and thus enables detection and characterization of the movement of the object 102.

Figure 3A:
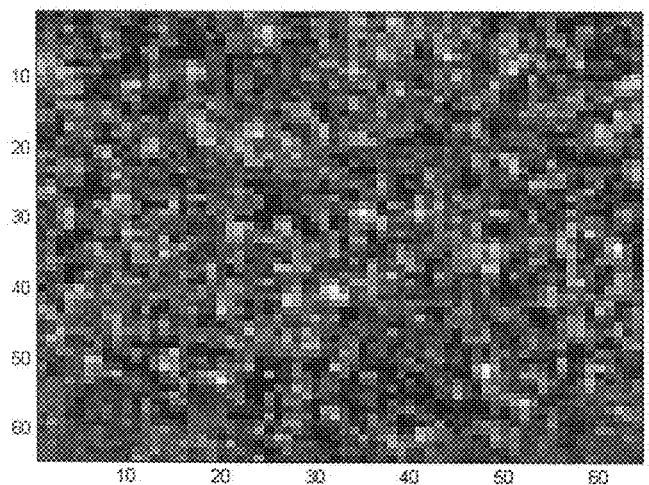
FIGS. 3A-3C exemplify the processing of measured data by the control unit of the system of FIG. 1A or 1B.
Figure 3B:
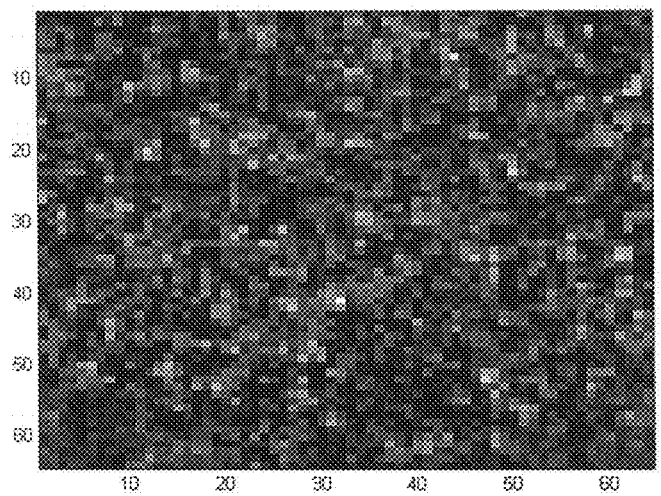
Figure 3C:
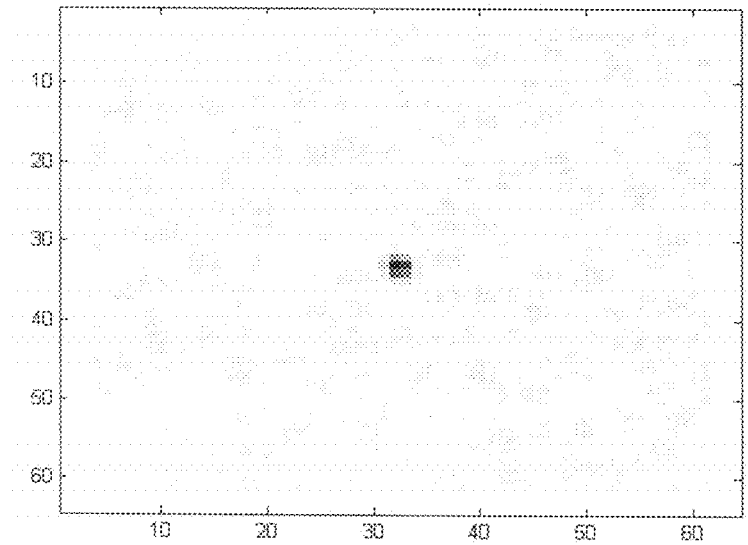

According to the present invention, the control unit 100 receives the measured data (or data indicative thereof and appropriately formatted) from the pixel(s) of the PDA 111 illuminated by the speckle pattern response of the object, and processes this measured data to form a spatial correlation function by determining correlation between successive images of the speckle pattern. As exemplified in FIGS. 3A-3C, measured data is in the form of a sequence of speckle patterns generated by the object in response to coherent illumination according to a certain sampling time pattern—two such successively received speckle patterns being shown in FIGS. 3A and 3B. The control unit processes these speckle patterns and determines a correlation function between them, as exemplified in FIG. 3C being in the form of a correlation peak. The black area in FIG. 3C represents the peak of the correlation function between the speckle patterns in FIGS. 3A and 3B.

The control unit 100 is configured for extracting one or more features of the spatial correlation function (e.g. the shift in the correlation peak and/or the change of its value) and monitoring temporal changes of such extracted features, in order to construct data indicative of time variation in the correlation function. The time variation in the correlation function is in turn indicative of variation of the speckle pattern, and therefore of motion in the illuminated body part, which causes such variation in the speckle pattern. Then, from the data indicative of the time variation of the spatial correlation function, one or more parameters are extracted and used for determining one or more conditions of the body.

The optics 112 is slightly defocused with respect to the object's plane. This feature is important in order to convert the tilting movement of the object's surface into transversal movement of the speckles. This provides that the only varying property of the detected speckle pattern, returned from object that undergoes a tilting movement, is its position in the coordinate system of the PDA (i.e. pixel matrix) while other properties (phase and magnification) practically do not change during the tilting of the illuminated object. A time function of the shift of such speckle pattern is tracked by the control unit which operates to apply a certain algorithm to the measured data for correlating the amplitude of the object's motion to the shift in the speckle pattern. In this connection, it should be understood that the speckle pattern shift along the PDA pixel matrix is indicative of the tilting movement of the object with respect to the optical axis, while a change in the scaling (magnification) of the speckle pattern is indicative of the object's motion along the optical axis, and a change in phase of the speckle pattern is indicative of the object's motion substantially perpendicular to the optical axis. The amount of applied defocusing determines the amount of change in each one of the above mentioned properties.

As explained above, the inventors have found that in bodies of humans and animals, one or more properties of a bodily fluid affect the motion of nearby body regions. For example, properties of flowing blood affect the motion of skin on a person's wrist. The pressure of the aqueous humor (i.e. the IOP) affects involuntary vibrations in the eye. The intra cranial pressure affects the motion of the surface of the eardrum. Therefore, the temporal change in the correlation function (as indicated, for example by temporal change of the position and/or value of the obtained correlation function's peak) is indicative of properties (conditions) of the fluid of interest. Therefore, the control unit 100 is configured to perform an analysis of the temporal variations of one or more features of the correlation function (such as the position and/or the value of the correlation peak), caused by time changes of the speckle pattern detected from the object during measurements. From the temporal change in the correlation function analysis, one or more parameters are extracted, these parameters being related to one or more properties of the fluid. The parameters are thus used to determine one or more properties of the fluid.

As described above, the control unit 100 includes an input port 100A connected to the output of the PDA 111 and configured for receiving measured data indicative of the detected speckle pattern from the PDA's illuminated pixel(s), a processing utility 100C (software/hardware utility), a memory utility 100B, and an output port 100D associated with a data presentation utility or an external storage device, as the case may be. The control unit's processing utility 100C is configured to construct the speckle pattern's spatial correlation function according to the data received from the PDA; the spatial correlation function data may be stored in the memory utility. The processing utility 100C includes appropriate functional modules for determining a spatial correlation function, analyzing the spatial correlation function and extracting one or more features thereof and tracking their variation over time, and constructing data related to the temporal change in the spatial correlation function. Subsequently, the processing utility 100C utilizes a predetermined model (stored in the memory utility) selected for one or more body conditions to be monitored, and analyzes the temporal changes in the object's spatial correlation function according to the selected model. Generally, the model defines one or more sets of parameters (variables) of the temporal changes in the spatial correlation function, the parameters being associated with properties of a certain bodily fluid (e.g., via algorithm or look-up table). Thus, the processor utility 100C analyzes the spatial correlation function and identifies therein the values of one or more of the parameters. Once the parameters are extracted from temporal variations in the spatial correlation function, the processing utility 100C operates for calculating one or more properties of the fluid, according to the selected model.

As will be described more specifically further below, the second set parameters relating to the temporal change in the spatial correlation function may include an average amplitude of a sinusoidal vibration of the temporal change in the correlation function, and/or parameters describing peaks in the temporal change in the correlation function, e.g. the width of the first positive peak.

The output port 100D is configured for transmitting output data from the control unit to one or more output devices (e.g. display, printer, speaker), or to the monitor of the control unit, in order to present data to a user. The output data may include a graph of the temporal changes in the spatial correlation function and/or values of one or more of the extracted parameters, and/or values of one or more properties of the fluid.

As will be explained below, the system 100 (control unit) may be configured, inter alia, to determine blood-related parameters, such as concentration of substance in blood (e.g. glucose concentration, blood alcohol concentration) and/or oxygen saturation, and/or blood flow volume (relative), blood pulse wave velocity, as well other bodily fluid related parameters such as intra-ocular pressure and/or intra-cranial pressure.

The measurement unit 110 may be configured as an endoscope for inspecting internal organs. Generally, the endoscope may be of any known suitable configuration, in which, for the purposes of the present invention, an optical assembly is configured for setting a predetermined defocus between the surface of the internal organ and the detector array.

Figure 4:
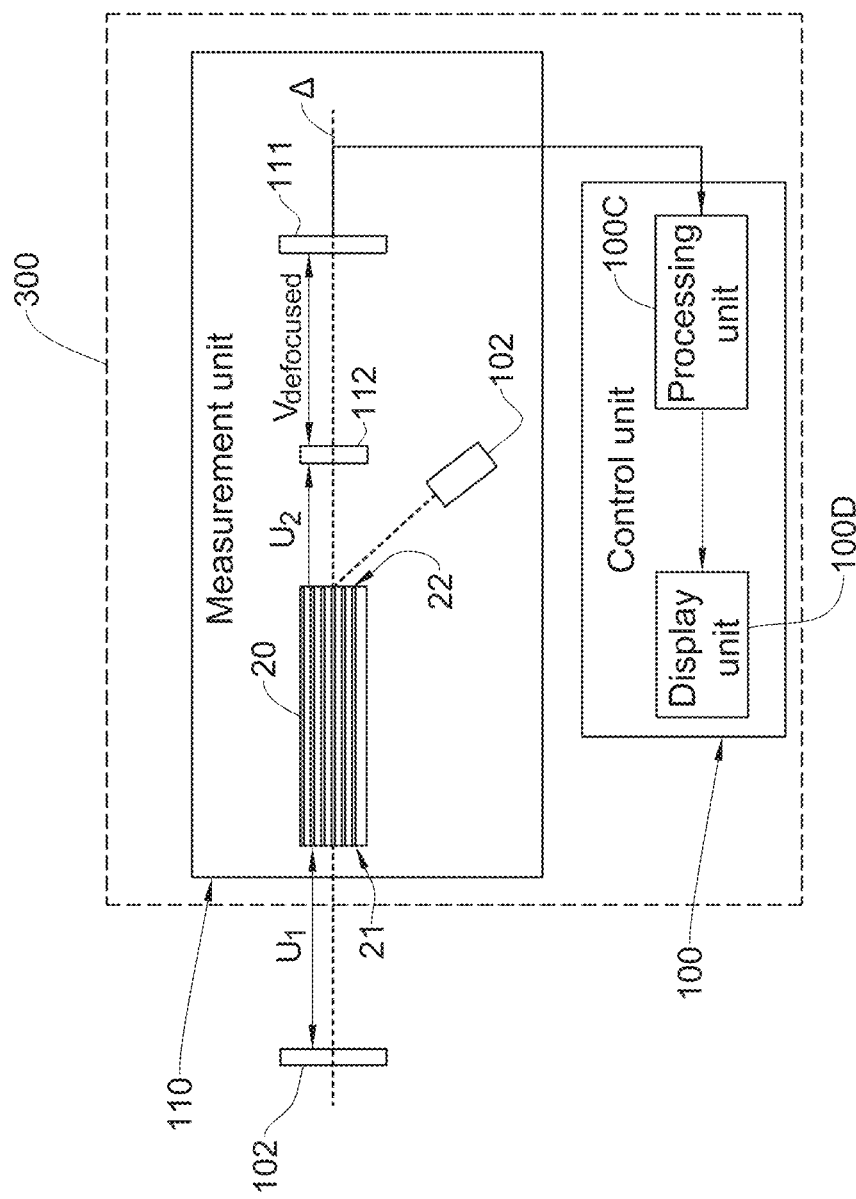
FIG. 4 exemplifies the use of the system of the invention with an endoscope, and shows a specific but not limiting example of the configuration of a light guiding unit suitable to be used in the endoscospe.

FIG. 4 shows specific but not limiting example a system of the present invention 300 formed by the above-described control unit 100 and a measurement unit 110 including an endoscope-based imaging system configured for providing measured data in the form of a sequence of speckle response to coherent de-focused illumination. The system 300 is adapted for monitoring biomedical parameter of an internal organ (object) 102. The measurement unit 110 includes a source of coherent light 202, a detector array 111 (e.g. including a CCD), an optical assembly 112, and a light guiding unit 20.

The light guiding unit 20 is configured as a micro probe that transfers light arriving from the internal organ 2 to an input edge (distal tip) 21 of the micro probe 20 toward an output edge 22 (proximal tip) of the micro probe 20. The optical assembly 112 may be configured to collect light at the output edge 22 of the micro probe 20 and to form a defocused image of a surface of the internal organ 102 on the pixel detector array 111. The optical assembly may comprise one or more lenses, as well as may be displaceable along an optical axis Δ so as to be capable of performing defocused imaging of an object at variable distance of the input edge 21 of the micro probe 20.

In a focused imaging configuration (from which the present disclosure differs), since in respect to its imaging related property, the micro probe 20 may actually be regarded as if the input and output edges 21, 22 of the micro probe 20 act similarly to principle planes of a lens, the position of the optical assembly 30 in order to obtain focused imaging may be determined according to the following relation:

$$\frac{1}{U_1 + U_2} + \frac{1}{V} = \frac{1}{F} \quad (2)$$

wherein $U_1$ is the distance between the internal organ 102 and the input edge 21 of the micro probe 20, $U_2$ is the distance between the output edge 22 of the micro probe 20, V is the distance between an optical center of the optical assembly 112 and the detection array 10 and F is the focal length of the optical assembly 112. In the defocused configuration of the present disclosure, the above position of the optical assembly 112 obtained using the abovementioned relation is not respected so that a slight defocusing exists. For example, the distance between the optical assembly 112 and the detector array 111 is different than the distance V obtained using the relation abovementioned.

Further, the micro probe 20 may be a multicore fiber. The diameter of a core and the diameter of the multicore fiber 20 may be respectively referred to as d and D. The values of d and D are defined by fabrication and application related limitations. For example, D may be smaller than 300 μm in order to remain non invasive in certain medical applications. The value of d may be determined according to a desired spatial resolution. If D is equal to 300 μm and one wishes to have 100×100 pixels resolution it means that d may be about 3 μm. Generally, d may be larger than an optical wavelength of the light collected in order to allow coupling of light to the fiber with sufficient energetic efficiency.

The illumination source 202 is a source of coherent light and is configured to inject an illumination beam into the input edge 21 of the micro probe 20 so that a speckle pattern can be generated at a surface of the internal organ 102. The speckle pattern generated may propagate back toward the input edge 21 of the micro probe 20 to the output edge 22 of the micro probe 20. The optical assembly 112 may perform defocused imaging of the speckle pattern on the detector array 111.

As described above, the control unit 100 may be connected to an output of the detector array 111 via wires or wireless signal transmission (e.g. RF, IR, acoustic, etc.) and in some embodiments, the processing unit may be associated with the light source for selecting one or more appropriate wavelengths for illumination. The processing unit 100C may receive image data from the pixels of the pixel detector array 111 illuminated by the speckle pattern, and process the image data to calculate a correlation function between successive images of the speckle pattern. Two such successively received speckle patterns are exemplified in FIGS. 3A and 3B described above, and the correlation function between them is exemplified in FIG. 3C being in the form of a correlation peak.

In some embodiments, the control unit 100 is configured to apply component analysis in order to characterize and separate between the temporal characteristics of the correlation peak for reflections related to different values of the inspected biomedical parameters. The rationale is that infected tissues have different temporal variations profile of speckle pattern correlation peak with respect to non-infected tissue. Basically each one of them may have its own correlation peak "signature". The term signature refers for instance to the shape, amplitude value and/or the ratio between positive and negative pulse width and etc. In addition, in case of infected tissue the severity level of the disease will act and affect differently the speckle pattern which in turn may have different type of signature. The definition of the disease severity can be evaluated or defined for instance by a "lookup table".

It should be noted, although not specifically shown that the system may further include an ultrasound device configured to excite the inspected organ. It should also be noted that the multicore fiber may be a fiber bundle or a photonic crystal, and may have a polygonal or substantially circular cross section defining two opposite substantially parallel facets.

As indicated above, the optical assembly 112 is slightly defocused with respect to the organ surface plane and to the detector array plane. This feature enables to convert the tilting movement of the organ's surface into transversal movement of the speckles. This provides that the only varying property of the detected speckle pattern, returned from the organ that undergoes a tilting movement, is its position in the coordinate system of the PDA (i.e. pixel matrix) while other properties (phase and magnification) practically do not change during the tilting of the illuminated organ. A time function of the shift of such speckle pattern is tracked by the control unit which operates to apply a certain algorithm to the measured data for correlating the amplitude of the organ's motion to the shift in the speckle pattern. In this connection, it should be understood that the speckle pattern shift along the PDA pixel matrix is indicative of the tilting movement of the object with respect to the optical axis, while a change in the scaling (magnification) of the speckle pattern is indicative of the object's motion along the optical axis. The amount of applied defocusing determines the amount of change in each one of the above mentioned properties.

As explained above, the inventors have found that in bodies of humans and animals, one or more properties of a fluid in an organ affect the motion of the organ. For example, properties of flowing blood affect the motion of the heart. Therefore, the temporal change in the correlation function (as indicated, for example by temporal change of the position and/or value of the obtained correlation function's peak) is indicative of properties (conditions) of the fluid of interest. Therefore, analysis of the temporal variations of one or more features of the correlation function (such as the position and/or the value of the correlation peak), caused by time changes of the speckle pattern detected from the organ during measurements, enables to extract one or more attributes related to one or more properties of the fluid. The attributes are thus used to determine one or more properties of the fluid. The attributes relating to the temporal change in the spatial correlation function may include average amplitude of a sinusoidal vibration of the temporal change in the correlation function, and/or parameters describing peaks in the temporal change in the correlation function, e.g. the width of the first positive peak.

The output data generated by the control unit 100 of the invention may include a graph of the temporal changes in the spatial correlation function and/or values of one or more of the extracted parameters, and/or values of one or more properties of the fluid.

As will be exemplified below, the system of the invention may be configured, inter alia, to monitor local blood-related parameters of an internal organ, such as internal blood pressure of a blood vessel, concentration of substance in blood (e.g. glucose concentration, hemoglobin concentration) and/or oxygen saturation, and/or blood flow volume (relative), blood pulse wave velocity, temperature. The system may also be configured for other medical application as reminded in the general description section.

Figure 5:
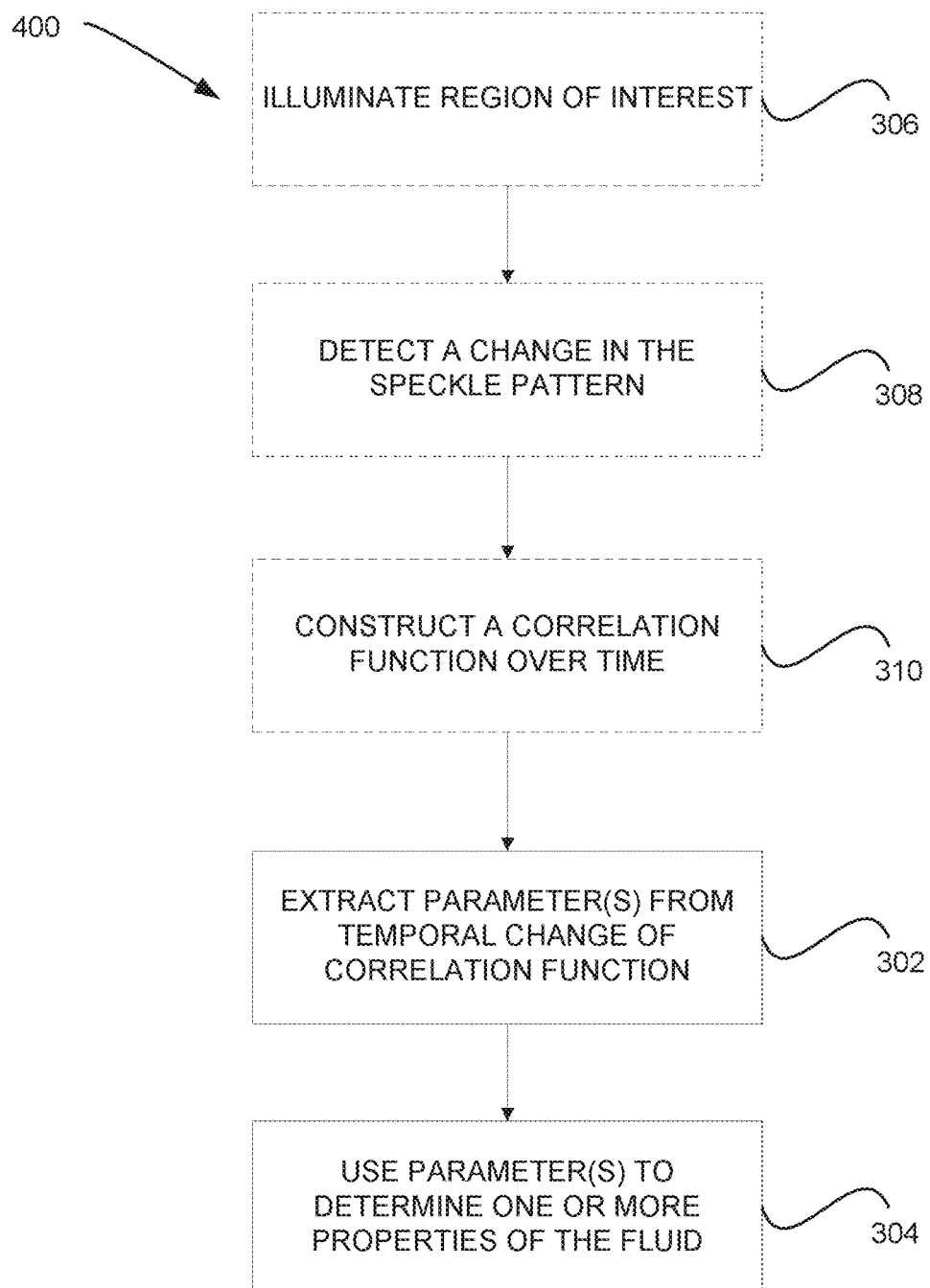
FIG. 5 is a flowchart exemplifying a method of the present invention for monitoring a subject's condition by measuring one or more biological or biochemical properties of the subject.

Reference is now made to FIG. 5, in which a flowchart 400 exemplifies a method of the present invention for measuring a property of a fluid.

At 302, a function indicative of the speckle pattern profile over time is provided and analyzed, in order to extract one or more parameters relating to the temporal shape of the spatial correlation function (as described, for example, by the temporal change in the position of spatial correlation function's peak or the temporal change in the value of this peak), in accordance to the body condition(s) to be monitored. At 304, the extracted parameter(s) is (are) used to determine one or more properties of the bodily fluid according to a predetermined model, and to generate output data indicative of the property of the bodily fluid.

The temporal change in the correlation function may be provided off-line from another processor or storage device, or as exemplified in the figure, may be provided in an on-line mode by processing and analyzing measured data (speckle patterns) from an optical measurement device at 306, 308 and 310. At 306, the region of interest is illuminated by coherent light over a certain time period. At 308, a speckle pattern response to the coherent light is detected, and images of the speckle pattern are recorded over time. Consequently, at 310, the images of the speckle pattern are analyzed to determine one or more characteristics (e.g., position and/or shape) of the speckle pattern. Change in the one or more speckle pattern characteristics is determined between subsequent images, to construct a spatial correlation function of the speckle pattern over the measurement time. One or more features of the spatial correlation function (e.g. a position of the correlation function's peak and/or a value of the correlation function's peak) are extracted and monitored over time, in order to construct data indicative of the temporal change of the spatial correlation function. The so-estimated temporal change in the correlation function can then be analyzed in step 302.

The inventors have conducted various experiments demonstrating the capability of the technique of the present invention for monitoring various subject's parameters/conditions, including for example glucose concentration in blood stream, breathing, coagulation, oximetry, as well as blood alcohol concentration, measurement of intra-ocular pressure, dehydration, monitoring of cattle, temperature, flow velocity and volume. The system of the invention can monitor several vital biomedical parameters simultaneously, and also can be realized in a very simple and cost efficient manner involving simple camera and a laser source. The technique is based on the tracking of temporal changes of reflected secondary speckle produced in a region of interest in the subject when being illuminated by a laser beam. A temporal change in the vibration profile of the region of interest generated due to fluid (e.g. blood) pulsation is analyzed for estimating the desired parameter (e.g. glucose concentration).

Speckle or speckle pattern may be produced in spatially coherent light due to self interference within the laser beam, while the temporal trajectories of the speckle patterns that are captured by the camera are proportional to the temporal signals that are to be extracted (a vibration profile). A self-interference pattern is constructed on the CCD plane of the observing camera. A temporal change in the pattern is related to a relative spatial shift between two adjacent frames taken by the camera.

It should be noted that the technique of the present invention can be used not only for measuring one or more bio-chemical parameters of a subject, but also as a highly-directional sound transmitter, which is particularly useful in a hearing aid devices. Indeed, when optically sensing vibrations of the surface which is illuminated by the laser and back reflects the light to the camera, a very directional vibrations sensing is provided, since only the region being illuminated by coherent light (laser) is relevant to the measurement. This is a very good property for hearing aid device since there one needs to amplify only the speech signals of the person speaking in front of the impaired person and not noises surrounding him. If the laser is directed towards the speaker and the laser light is back reflected only from the speaker, the camera will sense only his vibrations. If the illuminated tissue is part of his head, then the vibrations are proportional to the voice produced by the speaker. Only this signal will be input to the amplification device of the hearing aid. That way the background noises are completely filtered out.

The following are some specific non-limiting examples of the technique of the invention for determining various subject's parameters/conditions.

Blood Glucose Concentration

The following section refers to test conducted by the inventors on human subjects, in order to determine a relationship between blood glucose concentration and parameters of the time varying function indicative of the time changes of the speckle pattern caused by vibration of skin on the subjects' wrists (i.e. the temporal change in the spatial correlation function).

The connection between different blood parameters and blood glucose level is explained by:

$$C_v(t) = \frac{(1-\varepsilon) \cdot q_0 \cdot h(t)}{F} \quad (3)$$

where $C_v(t)$ is the venous glucose concentration at time t, F is the blood flow (represents the amount of blood, usually in litters per minute), $q_0$ corresponds to a glucose pulse and represents the amount of glucose (in mg) in the blood (in Kg) per heart beat, $\varepsilon$ is the fraction of the glucose pulse that is extracted from the blood system and is metabolized (therefore it will never be recovered at the outlet of the vein), h(t) is the reversible fates of glucose in the organ that causes a delay and a distortion in the appearance of glucose pulse in the vein.

A vibration profile of a blood vessel is a unique one. It is characterized by many individual parameters, such as vessel elasticity, human fat layer, blood viscosity etc. Therefore any change of one of these parameters affects a change of this vibration profile. Changes in glucose level in blood affect the viscosity of blood, while a change in viscosity of blood affects the friction between the blood and the vessel walls, while a change in the friction in turn affects the motion profile. Thus, a change of friction due to a change in glucose concentration in the arteries and veins causes a change of the vibration profile of the vessel. In order to determine glucose concentration from the analysis of the vibration profile of skin on a human wrist, the inventors have analyzed the temporal changes in a spatial correlation function corresponding to the time variations of the speckle pattern in the successive images, by observing quantitative parameters of the temporal changes in a spatial correlation function before and after glucose intake. To be more specific, the temporal changes in the spatial correlation function were in the form of the temporal variations of the spatial correlation function's peak and/or in the temporal variations of the value of the peak of the spatial correlation function. Such parameters were compared to the actual glucose level in the blood that is obtained via a reference measurement with conventional techniques.

An experimental system was constructed similar to the above-described system of FIG. 1B, and used to illuminate a wrist of a subject being fixed by gypsum to allow more accurate measurement. In the experimental system, the source of coherent light was a green laser (having wavelength of 532 nm). The laser output power was about 10 mW. An imaging optics of the camera was slightly defocused. The focal length of the optics that was used in the experiments was 50 mm and the distance from the laser to the subject's hand was about 50 cm. The camera captured images of the secondary speckle pattern from the wrist of the subject at rate of 350 frames per second (fps).

After extracting the speckle pattern in each frame, a spatial correlation between successive frames was performed as described in the above-indicated WO 2009/013738, which is incorporated herein by reference with respect to this specific functional step, to obtain a temporal change of the correlation function indicative of the change in the 2-D position of the speckle pattern's peak versus time.

Figure 6A:
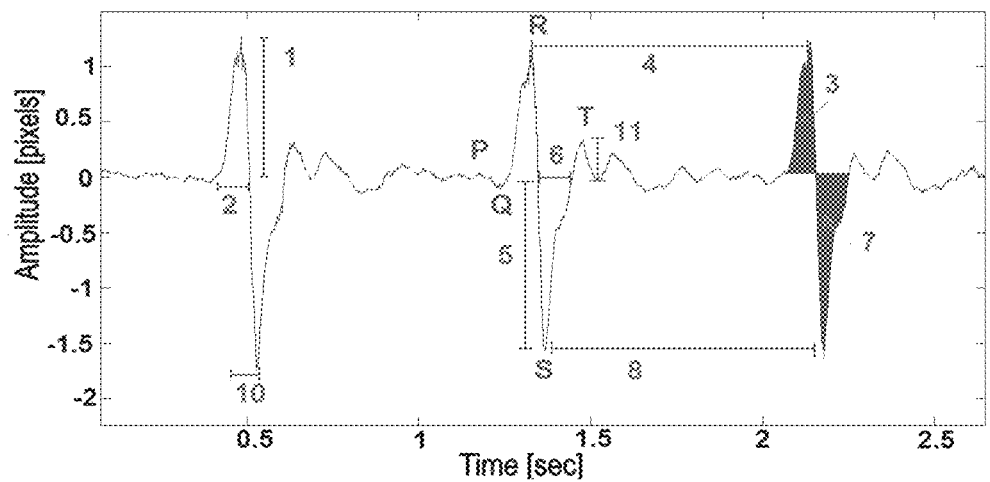
FIG. 6A is a graph exemplifying a function indicative of a time variation of the speckle pattern, as generated by the system of the present invention, and illustrating a plurality of parameters of the function in the time domain that can be used for determining the body conditions.

In FIG. 6A, a detected system output with high signal to noise ratio illustrates temporal change in the spatial correlation function indicative of the vibration profile of skin in a human wrist obtained in this experiment. The graph of FIG. 6A includes only several pulses, while in the experiment six pulses were taken into consideration and averaged. It can be seen that every pulse is shaped similarly to electrocardiogram (ECG) PQRST-type pulse. It contains a P pulse, QRS complex, and a T pulse. However, this is a function indicative of a mechanical vibration profile, rather than an electrical signal (as ECG), and therefore it corresponds to temporal information about vibration of blood vessels (proximal to the illuminated skin) due to blood flux pulsation.

In the experiment, the following parameters of the temporal change in the position of the peak of the spatial correlation function have been monitored: the main temporal peak amplitude (positive and negative) during one heart beat, temporal pulse width (positive and negative), temporal pulse profile energy (positive and negative separately), mean temporal distance between temporal peaks (gap or pulse rate), positive to negative temporal pulse peak ratio, temporal distance from positive to negative temporal peak, secondary temporal peak amplitude and main to secondary temporal peak amplitude ratio. These parameters are listed in Table 1 below, and the reference numerals in Table 1 refer to the numerals present in FIG. 6A.

TABLE 1

Parameters of the temporal change in the location of the peak of the spatial correlation function

| N | Parameter | Units | Comments |
|---|---|---|---|
| 1 | Positive pulse amplitude | Pixels | Refers to highest amplitude during one heart beat |
| 2 | Positive pulse width | Seconds | Estimated between 2 zero-crossing points |
| 3 | Positive pulse energy | (Pixels)$^2$ | Integral of the enclosed area in the positive pulse profile |
| 4 | Gap | Seconds | Number of frames between 2 peaks (pulse rate) |
| 5 | Negative pulse amplitude | Pixels | Refers to lowest negative amplitude during one heart beat |
| 6 | Negative pulse width | Seconds | Estimated between 2 zero-crossing points |
| 7 | Negative pulse energy | (Pixels)$^2$ | Integral of the enclosed area in the negative pulse profile |
| 8 | Negative gap | Seconds | Number of frames between 2 negative peaks |
| 9 | Amplitude radio | — | Absolute value of the ratio between the positive and the negative peaks |
| 10 | Peaks distance | Seconds | Number of frames between the positive and the negative peaks. |
| 11 | Secondary peak amplitude | Pixels | Refers to S point of QRS-complex |
| 12 | Main to secondary peak ratio | — | Absolute ratio between the main and the secondary peaks amplitude. |

In this experiment, several data sets, each indicative of temporal change of the spatial correlation function during a certain sampling period, were obtained by carrying out multiple timely separated sessions, each lasting over a certain time interval including a desired number of detectable pulses, just in order to use average values for the above parameters for each measurement session. The measurement sessions (coherent illumination and speckle pattern detection by pixel matrix) were applied to the same spot on the wrist. Before starting actual measurements, an individual hand template was constructed using gypsum, while a hole was drilled for each one of different subjects to allow the illumination of the subject's wrist. The diameter of the hole was slightly larger than the laser beam's diameter (approximately 1 cm). The test subjects of the experiment were four healthy subjects between the ages of 22 and 35 with different gender and weight. The summary of the subjects' personal information is listed in Table 2. All measurements were repeated several times to assure repeatability and correctness.

TABLE 2

| # | Gender | Age | Weight |
|---|--------|-----|--------|
| 1 | Female | 22  | 55     |
| 2 | Male   | 22  | 62     |
| 3 | Female | 24  | 44     |
| 4 | Male   | 35  | 90     |

In order to authenticate the required accuracy of 10-15% variation (as per standard glucometer) in the experiment results, the same spot on the wrist was illuminated over time, e.g. by multiple timely separated sessions. To ensure that this requirement was fulfilled, individual fixation devices were built for each subject's hand using gypsum, and several check tests were executed. In the check tests, the arm of each subject was inserted into the fixation device, the spot at which the skin pulsed because of the blood flow was marked, and a hole was drilled through each gypsum in the position of the chosen pulsating spot. Each subject then pulled his/her hand out of the gypsum and re-inserted it. Upon reinsertion, the marked spot was again aligned with the hole.

Figure 6B:
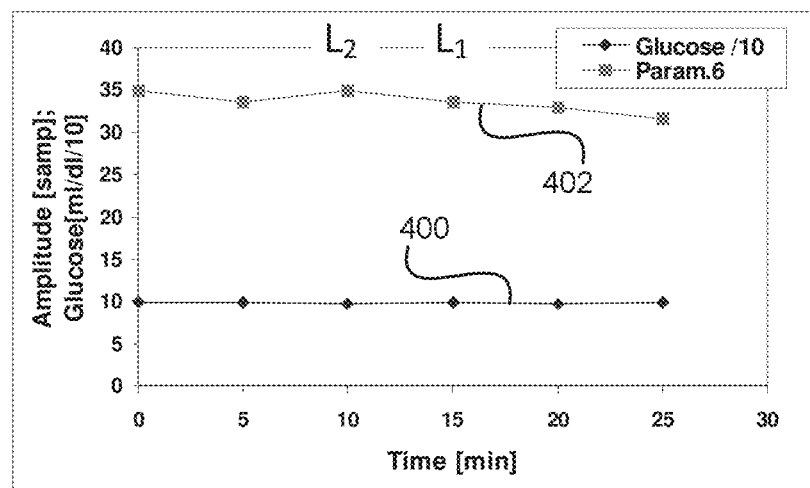
FIG. 6B is a graph which illustrates a test on a subject, in which a substantially constant level of blood glucose concentration was shown to correspond to a substantially constant negative pulse width (parameter 6 of FIG. 6A)
Figure 6C:
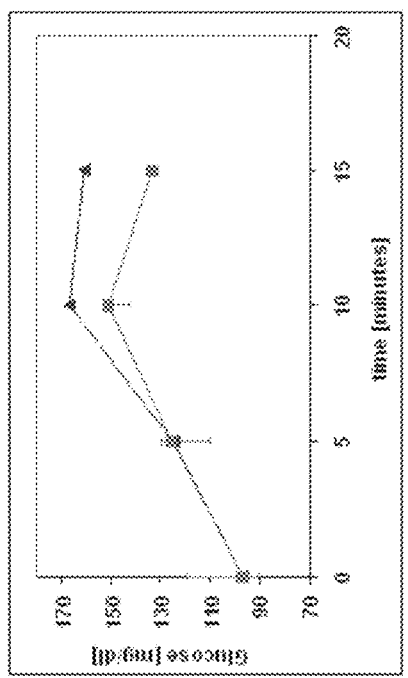
FIGS. 6C-6F are graphs illustrating the change in a test subject's blood glucose level and the corresponding change in the amplitude of positive peak (parameter 1 of FIG. 6A)
Figure 6D:
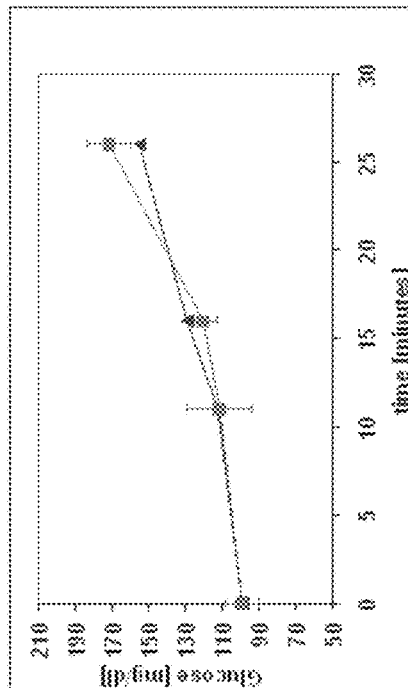
Figure 6E:
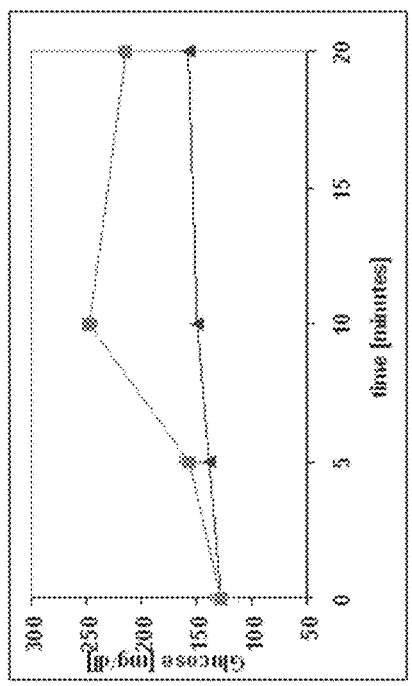
Figure 6F:
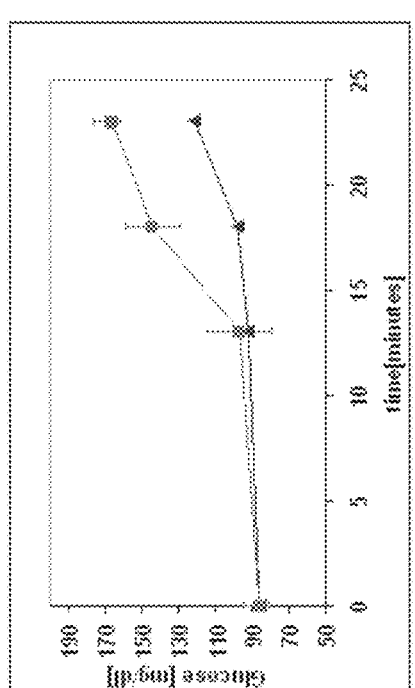

A second check test was aimed to check the stability of the gypsum fixation over time. Each subject inserted his/her hand into the fixation device and stayed fixed for approximately 30 minutes, while he/she was monitored by the system. The result of the second test is illustrated in FIG. 6B where the stability of the system can be clearly seen, since the measured values' results do not vary more than 15%. Substantially constant glucose concentration corresponded to substantially constant negative pulse width (parameter 6 of FIG. 6A) of the time variations in the position of the spatial correlation's function peak. Glucose concentration is shown by line $L_1$ in units of [ml/dl] divided by (representing a constant level of 100 [ml/dl]), while the parameter 6 is shown by line $L_1$. The units of parameter 6 are counted in time samples (each sample is 1/rate in time units).

After the preliminary check tests, the actual measurement was performed to relate parameters of the temporal changes in the position of the peak of the spatial correlation function to be indicative of the wrist's temporal pulse profile to glucose concentration in blood. To ensure that the glucose blood level would rise only as consequence of drinking of a sweetened beverage during the experiment, each examined subject preserved a fast for about 12 hours before the measurement took place. The expected values of blood glucose level for non-diabetic person after fasting falls to values range between 90 to 110 [mg/dl]. At the beginning of every experiment it was checked that the subject's blood glucose level was at this range, while later the subject received a sweetened drink and the level was changed.

The rate at which the concentration of glucose increases is different for each individual and depends on many personal parameters, such as body weight, metabolic rate, level of insulin in blood etc. The blood glucose level reached by the test subjects after drinking of about 400 ml of sweetened beverage (40K Cal) was in the range between 150 and 190 [mg/dL]. Each experiment lasted for 50-80 minutes, during it the measurements were carried out repeatedly every 5 minutes. Each 5 minutes sampling included capturing six subsequent video files of the illuminated spot and taking an accurate blood sample with a glucometer ("Accu-check") and manual blood pressure measurement using standard sphygmomanometer. All experiments showed that blood pressure did not change over the time of the experiment. It was important to check that blood pressure remained unchanged, in order to ensure that the expected change in the temporal pulse profile of the position of the speckle pattern's spatial correlation function's peak was indeed caused by glucose intake, rather than by blood pressure change.

A MATLAB program analyzed the videos and extracted the observed parameters from the files. Each file contained about 5 seconds of video samples at rate of 350 fps (frames per second), enabling the construction of data indicative of the temporal variation in position of the speckle pattern's spatial correlation function's peak, usually containing 6 temporal pulse peaks. Each peak was processed separately and the chosen parameters were extracted and averaged, therefore representing the average of approximately 30 peaks of pulse profile per each 5 minutes. For each parameter, the final graph of the estimated glucose level was produced. Joint graphs of the estimated and the reference glucose level for each one of the parameters and for each one of the subjects were created.

In the experiment, only the first samples of the estimated values were taken into account. These samples corresponded to the time period in which the glucose level was rising. These samples were more reliable due to two main reasons. First, glucose metabolism causes changes in biochemical levels of insulinotropic second messengers, including cyclic nucleotides, inositol phosphates, diacylglycerol and $Ca^{2+}$. These changes can also affect blood viscosity. The change in blood fluid viscosity due to biochemistry metabolism is not linear. Second, the test subjects could suffer from "exhaustion". More specifically, although the gypsum was reliable fixation, it was not attached "strongly" enough to the hand, and after approximately half an hour of testing, the subjects could produce spontaneous movement. Such spontaneous movement could have caused a change in the vibration profile not related to the actual glucose change.

The calculation include estimation of a correlation coefficient $C_{fg}$ (which is also called the value of the correlation peak) between optically extracted parameter of the and true glucose concentration obtained via the reference measurement. It is important to mention that this correlation coefficient is not related to correlation function between speckle patterns. Rather, this correlation coefficient is an estimate of the level of correlation between the optically extracted parameter (i.e. the parameter of the temporal change of the spatial correlation function) and the glucose concentration obtained via the reference measurement. A correlation coefficient approaching 1 or −1 is indicative of good correlation between the optically extracted parameter and the glucose concentration. If the correlation coefficient near 0, little or no correlation exists between the optically extracted parameter and the glucose concentration.

For two spatial functions g(x) and f(x) the correlation is defined as:

$$C_{fg}(x) = \int f(x')g^*(x'-x)dx' \quad (4)$$

And for discrete functions:

$$C_{fg}(m\delta x) = \sum_n f(n\delta x)g^*(n\delta x - m\delta x) \quad (5)$$

where δx is the spatial sampling interval and m is an integer number. The correlation coefficient or the value of the correlation peak equals to:

$$C_{fg}(0) = \sum_n f(n\delta x)g^*(n\delta x) \quad (6)$$

Note that the spatial coordinate is time varying and thus what one actually has is:

$$C_{fg}(x+k(t)) = \int f(x')g^*(x'-x-k(t))dx' \quad (7)$$

where k(t) is a time varying function. For discrete functions:

$$C_{fg}(m\delta x + k(t)) = \sum_n f(n\delta x)g^*(n\delta x - m\delta x - k(t)) \quad (8)$$

The correlation coefficient or the value of the correlation peak equals to:

$$C_{fg}(k(t)) = \sum_n f(n\delta x)g^*(n\delta x - k(t)) \quad (9)$$

Furthermore, an estimation of root mean square error (RMSE) was performed to quantify the relation between the reference measurement with conventional glucometer and the measured data obtained by the optical measurements of the invention, where:

$$RMSE = \sqrt{\sum_{i=1}^{N} \frac{(x_i - r_i)^2}{N}} \quad (10)$$

where $x_i$ is an i-th sample of the parameter values, $r_i$ is an i-th sample of the reference glucose measurements and N is the number of samples. The calculated samples were normalized to have energy of 1, before applying the RMSE estimator in order to obtain the common estimation scale for all parameters.

Dozens of experiments were executed with four test subjects in order to present a proof of principle validation. Initial results show a good correspondence of the estimated parameters with the positive slope of glucose level change in blood. Some of the obtained results are presented in the following figures.

In FIGS. 6C-6F, 7A-7D, 8A-8D, 9A-9D, 10Aa-10D the temporal evolution of the chosen parameters versus the reference measurement of glucose level taken by glucometer are shown. Glucose concentration in blood is denoted by the lines with triangles and the optically measured parameters from the pulse profile are denoted by the lines with squares.

The graph of the reference (glucose level) was obtained by using a conventional glucose meter device ("Acuu-check"). Error bars refer to standard deviation of positive and negative deviations separately, calculated over each 30 peak samples (per each point on the graph). Four different graphs on each figure refer to four different experiments taken with relevant subject on different days, during the morning hours while each subject preserved a fast of 12 hours. Values of the extracted parameters were linearly transformed to glucose level units according to the calibration done per each subject at the first measurement (time 0). Correlation and RMSE coefficients are shown below each graph.

The inventors have thus demonstrated that a strong correlation coefficient exists between the glucose blood concentration in the internal organ and attribute 1. Therefore, it is possible to establish a linear dependency between the amplitude of positive peak amplitude in the variation of the position of the correlation peak and the glucose blood concentration.

FIGS. 6C-6F are graphs illustrating the change in a test subject's blood glucose level and the corresponding change in the amplitude of positive peak (parameter/attribute 1 of FIG. 6A). FIGS. 7A-7D are graphs illustrating the change in a test subject's blood glucose level and the corresponding change in the ratio between positive and negative peak amplitudes (parameter 9 of FIG. 6A). FIGS. 8A-8D are graphs illustrating the change in a second test subject's blood glucose level and the corresponding change in the amplitude of positive peak (parameter 1 of FIG. 6A). FIGS. 9A-9D are graphs illustrating the change in a third test subject's blood glucose level and the corresponding change in the amplitude of positive peak (parameter 1 of FIG. 6A). FIGS. 10A-10D are graphs illustrating the change in a fourth test subject's blood glucose level and the corresponding change in the amplitude of positive peak (parameter 1 of FIG. 6A).

Figure 7A:
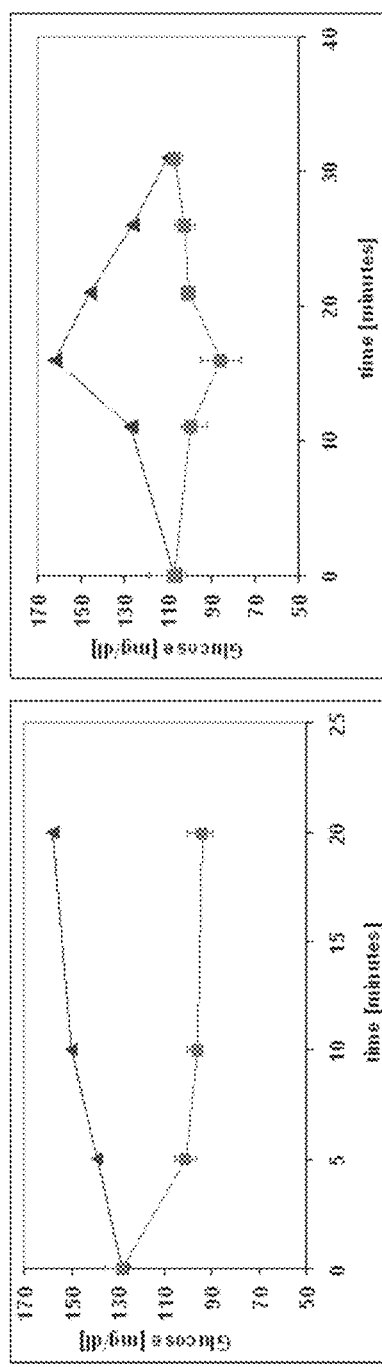
FIGS. 7A-7D are graphs illustrating the change in a test subject's blood glucose level and the corresponding change in the ratio between positive and negative peak (parameter 9 of FIG. 6A)
Figure 7B:
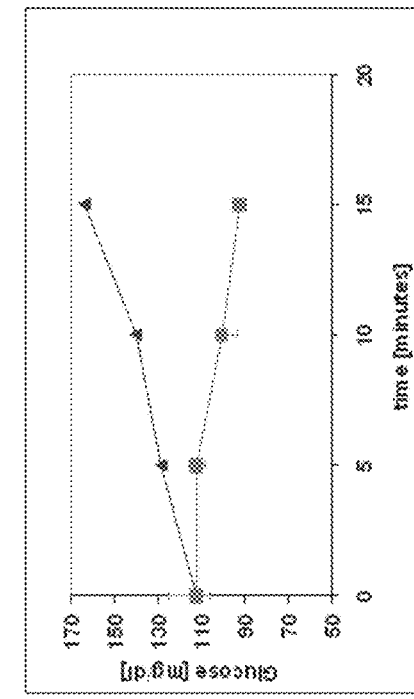
Figure 7C:
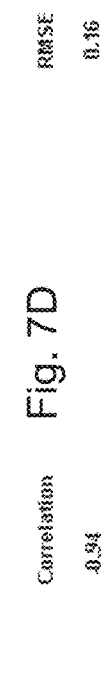
Figure 7D:
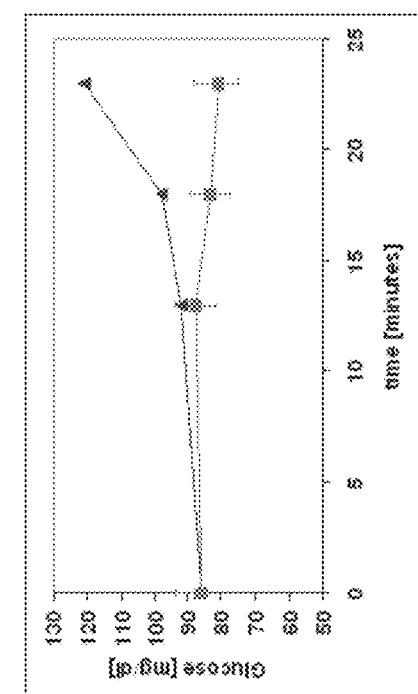
Figure 9A:
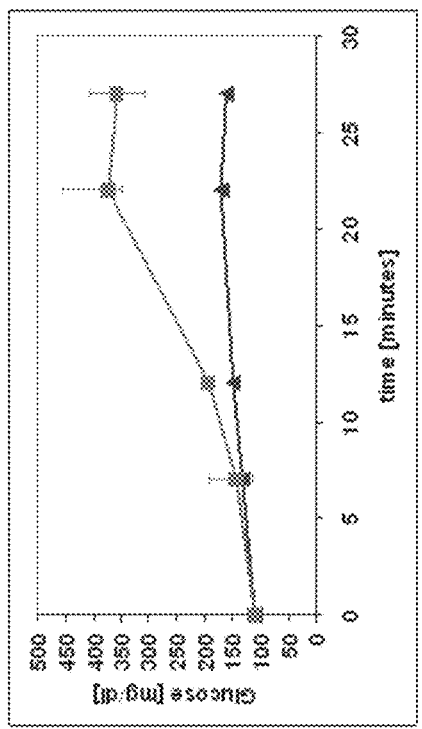
FIGS. 9A-9D are graphs illustrating the change in a third test subject's blood glucose level and the corresponding change in the amplitude of positive peak (parameter 1 of FIG. 6A)
Figure 9B:
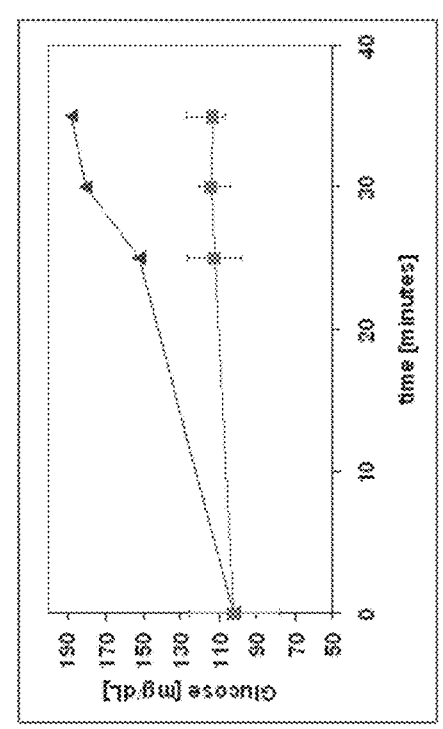
Figure 9C:
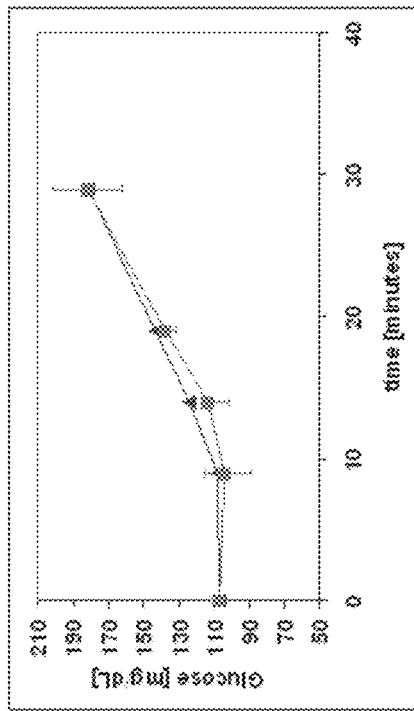
Figure 9D:
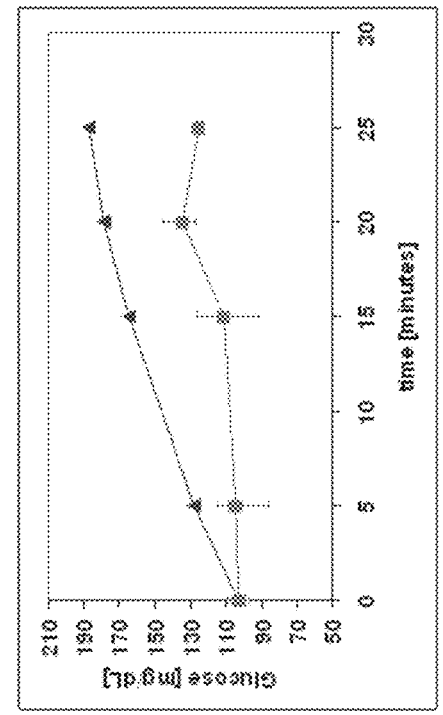

FIGS. 6C-6F refer to subject 1. The best correlative parameter for this subject was parameter 1. FIGS. 7A-7D show an exact inverse ratio between the reference glucose level and the value of parameter 9. Note that parameter 9 is actually a ratio between parameters 1 and 5. Some of the results showed very high correlation with the reference measurement for the full cycle of glucose changes in blood. In FIG. 7B it can be see that parameter 9 tracks the reference glucose level (in opposite direction). The time profile of parameter 9 includes areas in which the slope is positive and areas in which the slope is negative, thereby presenting a full cycle of increase and decrease of glucose level in the blood. A correlation coefficient of −0.916 was obtained between the two curves. RMSE estimator for this parameter was calculated between the inverse function of the normalized estimated parameter (one minus the normalized values) and the reference. RMSE estimator is equal to 0.17 in this case.

FIGS. 8A-8D refer to subject 2. The best correlative parameter for this subject was found to be positive pulse amplitude (parameter 1). FIGS. 9A-9D refer to subject 3. The best correlative parameter for this subject was found to be parameter 1 as well. FIGS. 10A-10D refer to subject 4, with the best correlative parameter 1.

Table 3 summarizes all correlation coefficients, while Table 4 summarizes all RMSE estimator coefficients from the graphs presented in FIGS. 6C-6F, 7A-7D, 8A-8D, 9A-9D, 10A-10D.

TABLE 3

|  | Parameter | Test 1 | Test 2 | Test 3 | Test 4 | Average |
|---|---|---|---|---|---|---|
| Subject #1 | Param. #1 | 0.862 | 0.945 | 0.91 | 0.964 | 0.92 |
|  | Param. #9 | −0.9 | −0.916 | −0.88 | −0.94 | −0.909 |
| Subject #2 | Param. #1 | 0.984 | 0.896 | 0.966 | 0.99 | 0.959 |
| Subject #3 | Param. #1 | 0.99 | 0.93 | 0.85 | 0.943 | 0.928 |
| Subject #4 | Param. #1 | 0.99 | 0.88 | 0.98 | 0.967 | 0.954 |

TABLE 4

|  | Parameter | Test 1 | Test 2 | Test 3 | Test 4 | Average |
|---|---|---|---|---|---|---|
| Subject #1 | Param. #1 | 0.205 | 0.17 | 0.19 | 0.12 | 0.171 |
|  | Param. #9 | 0.236 | 0.17 | 0.202 | 0.16 | 0.192 |
| Subject #2 | Param. #1 | 0.083 | 0.21 | 0.18 | 0.08 | 0.138 |
| Subject #3 | Param. #1 | 0.058 | 0.18 | 0.28 | 0.158 | 0.169 |
| Subject #4 | Param. #1 | 0.02 | 0.21 | 0.08 | 0.108 | 0.105 |

Thus, the technique of the present invention has been shown to provide an optical remote configuration for the estimation of glucose concentration in blood. The system of the present invention was tested with clinical trial group and the estimated results show a high correlation and low error comparing to reference measurement obtained by conventional invasive means.

With the technique of the present invention, it was demonstrated that at least one parameter extracted from data indicative of the temporal change of the spatial correlation function between speckle patterns obtained via measurements of speckle patterns generated from the wrist is proportional to the change of glucose concentration in blood. The technique of the present invention provides a non-invasive manner of remote measurement of glucose concentration in blood, while it uses only a low power emitting laser and a camera.

The following is the description of another embodiment of the invention, utilizing application of an external field to a region under optical measurements described above. This technique may be advantageously used for more accurate measurements of various parameters, such as glucose concentration, IOP, bone fractures.

Figure 11A:
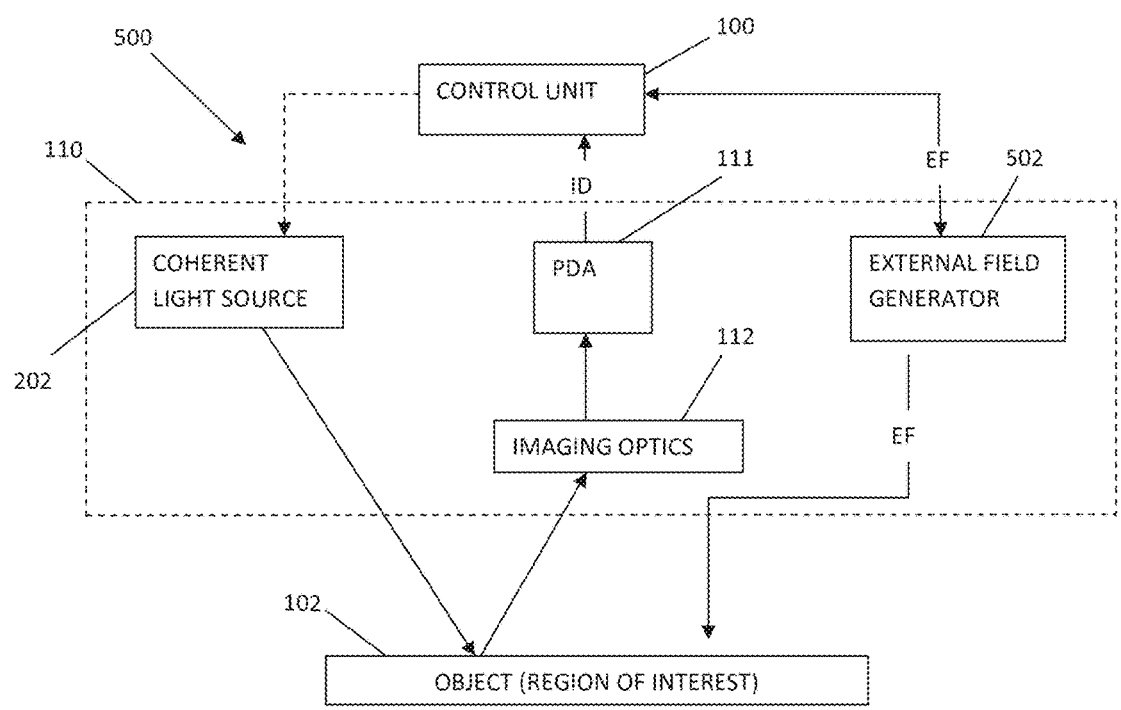
FIG. 11A is a schematic illustration of the system of the invention according to some other embodiments of the invention utilizing an external stimulator or vibration affecting unit.

In this connection, reference is made to FIG. 11A, illustrating, by way of a block diagram, a measurement system 500 of the invention for use in monitoring the subject's body condition(s). The system 500 is configured generally similar to the above-described systems 200 and 300, namely includes a measurement unit 110 and a control unit 100, but in which the measurement unit 110 includes an external field source 502 and the control unit is configured for receiving input data indicative of an external field EF generated by the unit 502 and for processing this data together with image data to determine one or more body conditions. Such a measurement system may be used in a medical device according to a specific application.

Thus, as shown in the figure, the measurement unit 110 includes a source of coherent light 202 (e.g. laser source); an imaging unit having a pixel detector array (PDA) 111 and an imaging optics (e.g. single lens) 112; and a field source generator unit 502. The control unit 100 is connectable via wires or wireless signal transmission (e.g. RF, IR, acoustic) to the output of the PDA 111 and to the unit 502, and in some applications the same or additional control unit may include an illumination controller for selecting appropriate wavelength(s) for illumination, as well as a controller for controlling the operation of unit 502, e.g. for modulating such field for example by varying its frequency as the case may be.

The source of coherent light 202 emits a light beam 104 to illuminate the object 102 (region of interest) during a certain time period (continuously or by multiple timely separated sessions), and concurrently the region of interest is subjected to a predetermined external field EF of a known parameter(s), e.g. field profile. This may be a magnetic field, or a pressure field (acoustic waves). As described above, the imaging unit focuses coherent light on a plane displaced from the object plane producing a defocused image of the object, and, because of the diffusive surface of the object, a secondary speckle pattern is generated being formed as the reflection/scattering of the coherent light beam from the object. The speckle pattern propagates toward the imaging optics 112 and is captured by the PDA 111, to generate output measured data. The applied external field affects the measured optical response of the region of interest. In some cases, e.g. when the applied field is an acoustic pressure field, the application of in such field affects the speckle pattern itself. In some other applications, e.g. when the applied field is a magnetic field, due to Faraday effect that it exhibits with the applied magnetic field the waveform (the spatial phase distribution) of the optical field is modified proportionally to the glucose concentration. Generally speaking, the change in the optical phase yields change in the speckle distribution which is time dependent due to the blood pulsation or due to the vibrations/motions generated with the external acoustic field.

Figure 11B:
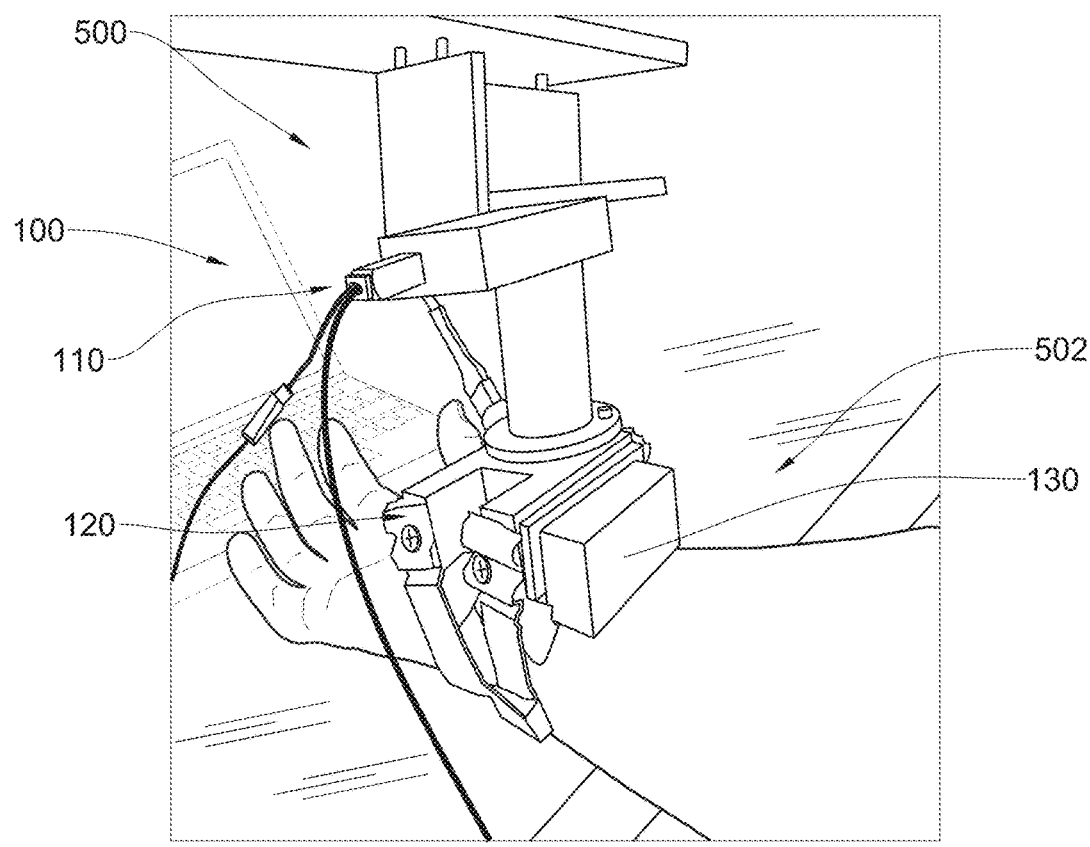
FIG. 11B illustrates an experimental setup presenting a specific example of the system of FIG. 11A comprises a magnetic field source.

FIG. 11B illustrates the experimental setup of the above-described system 500 configured for glucose level measurements. The experimental system is constructed generally similar to the above-described system of FIG. 11A, namely includes a measurement unit 110 (camera) and a control unit (computer) 100. In this example, the measurement unit 110 includes a magnetic field source 502 configured for applying a predetermined magnetic field to the region under measurements (i.e. under imaging). Also, in this example, the measurement unit is configured to illuminate a wrist of a subject. As shown in the figure, the measurement system is configured as a wrist-watch, i.e. is carried by bracelet-like holder 120 mountable on a patient's wrist.

Actually, such a single wristwatch device provides to extract different bio-medical parameters. The configuration and operation of system 500 is based on two optical approaches: the extraction and the separation of remote vibration sources, and the rotation of linearly polarized light by certain materials exposed to an external magnetic field. The technique is based on the tracking of temporal changes of reflected secondary speckles produced by wrist (region of interest) when being illuminated by a laser beam. Change in skin's temporal vibration profile together with change in the magnetic medium that is generated by time varied glucose concentration caused these temporal changes. Experimental tests for noncontact detection of bio-medical parameters, glucose and dehydration, showed good results in comparison to conventional reference measurements. The system of the invention, according to this embodiment, operates to observe the secondary speckle pattern that is created by illuminating the human skin near blood artery with a laser beam and a magnetic field that is created by a magnetic field source 502 (DC field (e.g. permanent magnet) or AC field source) attached to the apparatus. The speckle patterns are self-interference random patterns and movement that causes the speckle pattern to change as the interference affects the light waves. By using this technology, the skin's temporal movement can be tracked. From the blood flux pulsation various bio-parameters can be monitored. The magnetic field is necessary in order to create the Faraday effect which is the rotation of the plane of vibration of linearly polarized light when passing through a medium. Changing the polarization state of the wavefront results in a change of the detected speckle field.

As shown in FIG. 11B illustrating a specific not limiting example, the external field source 502 includes a magnet 130 placed between the patient's wrist and the measurement unit. This is in order to determine very small changes in the rotation produced by magneto-optic materials. The glucose exhibits the Faraday effect which is generated due to the circular structure of the glucose molecule. When a magnet is added to the setup (e.g., the bracelet-like design), the magnet generates magnetic field, and due to the Faraday effect there is a modification of the speckle pattern due to the existence of the glucose molecules. As other materials do not exhibit the Faraday effect, the change in the speckle pattern caused only due to the concentration of the glucose can be allocated. This yields much higher accuracy in the estimation of the glucose concentration.

The source of coherent light is a green laser (having wavelength of 532 nm). The laser output power is about 10 mW. An imaging optics of the camera is slightly defocused. The focal length of the optics that is used in the experiments is 50 mm and the distance from the laser to the subject's wrist is about 50 cm. The camera captured images of the secondary speckle pattern from the wrist of the subject at rate of 350 frames per second (fps). After extracting the speckle pattern in each frame, correlation was performed and the change in the 2-D position of the peak versus time was obtained. Every pulse is shaped similarly to ECG PQRST, in the experiment the average of five pulses was taken into account.

The inventors used MATLAB software product modified to a new factor which is the Faraday effect and its influence on the speckle field, to analyze the videos obtained from the camera and extract the observed parameters from the files. The algorithm analyzes the difference between two subsequent frames in means of lateral shift of speckle pattern using a correlation technique, therefore per one frame one value of the shift profile is produced. Once the vibration profile is obtained the pulsation shift peak is considered. In some cases the temporal change of the pulsation profile is analyzed. Each file contained about 5 seconds of video samples at rate of 545 fps (frames per second), usually containing 8 pulse peaks. Each peak is processed separately and the chosen parameters are extracted and averaged, therefore representing the average of approximately 30 peaks of pulse profile per each 5 minutes. The main measured parameter was the maximum pulse amplitude that refers to highest amplitude during one heart beat.

Figure 11C:
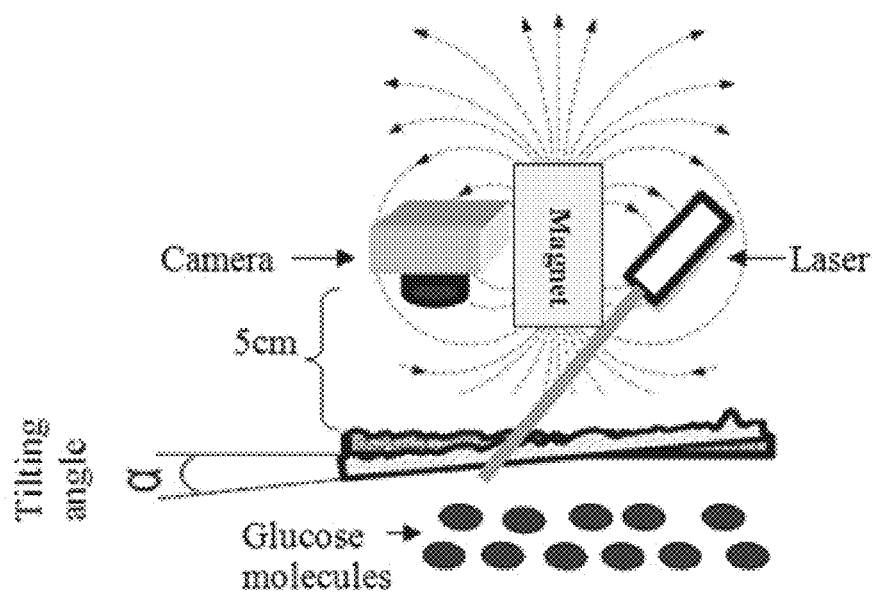
FIGS. 11C and 11D illustrate the operational principles of the system of FIG. 11A utilizing the magnetic field source.

The use of a magnet demonstrates the Faraday effect. In this connection, reference is made to FIG. 11C illustrating more specifically the operational principles of the system of FIG. 11A utilizing the magnetic field source 502.

The polarization rotation angle for light beam propagating through magneto-optic materials:

$$\theta = \vartheta BL = \pi L \Delta n(B)/\lambda_0 \quad (11)$$

where $\vartheta$ is Verdet constant, B is the magnetic field and L is the interaction length, $\lambda_0$ is the optical wavelength and $\Delta n$ is the difference in index of refraction between two circularly polarized states leading to the rotation. As known, the minimal magnetic field $B_{min}$ needed to de-correlate the speckle field is proportional to:

$$B_{min} \propto \pi L \theta R \quad (12)$$

where R is the radius of the illuminating beam and L is the interaction length. Eq. 12 defines the sensitivity of the proposed approach.

The temporal movement of the reflecting surface causes changes in the random speckle pattern over time. At first, a set of images as a function of time was captured. These sequential images are correlated in the second step. By calculating the correlation the relative movement of patterns can be extracted. This relative movement is obtained by allocating the time varying position of the correlation peak. The temporal movement of the human skin that is caused by the blood pulse stream is proportional to the relative shift of the speckle pattern:

$$\beta = \frac{4\pi \tan\alpha}{\lambda} \approx \frac{4\pi\alpha}{\lambda} \quad (13)$$

where $\beta$ is the change in the speckle pattern, $\alpha$ is the tilting angle of the illuminated surface (in our case, the human skin) and $\lambda$ is the wavelength (in our case, 532 nm).

The temporal change of glucose concentration $C_v(t)$ is proportional to the temporal change of $\beta(t)$:

$$C_v(t) \propto \beta(t) \quad (14)$$

Thus, the relative shift of the speckle pattern monitors the change of the temporal glucose concentration.

The importance of the application of the magnetic field is that it allows interaction with the glucose and not other materials because of the high Verdet constant that the glucose molecule has in contract to molecules of other materials in the blood stream.

Figure 11D:
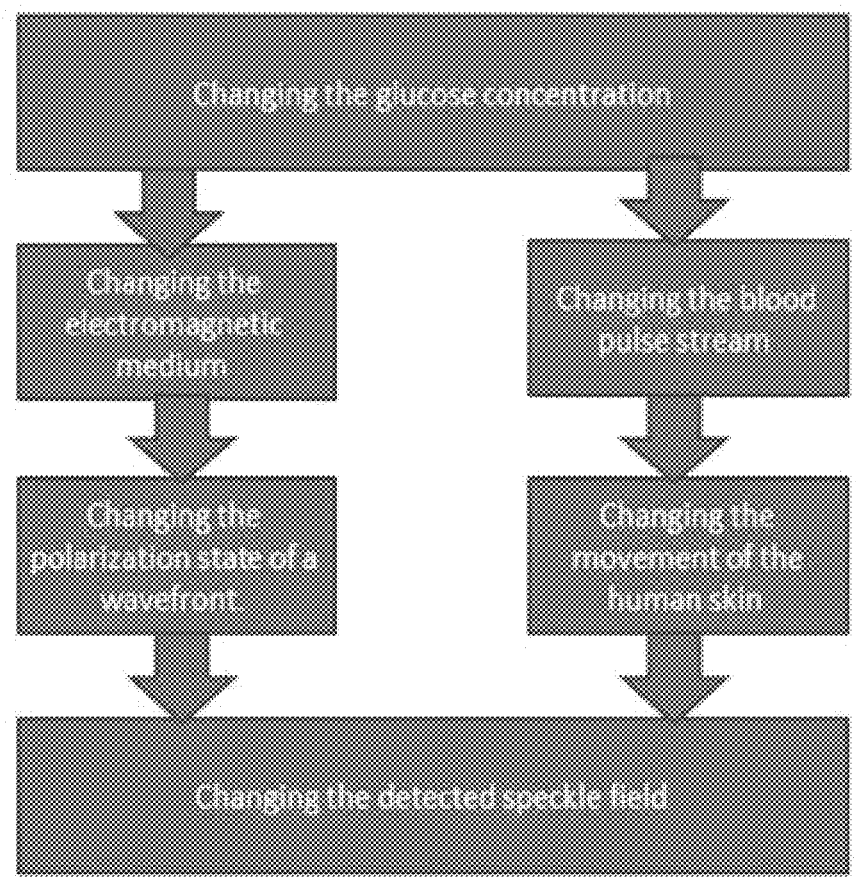

FIG. 11D illustrates a chart flow with the explanation of the contribution of the temporal movement of the skin and the Faraday effect to the speckle pattern change.

Figure 11E:
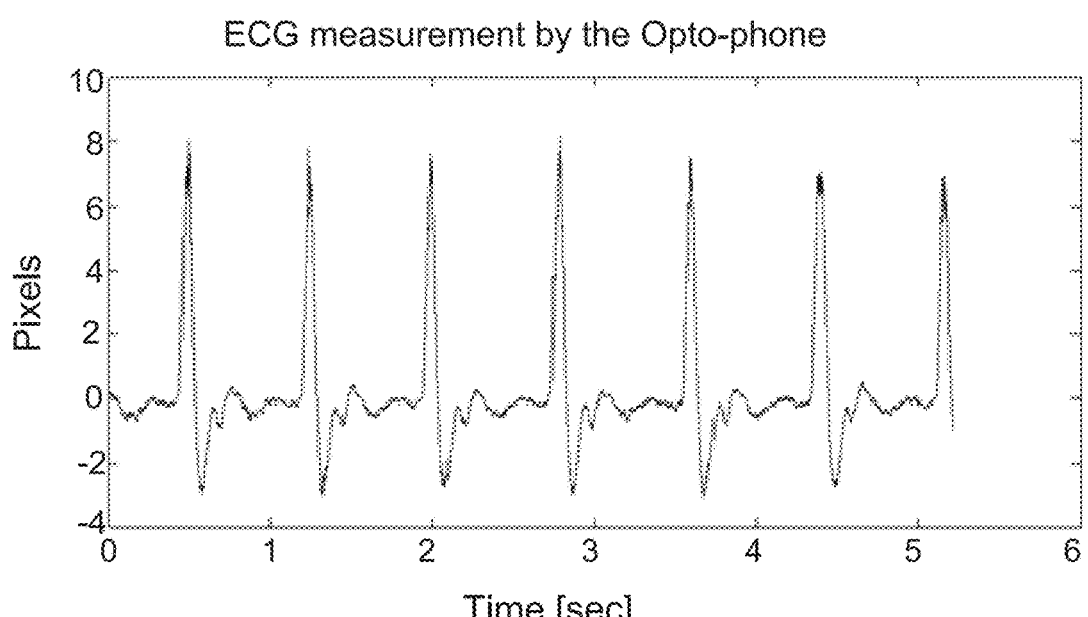
FIGS. 11E to 11I illustrate the experimental results for glucose concentration measurements using the setup of FIG. 11B in which the magnetic field source is exemplified as utilizing a permanent magnet.
Figure 11F:
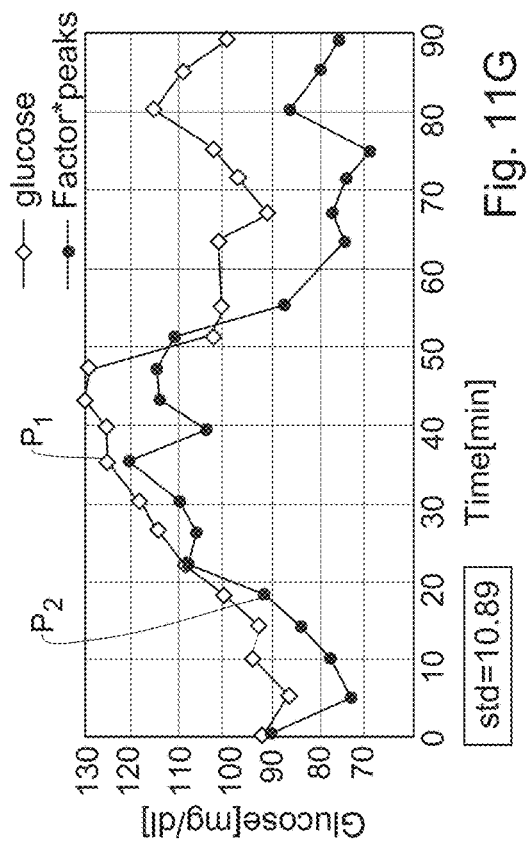
Figure 11G:
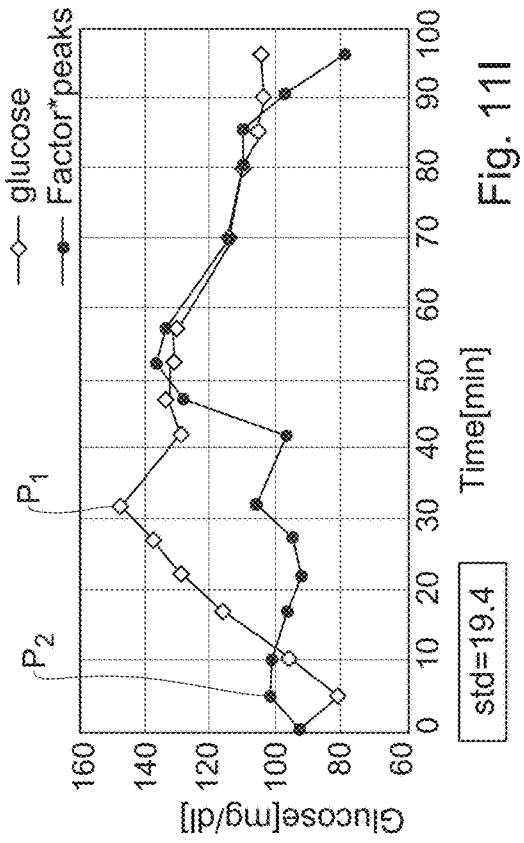
Figure 11H:
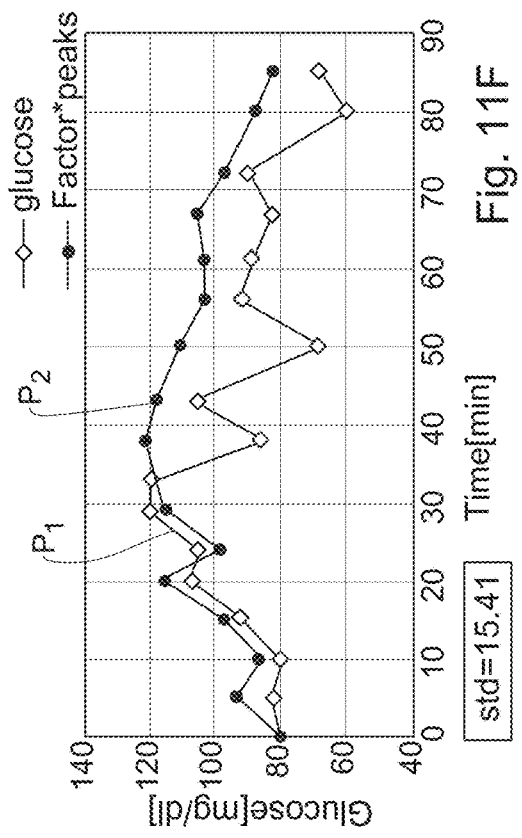
Figure 11I:
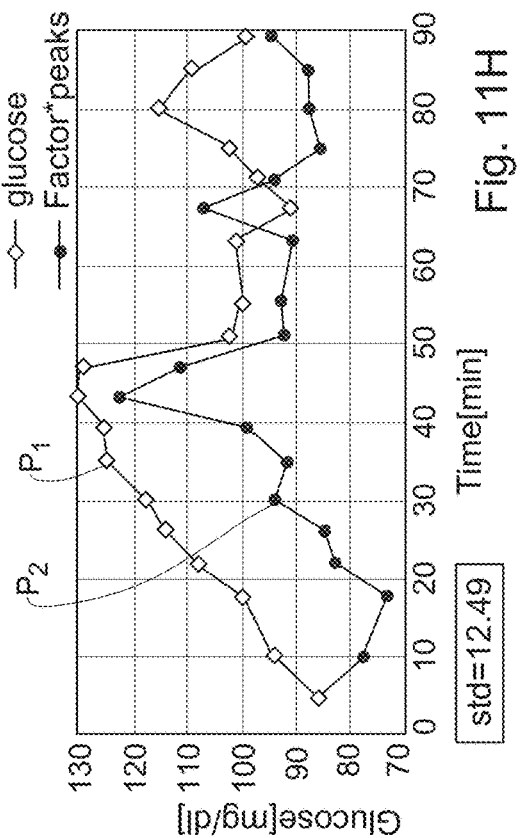

FIG. 11E shows one of the ECG measurements obtained by the bracelet-like setup with magnet shown in 11B, this graph is used us to monitor the glucose concentration and the dehydration level. A MATLAB software program was used that analyzed the videos obtained from the camera and extract the observed parameters from the files. Each file contained about 5 seconds of video samples at rate of 545 fps (frames per second), usually containing 8 pulse peaks. Each peak is processed separately and the chosen parameters are extracted and averaged, therefore representing the average of approximately 30 peaks of pulse profile per each 5 minutes. The main measured parameter was the maximum pulse amplitude that refers to highest amplitude during one heart beat.

To ensure that the glucose blood level would rise only as consequence of drinking of a sweetened beverage during the experiment, each examined subject preserved an overnight fast for about 12 hours before the measurement took place. The expected values of blood glucose level for non-diabetic person after fasting falls to values range between 90 to 110 [mg/dl]. At the beginning of every experiment, it was checked that the subject's blood glucose level was at this range, while later the subject received a sweetened drink and the level was changed.

The rate at which the concentration of glucose increases is different for each individual and depends on many personal parameters, like body weight, metabolic rate, level of insulin in blood, etc. The blood glucose level obtained after drinking of 500 ml of sweetened beverage (195 Cal) by the subjects was from 130 to 160 [mg/dL]. Each experiment lasted for 50-80 minutes, during it the measurements were carried out repeatedly every 5 minutes. Each 5 minutes sampling included capturing four subsequent video files of the illuminated spot and taking an accurate blood sample with a glucometer ("Accu-check") and manual blood pressure measurement using standard sphygmomanometer. All experiments showed that blood pressure have not been changed over the time of the experiment, which is important to check this point in order to ensure that the expected change in the pulse profile is indeed caused by glucose intake, rather than by blood pressure change.

FIGS. 11F-11I show glucose level in blood and the maximum amplitude peak Glucose level is denoted by curve $P_1$ (red) and the optically measured parameter is denoted by curve $P_2$ (blue). The graph of the reference (glucose level) was obtained by using a conventional glucose meter device ("Acuu-check"). Four different graphs refer to four different experiments taken on different days, during the morning hours while each subject preserved a fast of 12 hours. Estimated values were linearly transformed to glucose level units according to the calibration done per each subject at the first measurement (time 0). The standard deviation was measured between the optical measure of the invention to the reference. As shown, there is a tracking of the glucose level by the optically measured parameter, the optical measurement tracks up and falls down when the glucose return to the norm level.

In the above-described example with respect to the measurement system of FIGS. 11B and 11C, the applied magnetic field is a field generated by a permanent magnet. Accordingly, in this example, the portion of the correlation function with a higher amplitude is identified as corresponding to the glucose molecules' response, and used for processing and calculating the glucose concentration.

It should be noted that according to another example, the applied magnetic field may be an AC field, being temporally periodic stimulator. In this case, a Fourier transform of a temporal chart of the change in the position of the correlation peak is used to and extract a spectrum of the changes. Then, the amplitude value of the spectrum at the stimulation frequency of the external simulator (magnetic field) is examined.

Remote Optical Monitoring of Dehydration

Dehydration is a vital biomedical parameter that needs continuous monitoring. The reference for the dehydration level is the relative change of body weight. Water has numerous roles in the human body. It acts as a building material, a solvent, a reaction medium and reactant, a carrier for nutrients and waste products, in thermoregulation, and as a lubricant and shock absorber. The ability to monitor the dehydration level by remote optical measurement can be useful in the physical activity of athletes. Furthermore, dehydration can be a cause for delirium; contributing factor to dementia in the elderly and in the very ill. A high grade of dehydration is considered a risk factor for heat exhaustion and heat stroke.

Water is the main constituent of our body. There are more water molecules than any other molecule in the human body (about 60% of the body weight is water). At ambient comfort conditions (18-20 C.°) and low metabolic rate (rest to light exercise), water levels in the body are well regulated. When there is negative balance between fluid loss and fluid consumption dehydration ensue. It is customary to refer to dehydration in three levels of severity: mild, moderate, and severe. The signs and symptoms exacerbate from dry and sticky mouth, sleepiness or tiredness, to oliguria and anuria, delirium and unconsciousness. Severe cases of dehydration (>10%) can be fatal.

The inventors have demonstrated that the same measuring device (e.g. wearable device) that is used to monitor the glucose concentration in the blood stream can also be used to measure the dehydration level. As with the glucose, with the dehydration as well, preliminary clinical trials are done to validate the proposed operation principle.

In the experiments conducted by the inventors, water loss was estimated by weighing the subject before and after the experiment. The dehydration protocol consisted of sitting in a chamber with an inside temperature of 50° C. Every few minutes, the chamber was ventilated in order to prevent excessive heat absorbance and hyperthermia. During the heat exposure three OCG measurements were taken, with the bracelet device described above. The measurements were taken at three time points: 0 minutes, 40 minutes, and 70 minutes of exposure. Three healthy individuals were studied with the following characteristics:

| # | Gender | Age[Years] | Weight[kg] |
|---|--------|------------|------------|
| 1 | Male   | 22         | 95         |
| 2 | Male   | 28         | 75         |
| 3 | Male   | 47         | 84         |

The experiments have shown that even insignificant changes in the body's water balance can effectively be monitored.

The comparison of the same bio-medical parameter that was examined in the glucose study (refers to the highest amplitude during one heartbeat) can be applied to evaluate changes in body weight due to dehydration. In this case the weight is linearly transformed to the estimated values according to the calibration at the first measurement (time=0), and the weight of tested subjects was compared to the maximum amplitude peak measured by the optical device of the invention. For example, the subject's weight was 74.4 kg at the beginning of the experiment and 73.7 kg at the end of exposure. The peaks' pulse amplitude and the weight were calibrated to be 100%, and then the changes in weight to the changes in the optically measured parameter were compared. The big decrease in the optically measured parameter is an indication of the dehydration level in the subject.

The experiments have shown that multiple biomedical parameters can be measured simultaneously without interfering with each other. As described above, the same experimental setup of FIG. 11B was used by the inventors for measuring several different bio-chemical parameters including glucose concentration and de-hydration. It should be noted that in all experiments the subjects were healthy people and their blood pressure was measured throughout the experiment in order to make sure that indeed there is no other effect on β (see Eq. 13) rather than the change in the glucose concentration.

Figure 11J:
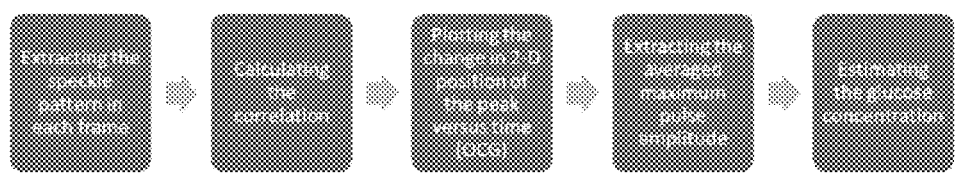
FIG. 11J exemplifies the steps of an algorithm of the invention for determining the glucose concentration.

FIG. 11J shows a chart flow exemplifying the algorithm used by the inventors for the monitoring of the glucose concentration and the dehydration level. The algorithm is mainly based upon doing correlation between the images of the speckle patterns in temporally adjacent frames and checking the movement in the position of the obtained correlation peak.

It should be noted that the measurement results are more accurate for the glucose concentration when using the application of the magnetic field, because Faraday effect induced by the glucose molecules subjected to the magnetic field affects/modifies the spatial phase distribution of the optical field proportionally to the glucose concentration. The change in the optical phase yields change in the speckle distribution which is time dependent due to the blood pulsation.

Blood Alcohol Concentration

The following section refers to tests conducted by the inventors on human subjects, in order to determine a relationship between blood alcohol concentration and one or more parameters of the temporal changes in a feature (e.g. the correlation peak and/or its value) of the speckle pattern's spatial correlation function in the time domain.

The tests were conducted with an experimental system generally similar to that of FIG. 1B, designed as the above described bracelet-like setup. The experimental system included only a green laser to illuminate the inspected object (to generate the secondary reflected speckle) and a defocused camera connected to a computer (control unit) that observes the secondary speckle pattern reflected from the wrist of the subject. The distance from the laser to the subject's wrist was about 10 cm. In all of the experiments, the sampling rate of the camera was 405 FPS (frame per second). The coherent light emitter was a green CW (continuous wave) laser at a wavelength of 532 nm at an approximate power of 100 mW. The laser beam incidence angle was chosen to be 75 degrees relative to the subject's wrist.

During the measurements, each test subject was tested simultaneously by the experimental system and by a conventional alcohol breathing measurement device to get a reliable reference. A BAC calculator was also used to get a secondary reference.

The samples taken during the tests were in the form of an AVI file (video file) that shows the speckles pattern through time. By using 'MATLAB' program with an image processing techniques, the inventors located the position of the 2-D speckles pattern at each frame. The Matlab program first removed background static noise by comparing the adjacent frames, then analyzed the shift in the speckles between adjacent frames to create data indicative of the skin (and therefore vascular) movement.

More specifically, a spatial correlation function between speckle patterns in adjacent frames was determined. Then, the X and Y coordinates of the position of the spatial correlation function's peak were plotted for each frame, and the shift of such peak between adjacent frames was determined, to create a time-varying function indicative of the temporal change of the spatial correlation function, and of the skin (and therefore vascular) movement. The plots were analyzed and several parameters were extracted from the time-varying function. The parameters of the time-varying function included the main peak amplitude, distance between two nearby peaks, ratio between main and secondary peaks amplitude, etc. A total of 19 different parameters were extracted. Every AVI file provided six different temporal pulses and also the average values of the parameters of the six pulses. All this data was plotted as an excel output data table. Each time, five samples of each test were taken and averaged.

This procedure was repeated approximately each 5-7 minutes throughout a period of 35 minutes. Five different experiments were conducted on five subjects. All of the subjects were healthy, average drinkers with average body weight (four males and one female). The first measurement was at time zero, before starting drinking alcohol. Thereafter, the subjects drank known amounts of highly alcoholic beverage and the subjects' vascular behavior was examined. Every measurement by the experimental setup was followed by a breath test, to be used as a reference.

In a second battery of tests, five subjects were tested for a long duration (75 min when taking samples every 15 minutes).

Throughout the duration of the each experiment, each of the subjects was seated in front of the experimental system, while his wrist was illuminated by the laser beam. The arm of each test subject was tied and fixed to the system, in order to ensure that the subject's pulse would not be affected by any other external variables (such as involuntary movement) and thereby to increase of the accuracy of the measurements.

Figure 12A:
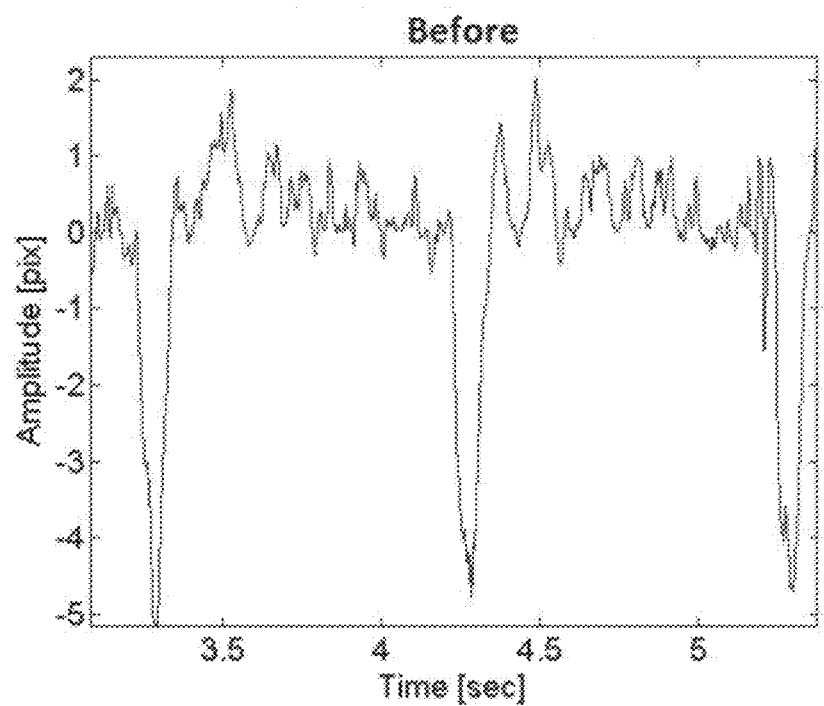
FIGS. 12A-12B are graphs illustrating different functions indicative of a change in the speckle pattern over time generated by the system of the present invention, based on measurements before and after alcohol consumption.
Figure 12B:
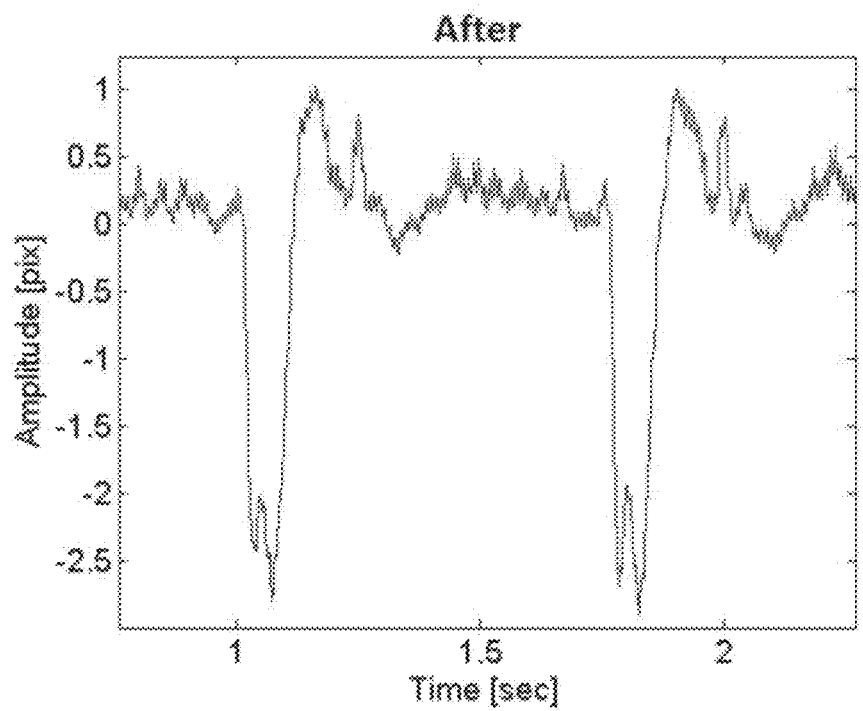

Referring to FIGS. 12A-12B, there are shown different time-varying functions indicative of time changes in the position of the speckle pattern (due to a motion of skin on a human wrist) as generated by the system of the present invention, based on measurements before alcohol consumption (FIG. 12A) and after alcohol consumption (FIG. 12B).

After collecting and analyzing all the results, five parameters which were the most relevant to the experiment were selected. According to scientific studies, alcohol takes time to be absorbed (unlike other materials, like glucose, for example). It was therefore decided that a suitable manner to examine the result is by two time settings: before the alcohol consumption and after half an hour. This is because, according to scientific studies, the maximum alcohol level is reached between half an hour to hour following the ingestion of alcohol. Thereafter, the alcohol level decreases. The selected parameters were: Pulse size, Negative pulse size, peak distance (Peakdis), ratio between main and secondary peak positions (Ratio wid), and ratio between main and secondary peak amplitudes (Main sec peak ratio). These parameters will be illustrated in the figures below. Another test was used as a reference, to measure the parameters of subjects that did not consume alcohol at all. Table 5 shows the relevant details about the test subjects.

TABLE 5

|  | Age | Gender | Weight | Alcohol consumption in the experiment [ml] | BAC |
|---|---|---|---|---|---|
| subject 1 | 28 | Male | 75 | 80 | 0.0524 |
| subject 2 | 28 | Male | 61 | 80 | 0.0644 |
| subject 3 | 21 | Male | 82 | 160 | 0.0958 |
| subject 4 | 21 | Male | 78 | 160 | 0.1008 |
| subject 5 | 25 | Male | 70 | 160 | 0.1123 |

Figure 13:
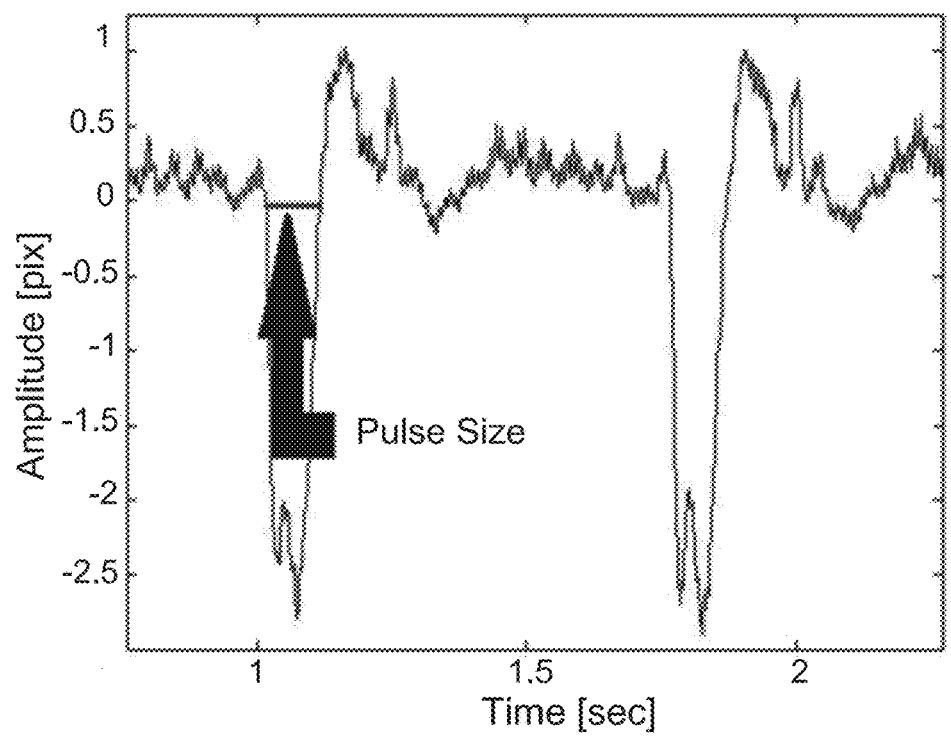
FIG. 13 is a graph illustrating the pulse size (width) of the function indicative of skin vibration.
Figure 14A:
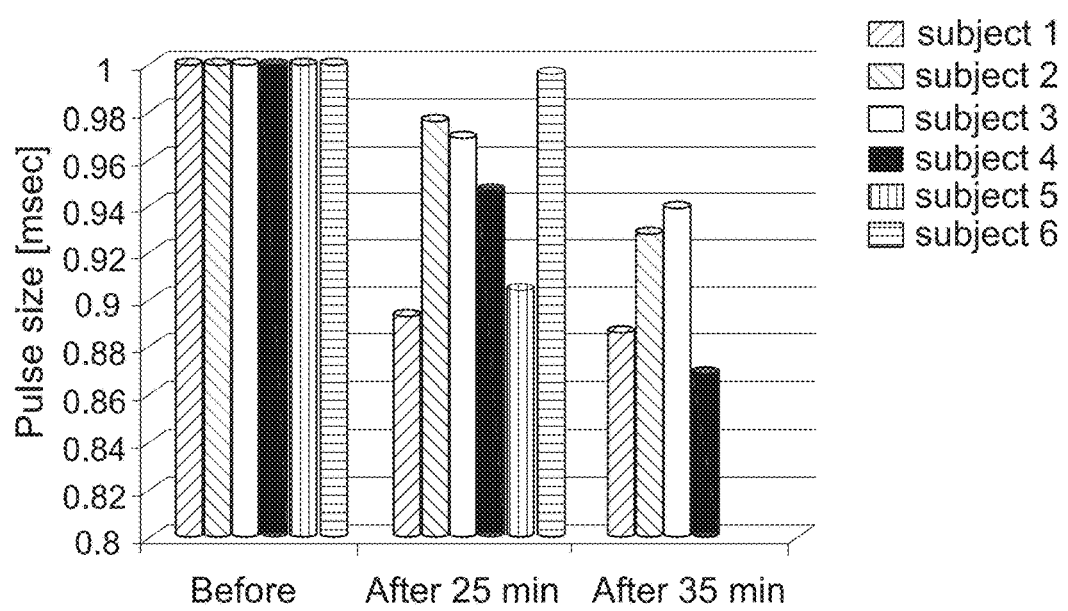
FIGS. 14A-14B are graphs illustrating the change of test subjects' pulse sizes over time, as a consequence of alcohol consumption.
Figure 14B:
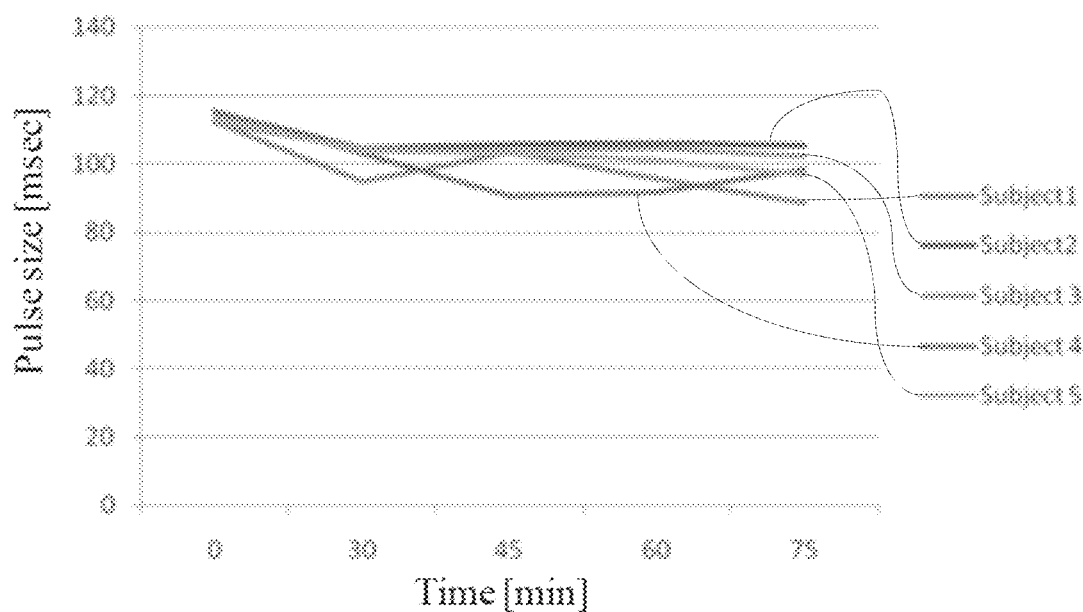

Referring to FIG. 13, the pulse size in a function describing temporal changes in the position of the peak of the spatial correlation function (is the function being indicative of the skin vibration profile in the time domain) is illustrated. FIGS. 14A-14B are graphs illustrating the change of test subjects' pulse sizes over time, as a consequence of alcohol consumption.

The pulse size is the width of the main pulse at the level at which the shift's amplitude is zero. The units of this parameter are milliseconds. The pulse size is the amount of time that the outer layers of the blood vessels are subjected to the largest shift.

Table 6 summarizes values the of pulse size before drinking alcohol and after significant time (25 min & 35 min). Table 7 summarizes the values of the pulse size in the long duration test, where measurements were taken before drinking alcohol and every 15 min thereafter (for 75 min).

TABLE 6

|  | Before | After 25 min | After 35 min |
|---|---|---|---|
| subject 1 | 121.481 | 108.477 | 107.737 |
| subject 2 | 102.551 | 100.049 | 95.185 |
| subject 3 | 116.049 | 112.428 | 109.053 |
| subject 4 | 135.852 | 128.642 | 118.025 |
| subject 5 | 109.037 | 98.663 | — |
| reference | 111.501 | 111.111 | |

TABLE 7

|  | 0 | 30 min | 45 min | 60 min | 75 min |
|---|---|---|---|---|---|
| subject 1 | 112.4848 | 94.66667 | 103.4921 | 95.7193 | 88.5614 |
| subject 2 | 115.0222 | 104.7111 | 105.6667 | 106.2667 | 105.2222 |
| subject 3 | 112 | 104.475 | 103.6875 | 104.4231 | 102.2 |
| subject 4 | 115.4211 | 103.0909 | 90.63158 | 91.58824 | 98.5 |
| subject 5 | 113.4868 | 103.6364 | 103.125 | 101.25 | 96.90789 |

The data of tables 6 and 7 is shown graphically in FIGS. 14A and 14B, respectively.

It can be seen see that there is constant and prominently visible decrease in the pulse duration, that shows "sharper" (shorter) movement of the pulse. This decrease in the pulse duration can be indicative of a high blood alcohol concentration.

Figure 15:
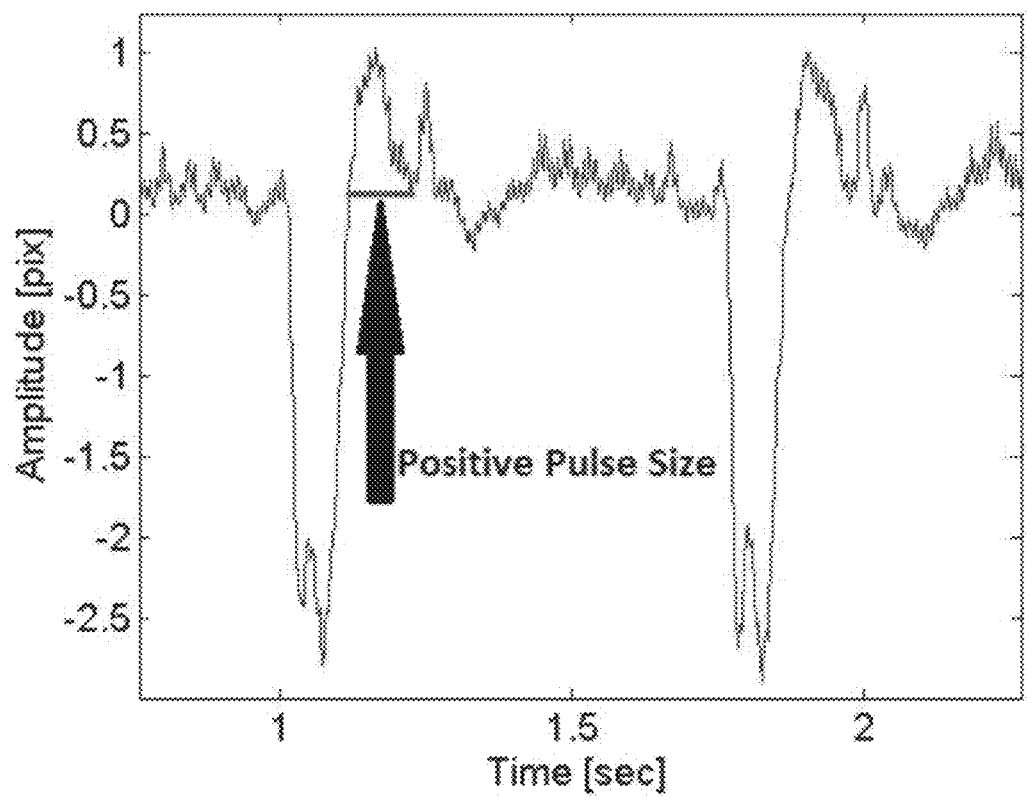
FIG. 15 is a graph illustrating the positive pulse size of the function indicative of skin vibration profile in the time domain.
Figure 16A:
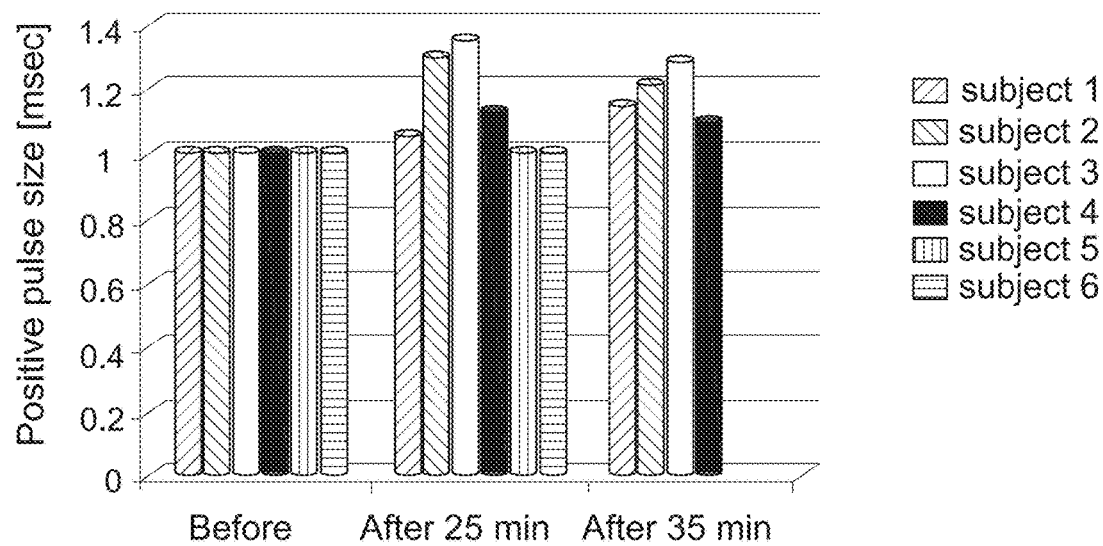
FIGS. 16A-16B are graphs illustrating the change of test subjects' positive pulse sizes over time, as a consequence of alcohol consumption.
Figure 16B:
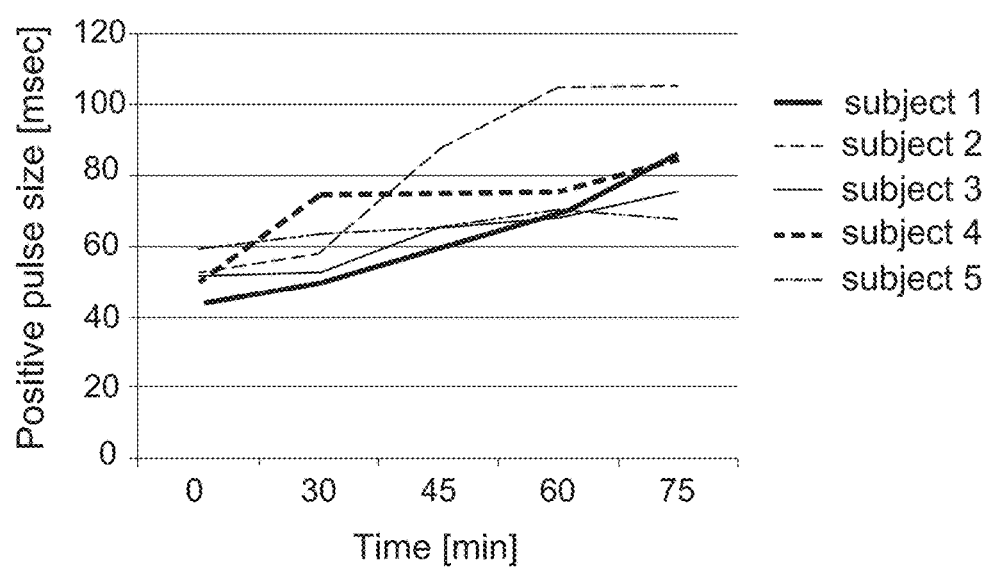

Referring to FIG. 15, the positive pulse size in a function describing the temporal variations in the position of the spatial correlation function's peak is illustrated. FIGS. 16A-16B are graphs illustrating the change of test subjects' positive pulse sizes over time, as a consequence of alcohol consumption.

The positive pulse size is the width of the positive pulse (relative to the main peak) at the level at which the shift's amplitude is zero. The units of this parameter are milliseconds.

Table 8 summarizes values the of positive pulse size before drinking alcohol and after significant time (25 min & 35 min). Table 9 summarizes the values of the pulse size in the long duration test, where measurements were taken before drinking alcohol and every 15 min thereafter (for 75 min).

TABLE 8

|  | Before | After 25 min | After 35 min |
|---|---|---|---|
| subject 1 | 167.737 | 176.675 | 192.428 |
| subject 2 | 148.189 | 192.741 | 179.704 |
| subject 3 | 134.140 | 181.152 | 172.016 |
| subject 4 | 84.864 | 99.827 | 99.580 |
| subject 5 | 104.938 | 118.765 | 115.136 |
| reference | 158.951 | 152.910 | |

TABLE 9

|  | 0 | 30 min | 45 min | 60 min | 75 min |
|---|---|---|---|---|---|
| subject 1 | 52.13333 | 58.66667 | 87.53846 | 104.9333 | 105.7143 |
| subject 2 | 59.07692 | 63.54545 | 65.40741 | 70.18182 | 67.90476 |
| subject 3 | 51.42857 | 52.92308 | 65.14286 | 68.34783 | 75.46667 |
| subject 4 | 50.36364 | 74.66667 | 75.17647 | 75.47368 | 84.5 |
| subject 5 | 44.2 | 50 | 59.15789 | 68.76923 | 85.89474 |

The data of tables 8 and 9 is shown graphically in FIGS. 16A and 16B, respectively.

It can be seen that there is constant and prominently visible increase in the pulse duration. This shows "dull" movement of the positive pulse, a behavior opposite to that of the main pulse.

Figure 17:
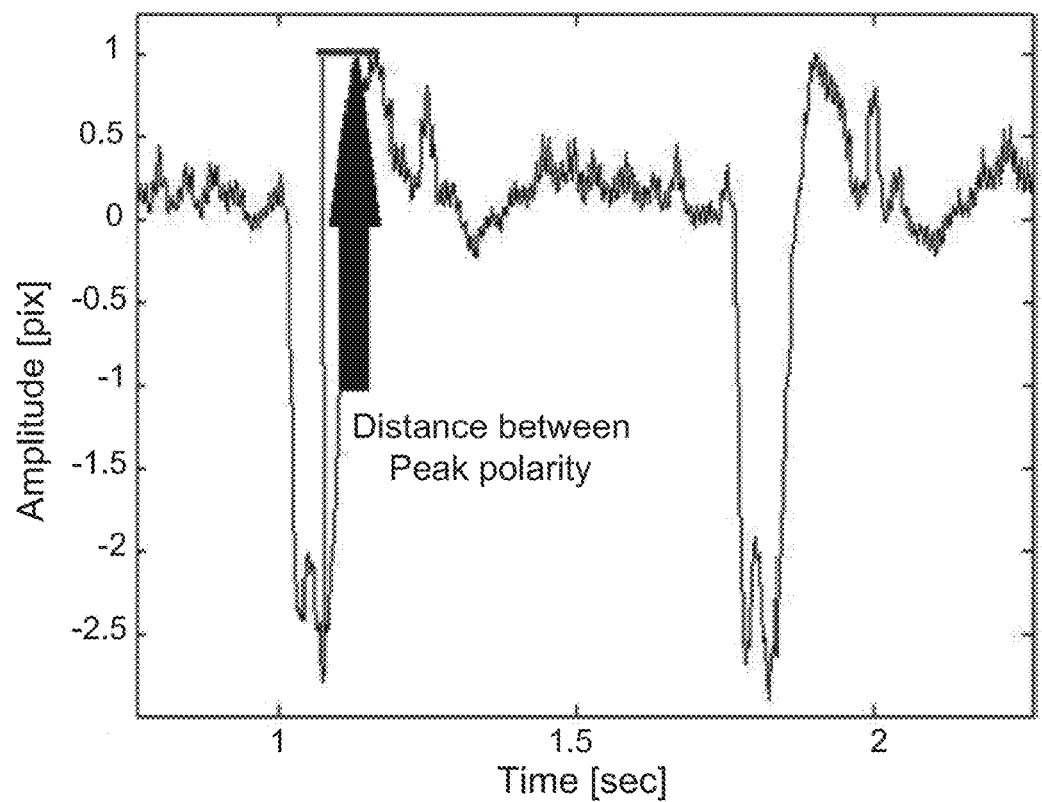
FIG. 17 is a graph illustrating the distance between peak polarities of the function indicative of skin vibration profile in the time domain.
Figure 18A:
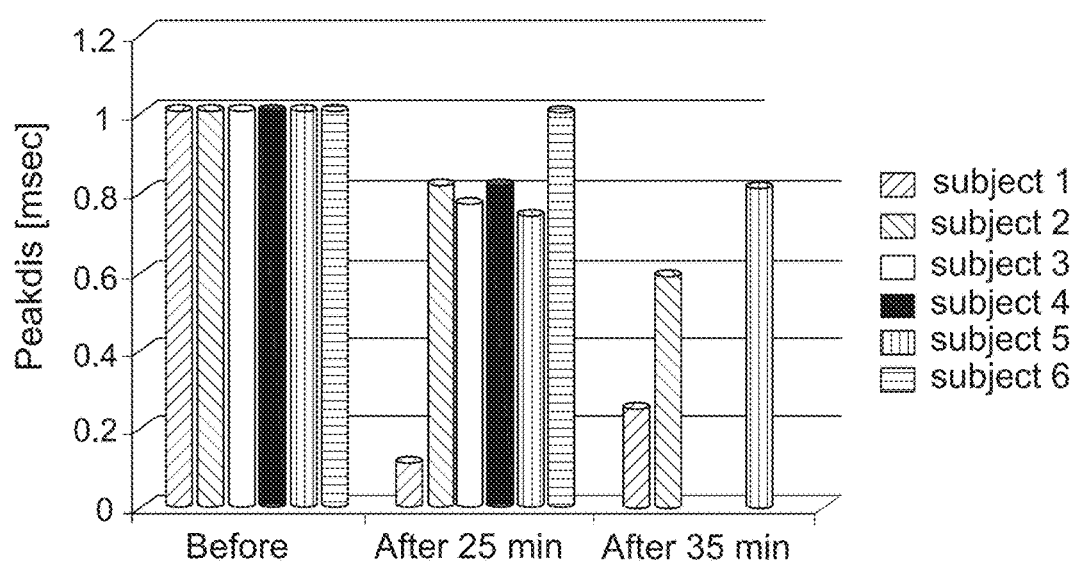
FIGS. 18A-18B are graphs illustrating the change of test subjects' distances between peak polarities over time, as a consequence of alcohol consumption.
Figure 18B:
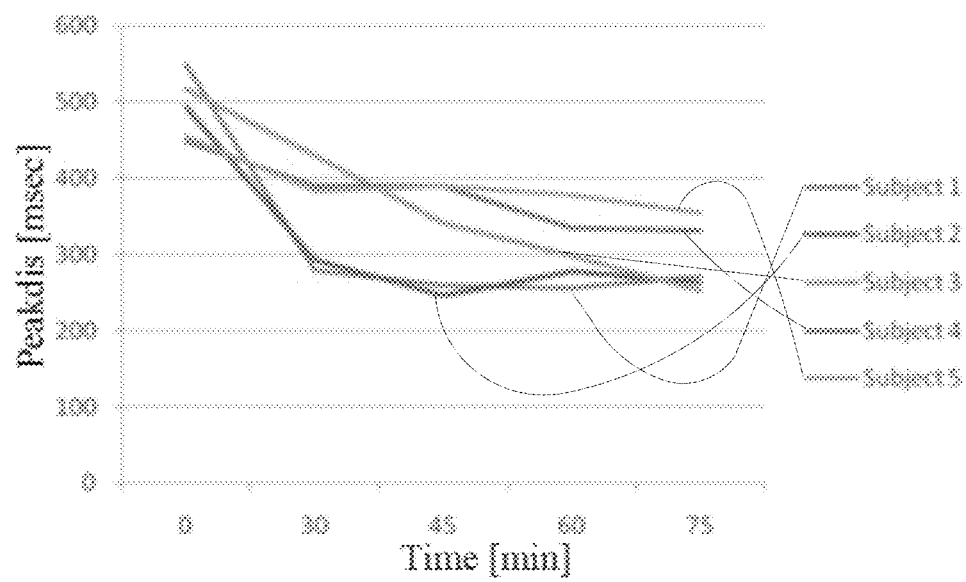

Referring to FIG. 17, the distance between peak polarities in a function describing the temporal variations of the position of the spatial correlation function's peak is illustrated. FIGS. 18A-18B are graphs illustrating the change of test subjects' distances between peak polarities over time, as a consequence of alcohol consumption.

The distance between peak polarities (also referred to as "peakdis") is the time in which the blood vessels moves from the maximum peak to the minimum peak or vice versa. This parameter is measured in milliseconds.

Table 10 summarizes values of the distance between peak polarities before drinking alcohol and after significant time (25 min & 35 min). Table 11 summarizes the values of the distance between peak polarities in the long duration test, where measurements were taken before drinking alcohol and every 15 min thereafter (for 75 min).

TABLE 10

|  | Before | After 25 min | After 35 min |
|---|---|---|---|
| subject 1 | 829.037 | 93.844 | 205.794 |
| subject 2 | 343.160 | 282.272 | 200.296 |
| subject 3 | 479.490 | 368.971 | — |
| subject 4 | 677.152 | 555.473 | — |
| subject 5 | 701.563 | 519.901 | 567.901 |
| reference | 643.062 | 644.170 | |

TABLE 11

|  | 0 | 30 min | 45 min | 60 min | 75 min |
|---|---|---|---|---|---|
| subject 1 | 493.575 | 292.2 | 246.7273 | 277.7143 | 263.5714 |
| subject 2 | 548.7273 | 279.5833 | 258.8 | 256.6 | 271.4118 |
| subject 3 | 517.5333 | 429.1583 | 341.3083 | 298.4333 | 253.4583 |
| subject 4 | 448.2917 | 390.0658 | 390.0658 | 334.0167 | 332.0882 |
| subject 5 | 454.1429 | 383.625 | 390 | 378.5556 | 355.2174 |

The data of tables 10 and 11 is shown graphically in FIGS. 17A and 17B, respectively.

It can be seen that there is a prominent decrease in the time in which the blood vessel jumps from max peak to the minimum peak.

Figure 19:
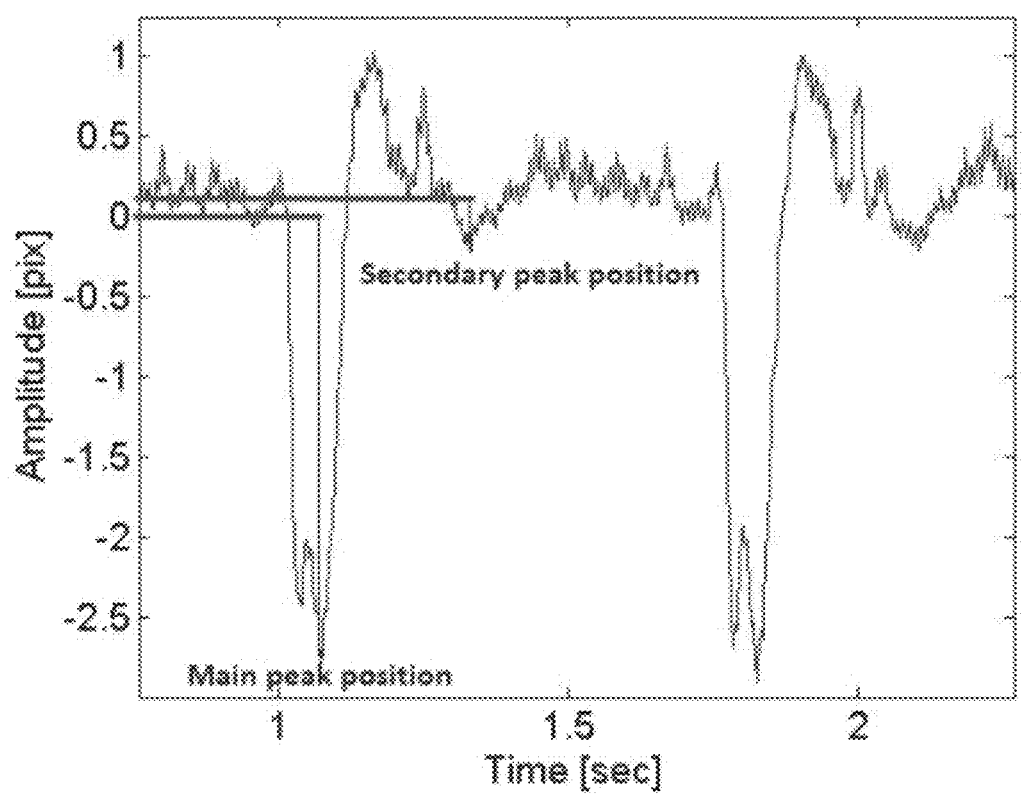
FIG. 19 is a graph illustrating the main and secondary peak positions in the function indicative of skin vibration profile in the time domain.
Figure 20A:
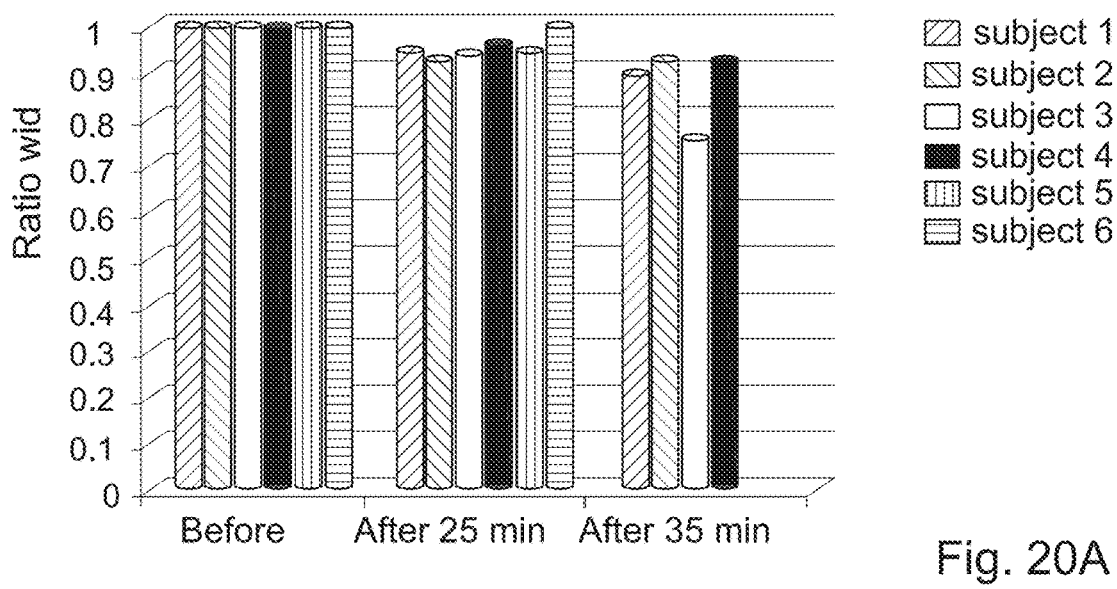
FIGS. 20A-20B are graphs illustrating the change of test subjects' ratios between main and secondary peak positions, as a consequence of alcohol consumption.
Figure 20B:
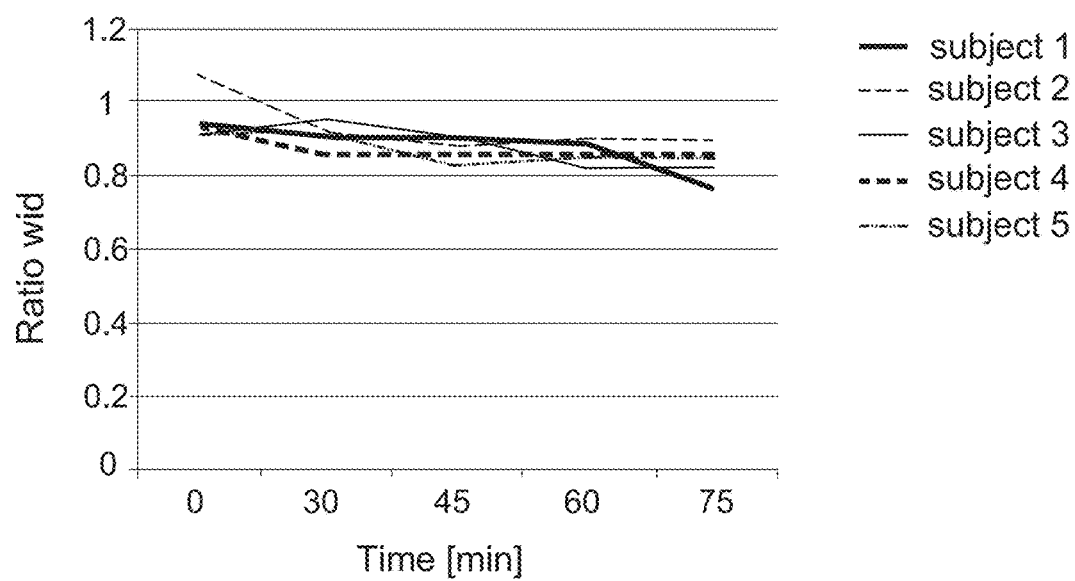

Referring to FIG. 19, the main and secondary peak positions in a function describing the temporal variations of the position of the peak of the spatial correlation function are shown. FIGS. 20A-20B are graphs illustrating the change of test subjects' ratios between main and secondary peak positions, as a consequence of alcohol consumption. The ratio between the main and the secondary peak position is without units.

Table 12 summarizes values of ratios between main and secondary peak positions before drinking alcohol and after significant time (25 min & 35 min). Table 13 summarizes the values of ratios between main and secondary peak positions in the long duration test, where measurements were taken before drinking alcohol and every 15 min thereafter (for 75 min). The data of tables 12 and 13 is shown graphically in FIGS. 19A and 19B, respectively.

TABLE 12

|  | Before | After 25 min | After 35 min |
|---|---|---|---|
| subject 1 | 0.93 | 0.88 | 0.83 |
| subject 2 | 0.93 | 0.86 | 0.86 |

TABLE 12-continued

|  | Before | After 25 min | After 35 min |
|---|---|---|---|
| subject 3 | 0.94 | 0.88 | 0.71 |
| subject 4 | 0.94 | 0.90 | 0.87 |
| subject 5 | 0.92 | 0.87 | — |
| Reference | 0.90 | 0.91 | |

TABLE 13

|  | 0 | 30 min | 45 min | 60 min | 75 min |
|---|---|---|---|---|---|
| subject 1 | 1.065769 | 0.916087 | 0.879866 | 0.89725 | 0.894333 |
| subject 2 | 0.940361 | 0.899331 | 0.899965 | 0.882474 | 0.762678 |
| subject 3 | 0.91134 | 0.950579 | 0.911402 | 0.818973 | 0.81925 |
| subject 4 | 0.932998 | 0.852055 | 0.860919 | 0.855898 | 0.84999 |
| subject 5 | 0.914711 | 0.906142 | 0.82784 | 0.844785 | 0.843547 |

Figure 21:
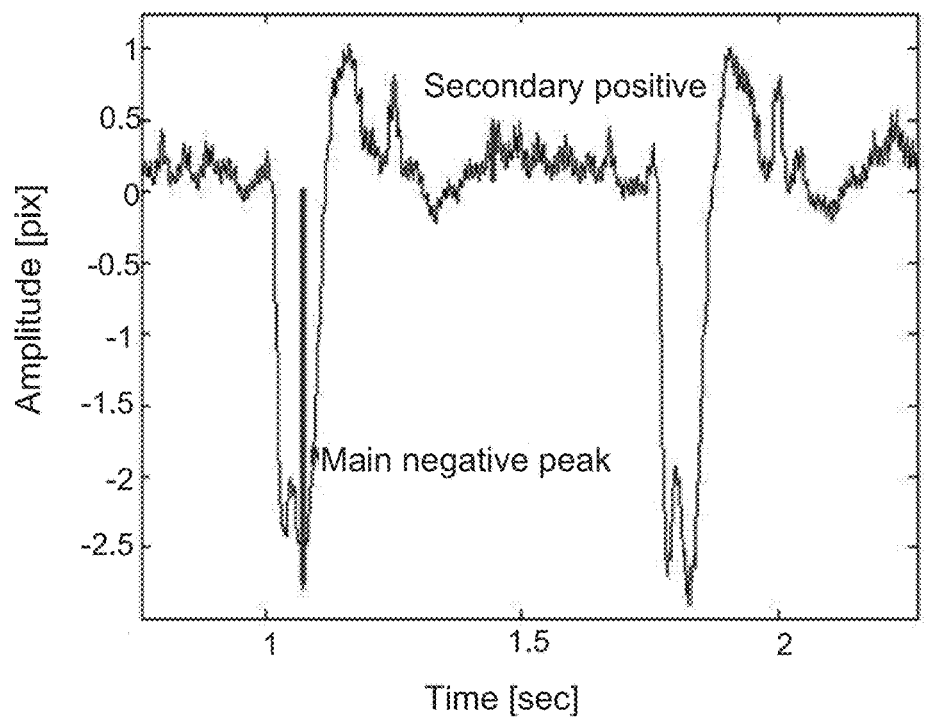
FIG. 21 is a graph illustrating the main negative peak amplitude to the secondary positive peak amplitude in the function indicative of skin vibration profile in the time domain.
Figure 22A:
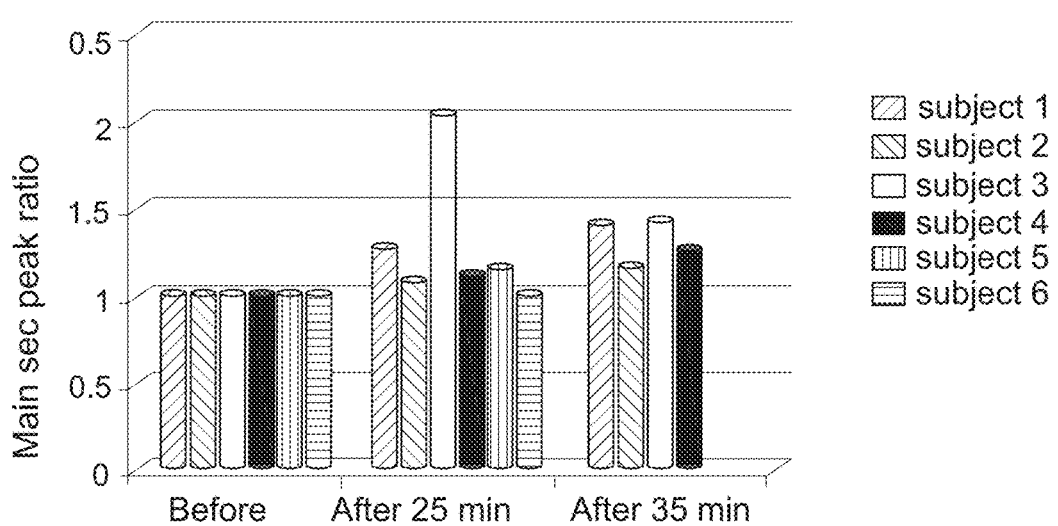
FIGS. 22A-22B are graphs illustrating the change of test subjects' ratios between main and secondary peak positions, as a consequence of alcohol consumption.
Figure 22B:
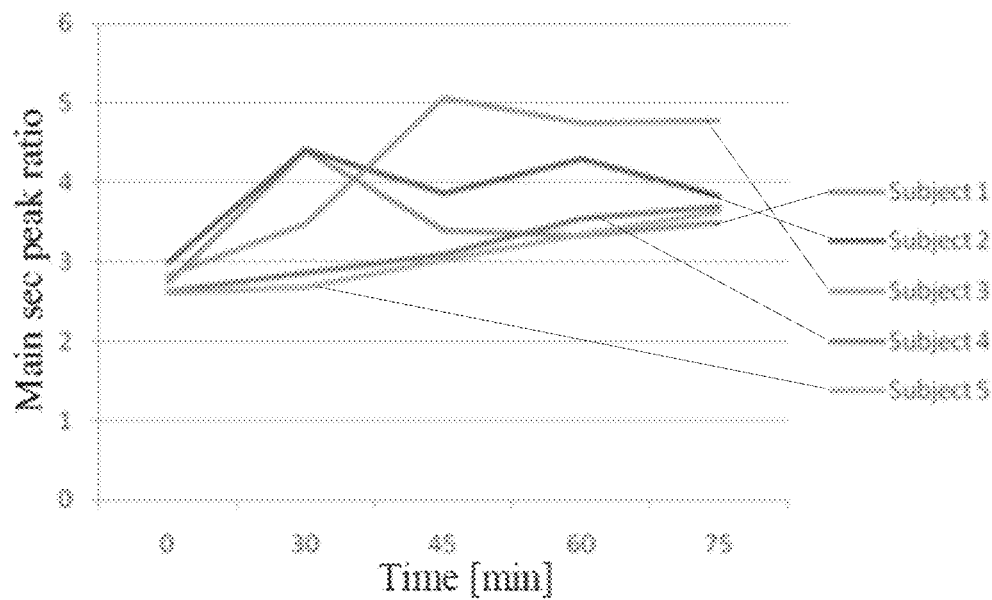

Referring to FIG. 21, the main negative peak amplitude and the secondary positive peak amplitude in a function describing the temporal variations of the position of the spatial correlation function's peak are shown. FIGS. 22A-22B are graphs illustrating the change of test subjects' ratios between main and secondary peak amplitudes, as a consequence of alcohol consumption.

Table 14 summarizes values of ratios between main and secondary peak amplitudes before drinking alcohol and after significant time (25 min & 35 min). Table 15 summarizes the values of ratios between main and secondary peak amplitudes in the long duration test, where measurements were taken before drinking alcohol and every 15 min thereafter (for 75 min). The data of tables 14 and 15 is shown graphically in FIGS. 22A and 22B, respectively.

TABLE 14

|  | Before | After 25 min | After 35 min |
|---|---|---|---|
| subject 1 | 3.38 | 4.30 | 4.74 |
| subject 2 | 2.60 | 2.81 | 3.02 |
| subject 3 | 1.90 | 3.87 | 2.70 |
| subject 4 | 1.73 | 1.93 | 2.19 |
| subject 5 | 2.26 | 2.60 | — |
| reference | 2.34 | 2.34 | |

TABLE 15

|  | 0 | 30 min | 45 min | 60 min | 75 min |
|---|---|---|---|---|---|
| subject 1 | 2.997614 | 4.422284 | 3.86795 | 4.291934 | 3.837522 |
| subject 2 | 2.736866 | 4.403912 | 3.397398 | 3.323514 | 3.503098 |
| subject 3 | 2.834672 | 3.482034 | 5.07221 | 4.743223 | 4.78544 |
| subject 4 | 2.623532 | 2.858851 | 3.100125 | 3.539668 | 3.700689 |
| subject 5 | 2.611516 | 2.673833 | 3.034982 | 3.354123 | 3.633107 |

It can be seen that when there is an alcohol in the blood vessel, the secondary peak becomes smaller relative to the main pulse. This also demonstrates the importance of the behavior of the secondary pulse as an indicator of presence of alcohol in the blood vessels.

Figure 23:
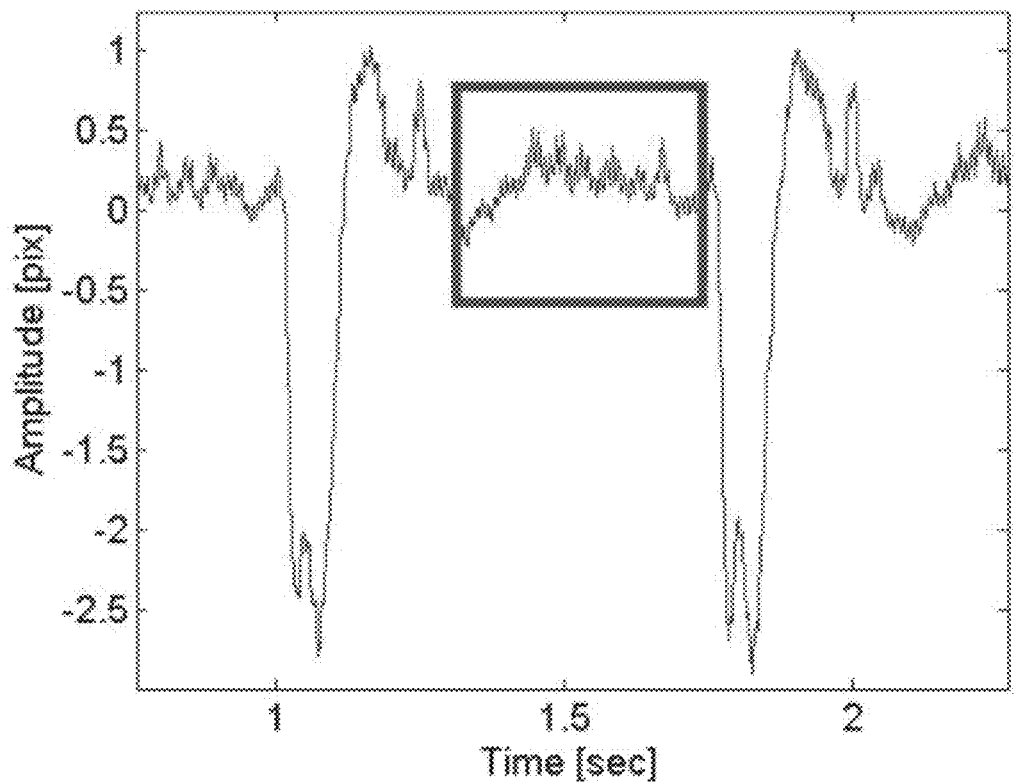
FIG. 23 is a graph illustrating the background noise in the function indicative of skin vibration profile in the time domain.
Figure 24:
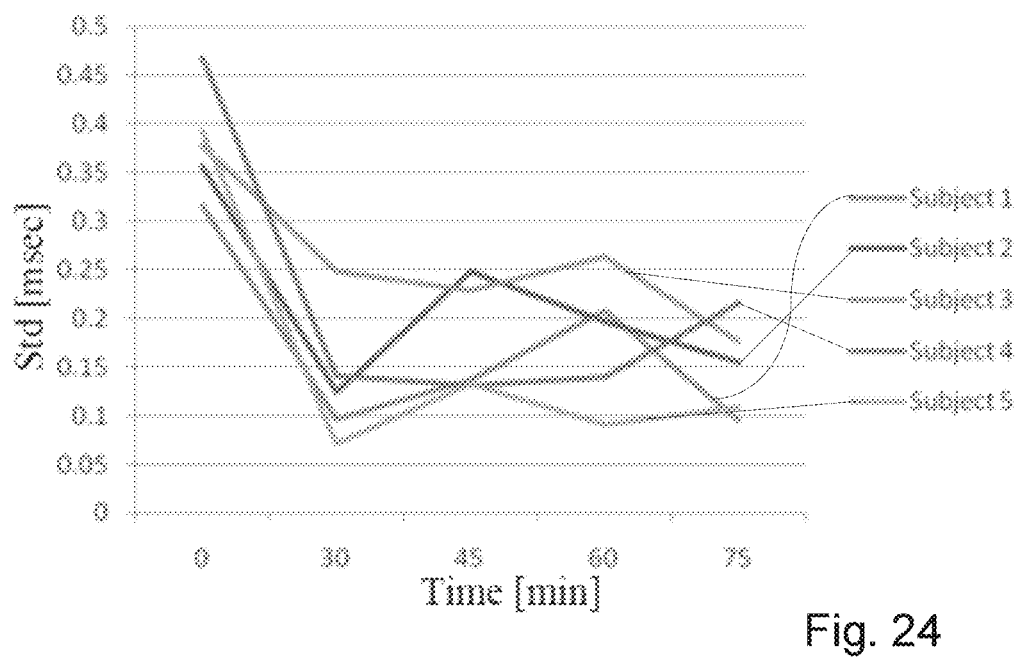
FIG. 24 is a graph illustrating the change of test subjects' standard deviation in background noise, as a consequence of alcohol consumption.

Referring to FIG. 23, the background noise in a function describing the temporal variations of the spatial position of the correlation function's peak indicative of skin vibration profile in the time domain is shown. FIG. 24 is a graph illustrating the change of test subjects' standard deviation of background noise, as a consequence of alcohol consumption.

The standard deviation of background noise was checked only in the long duration tests.

Table 16 summarizes the values standard deviations of background noise in the long duration test, where measurements were taken before drinking alcohol and every 15 min thereafter (for 75 min). The data of table 16 is shown graphically in FIG. 24.

TABLE 16

|  | 0 | 30 min | 45 min | 60 min | 75 min |
|---|---|---|---|---|---|
| subject 1 | 0.3164 | 0.096496 | 0.137565 | 0.207878 | 0.095239 |
| subject 2 | 0.357475 | 0.12388 | 0.248033 | 0.19633 | 0.15489 |
| subject 3 | 0.378046 | 0.248033 | 0.228488 | 0.264168 | 0.175701 |
| subject 4 | 0.467773 | 0.140524 | 0.131381 | 0.140187 | 0.216425 |
| subject 5 | 0.392776 | 0.071516 | 0.132013 | 0.091129 | 0.109303 |

From Table 16 and FIG. 24, it can be seen that when alcohol is present in the blood vessel, the background noise decreases.

Thus, it has been shown that the present invention can be also used for measuring alcohol level in the blood. The advantage provided by the technique of the present invention lies in the fact that the present technique enables real-time and non invasive estimation of alcohol in the bloodstream. This is in contrast with the known breath analysis technique, which is less reliable since it measures low concentrations of alcohol in breath.

The inventors have also conducted experiments for measuring breathing, blood coagulation and oxymetry using the technique of the present invention. The experimental setup used in these experiments was generally similar to the system of FIG. 1B, and in some cases a beam expander was also used.

In general, the system includes a laser, fast digital camera with its imaging lens and a computer to process the sensed images. All experiments were done twice by using two laser systems for comparison purposes. The first is a visible laser (Nd:YAG laser with wavelength of 532 nm) and the second is a non-visible IR (Infra-Red) laser at wavelength of 1550 nm. The two systems produced similar results. For the system using a visible laser a digital PixelLink model number A741 camera was used. The camera captures images of the secondary speckle patterns being reflected from the chest of the subject at rate of about 2200 frames per second (fps). The focal length of the optics used in the experiments was 150 mm for the 532 nm laser system and 600 mm for the IR system. The distance from the laser to the subject's chest was about 40 m. The laser output power was about 50 mW. In order to collimate the laser beam a beam expander ×3 was used. For the non-visible laser system an IR laser at 1550 nm was used for eye safety reasons and the model of the camera was changed to EHD-IK112. The sampling rate of the camera depended on the specific experiment and varied from 20 fps up to about 2000 fps. In all cases the experiments were performed on healthy female swine models—domestic mixed breed of large white and landrace pigs having weight of around 50 kg. These animals are similar in blood circulation, heart, skin and digestive systems to humans. Ten experiments were performed for a different swine in each experiment. The swine were anesthetized and put under artificial respiration.

In order to test each of the indicators, all the parameters were controlled and only one of them was change for each measurement, by using medications and surgery instruments. For example, in order to measure pulse rates, adrenalin was used to decrease/raise the swine's heart rate, while the respirator and other medications controlled its blood pressure, oxygen saturation etc. In each experiment a few parameters were tested. All the measurements were taken from the same measuring point—the swine's chest. All the parameters were measured by using the same method. The only difference was the process at which the results were analyzed.

Pulse and breathing rates were measured on a time scale but the results of all the other parameters are extracted from the value of the amplitude of the movement. Therefore, the invention provides for monitoring simultaneously both the pulse and breathing rate and one or more additional parameters. Since each of the parameters has special characteristics (amplitude value and shape) and since the invention provides for tracing nanometric movements, it is possible to measure multiple parameters simultaneously.

The inventors have conducted further experiments and demonstrated the capability of the technique of the present invention to simultaneously monitor multiple (five in this specific experiment) biomedical indicators—heart beating rate and shape, breathing, blood pulse pressure, blood coagulation and oxygen saturation. All measurements were performed simultaneously on pigs from a long distance of 40 meters.

It should also be noted that the experiments were conducted on different types of skin (texture and color) and it was shown that the results are practically independent on the wavelengths used.

Further, a calibration process is generally needed to perform remote biomedical estimation. The calibration is basically finding the translation factor that may translate the optical measurement done in pixels to the absolute value of the specific biomedical parameter. This is indeed done by equating the readings from the surgery room equipment to the optical readout. Indeed the calibration may depend on the location from which the measurement is done. However, the inventors have found that the measurements are very repeatable. The inventors conducted experiments while placing the measurement system on a tracker so the system is able to measure the relevant biomedical parameters on a moving subject and each time the measurement were extracted from the same location.

Breathing

Breathing is the process of supplying oxygen to the body and removing carbon dioxide from it, while its rate is the number of breaths taken per minute. The normal rate for adults is 12-20 breaths per minute.

As in the heart rate experiment, the measurement was done by processing reflections from the swine's chest. The measurements involved correlation of the time varied speckle patterns and plotting the amplitude of the relative shift of the correlation peak versus time. The reference measurement was done with a respirator, while the number of breaths per minute was controlled and changed in each measurement (within the range of 13-20 breaths per minute).

It should be noted that the data analysis algorithms allow to isolate the heart rate as well as the other parameters and to filter out the breathing movements from the results. The results presented below are the heart beats and they are not affected by the breathing. The filtering was done by inspecting the spectrum domain, identifying the breathing frequency and then removing it from the temporal signal. In the breathing experiment, measurement were performed with and without the respirator and it was shown that there is no significant difference in measuring breathing when the subject breaths freely.

Figure 25A:
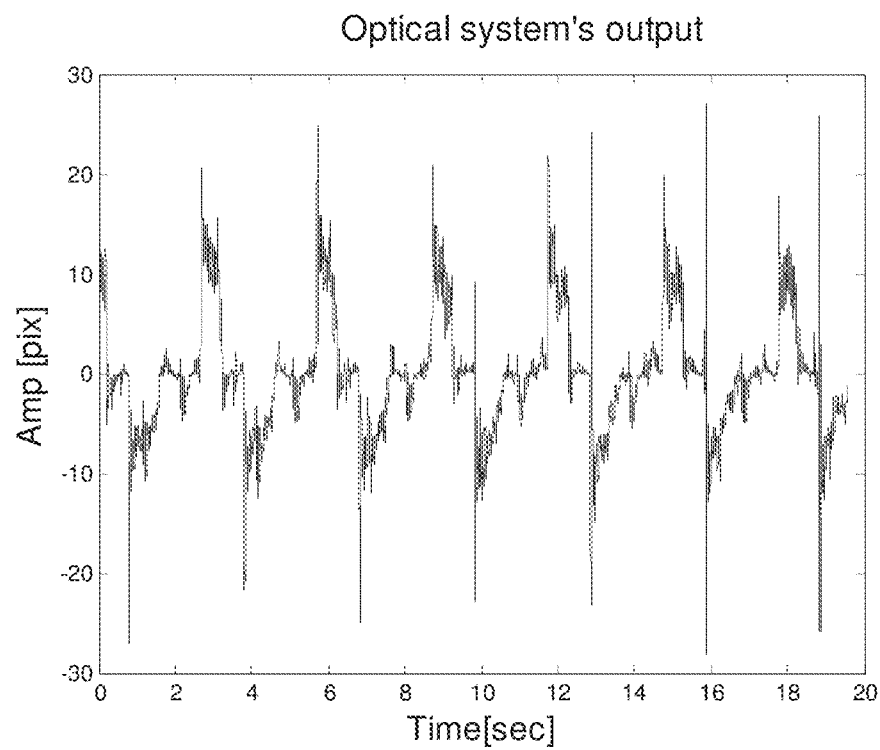
FIGS. 25A and 25B present the results of one of the breathing experiments.
Figure 25B:
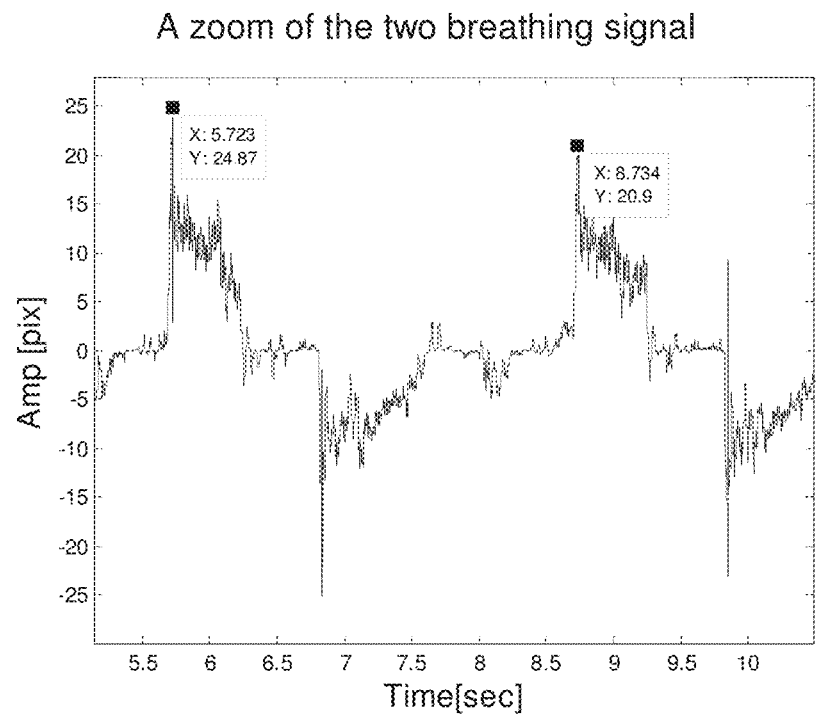
Figure 25C:
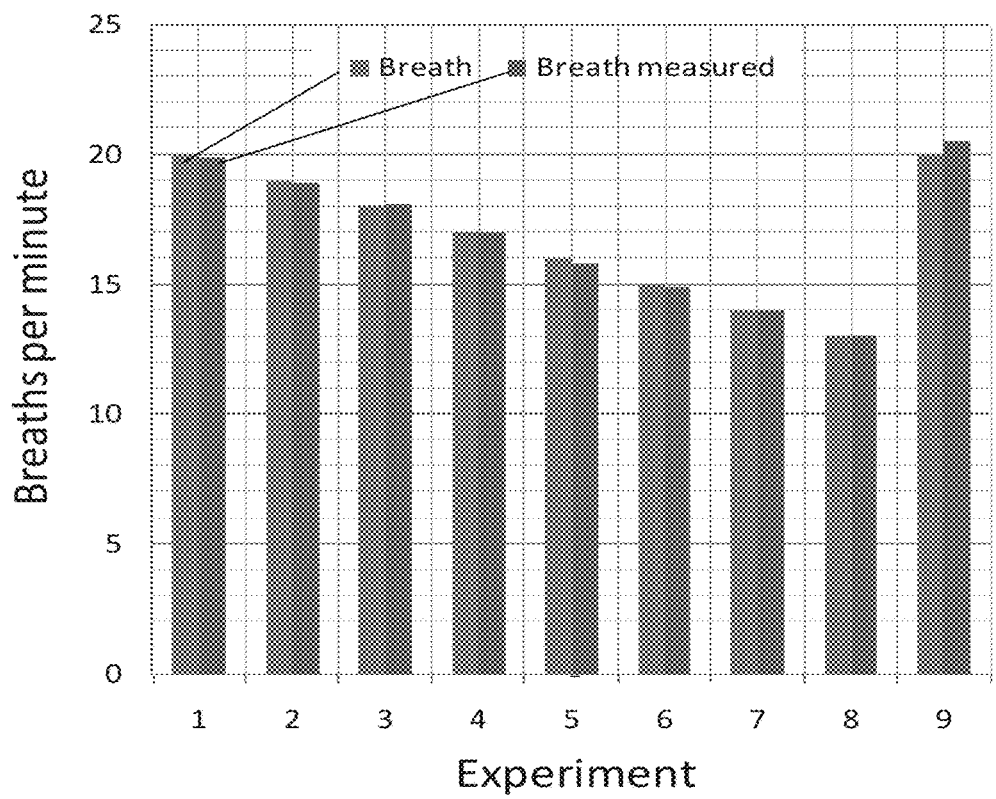
FIG. 25C shows a summary of the results of all 9 experiments, conducted by the inventors utilizing the system of the invention exemplified in FIG. 1B.

A total of 9 breathing experiments were conducted, and the number of breaths was changed between experiments by using the respirator (or pumped air breathe machine). Then, a different breathing rate is forced for each one of the experiments. FIGS. 25A and 25B present the results of one of the breathing experiments (experiment no. 1) and a summary of the results of all 9 experiments are presented in FIG. 25C. The experiment has demonstrated almost perfect correlation (99.7%) between the optical device and the reference measurement (respirator). The breathing experiment is summarized in Table 17.

TABLE 17

| Camera | Pixelink | |
| --- | --- | --- |
| Laser | 532 | Nm |
| Duration | 20 | Sec |
| Pulse | 61 | Beats/min |
| Breath | 20 | Breaths/mil |
| Breath measured | 19.9 | Breaths/min |

Coagulation of Blood (INR):

The technique of the present invention can also be used to determine a coagulation condition of blood. Coagulation is the process in which the blood forms clots after an injury in order to stop the bleeding and heal the injury. The process involves two components—platelets and proteins which are known as clotting factors. The platelets form around the injury site and at the same time proteins in the blood plasma respond to form fibrin and strengthen the platelet plug. Disorders of coagulation occur when there is a deficiency or abnormality in one of the clotting factors or platelets. There can be either increased tendency for excessive clotting (thrombosis) or an increased risk of bleeding (hemorrhage). Blood coagulation disorders can be either inherited or a result of another disease or a side effect of medications.

A common way of testing blood coagulation is the PT test (Prothrombin Time) which measures how long it takes for the blood to clot after adding certain chemicals to the blood. The normal result for PT test is 10-12 seconds. Since the result of the PT test varies from one lab to another, a standardized test—INR (International Normalized Ratio)—is commonly used and it is defined as:

$$INR = \left(\frac{PT_{test}}{PT_{normal}}\right)^{ISI} \quad (11)$$

Here, ISI (International Sensitivity Index) represents the responsiveness of any commercial system relative to international standard. Each manufacturer assigns an ISI value for any tissue factor they manufacture. The ISI value indicates how a particular batch of tissue factor compares to an international reference tissue factor. The ISI is usually between 1.0 and 2.0.

The normal INR value is close to 1 and is higher for patients who take anticoagulant medication and need to be monitored regularly (usually between 2 to 3). INR can be monitored either by a blood test or by portable monitoring device which requires a drop of blood sampled from the fingertip and inserted into the device.

The reference measurement for coagulation used in the experiments conducted by the inventors was done with the automatic INR measurement using CoaguCheck XP device. The swine got two shots of Herafin, while each 5 min the INR level was monitored. A pulse profile was distinguished out of the time evolution of the vibrations of the body due to blood vascular activity.

The experimental procedure was similar to the previous ones. The results were analyzed from the heart rate peaks and it's amplitude's shape and value. More specifically, a system similar to that of FIG. 1B was used to illuminate a portion of the skin. Variations in the speckle pattern were detected and processed as described above to determine a correlation function and a time variation of a feature (e.g., peak position and/or peak size) of the correlation function. Indeed, since a change in coagulation directly affects the viscosity of the blood, a change in coagulation strongly affects the mechanical movement of the surface of the skin that may be for example in proximity to a main blood artery. Measuring the movement profile with the opto phone may therefore allow after calibration to extract an INR parameter representing a coagulation condition of blood.

Figure 26:
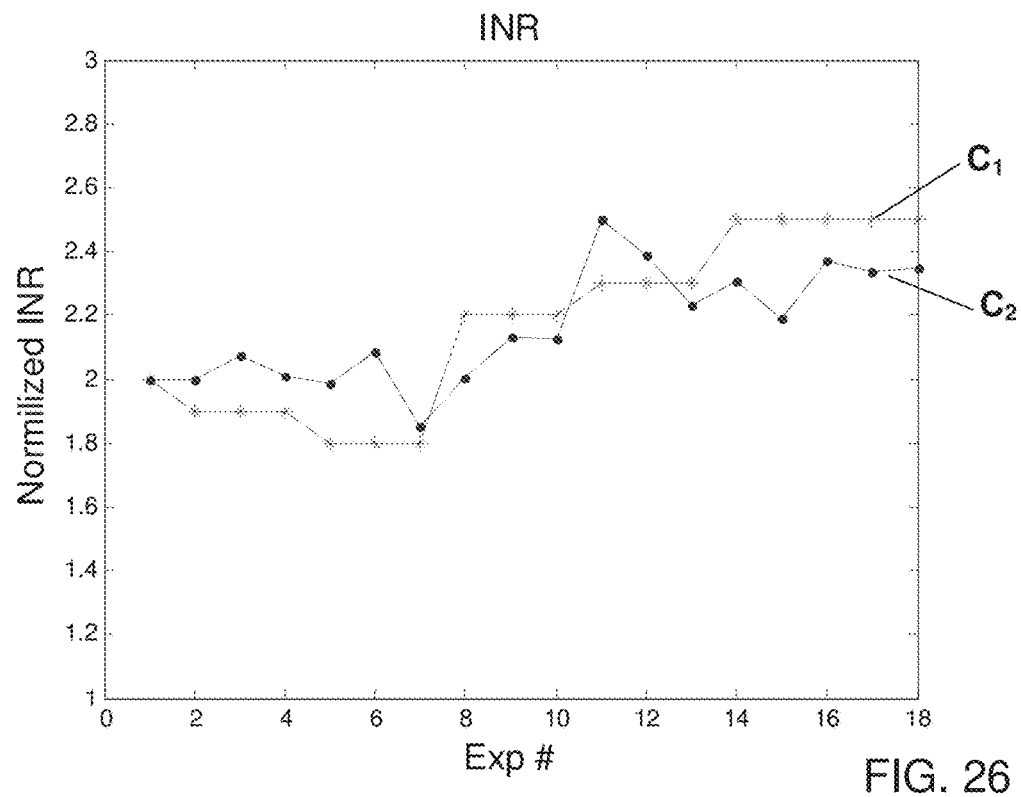
FIG. 26 presents the results of the INR experiment conducted by the inventors utilizing the system of the invention exemplified in FIG. 1B.

FIG. 26 presents the results of the INR experiment. Curve $C_1$ (red) corresponds to the reference measurement, while curve $C_2$ (blue) corresponds to optical output. The correlation coefficient between the graphs was 0.8, i.e. correlation of 80% between the two methods. The INR results can be estimated by analyzing the amplitude's value and shape.

Oxygen Saturation

Blood oxygen saturation level is the percentage of red blood cells that are loaded with oxygen. When red blood cells pass through the lungs they are saturated with oxygen which is then carried to body's organs. The normal percentage of red blood cells that are saturated (oxygen saturation) is above 95%. When oxygen saturation falls below 90% it is considered hypoxia. The body cannot function properly without an adequate level of blood oxygen.

There are two classical ways to measure blood oxygen level: the pulse oxymeter and an arterial blood gas test. The oxygen saturation can also be measured in the visible range (450 nm to 700 nm) using spectroscopic optical coherence tomography.

The pulse oxymeter is an optical sensor which is based on the fact that hemoglobin—the carrier of oxygen in the red blood cells—changes its absorption of visible light differently with varied oxygen levels. Hemoglobin which carries oxygen absorbs light at different wavelength than deoxygenated hemoglobin. The oxymeter uses red and infra-red light emitter and a photo detector that receives the light that passes through the sensor site. In the experiments conducted by the inventors, the oxymeter served as the reference measurement device by attaching the oxymeter to the swine's tail. Oxygen level was recorded each 10 seconds. Laser beam was projected onto swine's chest, while the oxygen pumping machine was turned off and the swine stopped breathing which caused the oxygen values to drop down. Also, neuromuscular blocker was injected in order to prevent independent breathing.

FIGS. 27A-27C presents the results received for two saturation level experiments while a reference measurement was performed and compared with the optical outcome. The optical system of the invention made 150 seconds of recording. A time evolution of the vibrations of the body due to blood vascular activity, as recorded by the optical system is shown in FIG. 27A. The sampling frequency was 1027 Hz. The change in a graph due to oxygen change in blood was analyzed, by analyzing the standard deviation (STD) of the vibration profile of each 10 seconds. The STD of the vibration profile is opposite to the oxygen level in blood stream. The optical results were multiplied by a constant (37.6) so that the first value would be the same value for the optical system and the reference value. The results are presented in FIGS. 27B and 27C, where curve $H_1$ (red) corresponds to the reference measurement and curve $H_2$ (blue) corresponds to the optical output of the optical system of the invention. The correlation coefficients between the graphs are 0.944 and 0.981 for FIGS. 27B and 27C respectively. Summary of the technical parameters of the experiment appear in Table 18.

TABLE 18

| Camera | Pixelink | |
|---|---|---|
| Laser | 532 | Nm |
| Duration | 150 | Sec |
| Pulse | 84 | Beats/min |
| Oxygen (%) | 94-81 | % |
| Breathing | 19.9 | Breaths/min |

The following is the description of additional experiments of the invention demonstrating how the invention can be used for measuring various other parameters/conditions of a subject.

Intra-Ocular Pressure

The following section, describing FIGS. 28-32, refers to tests conducted by the inventors on rabbits, in order to determine a relationship between intra-ocular pressure (IOP) and parameters of the vibration profile of the subjects' eye in the time domain.

The tests compared IOP of a rabbit's eye with the average amplitude of oscillations of a time-varying function describing the time varying position of the peak of the spatial correlation function (the time-varying function being indicative of vibrations of the rabbit's eye). The tests showed that the temporal change of the IOP is proportional to the temporal change of β(t) (which is proportional to the relative shift of the speckle pattern):

$$P_{IOP}(t) \propto \beta(t) \qquad (15)$$

Therefore, β(t) can be used to estimate IOP.

The aim of the test was to show that the blood pressure in the blood vessels in the retina affects the movement of the sclera/iris in a way that is correlated to the IOP, i.e. the sclera/iris slightly pulsates due to the blood supply to the eye. This movement, although being very small, can be detected by the speckle-based measurement of the present invention, since the movement precision that our technique can allow is in the nanometric scale. It is important to emphasize that the measured movement is solely the pulse of the iris/sclera, and not the movements of the iris or the eye. The movements of the iris or the eye are undesirable, and can be filtered out by performing measurement over sufficiently short time scale.

In the experimental setup, rabbits had an infusion connected to their eye in order to control their IOP. The experimental system was set up as the system of FIG. 1B, where and the optically based monitoring system was positioned at range of about 50 cm from the rabbit. The system included a fast camera and a laser. The readout of the camera was analyzed with Matlab software by a computer (control unit). The experimental system monitored the secondary speckle patterns generated due to reflection from the rabbit's sclera, and tracked the trajectory of the movement of the speckle patterns. During the experiments the rabbits were anesthetized. The source of coherent light was a harmonic of CW Nd:YAG laser which produced a beam having wavelength of 532 nm to illuminate the sclera of the rabbit. The reflections were analyzed using fast digital camera from "PixeLink". The obtained results were analyzed with Matlab software.

In order to vary the IOP of the rabbit's eye during the experiment, the elevation of the infusion bag was changed.

It is known that pressure difference is proportional to elevation difference and can be estimated as:

$$\Delta P = \rho g \Delta h \quad (16)$$

where $\rho$ is the density of the infusion liquid, g the gravity acceleration and $\Delta h$ the elevation difference. The translation between the pressure value obtained in Eq. 6 into mmHg units can be calculated using the following translation:

$$1\ Pa = 1 N/m^2 = 9.8692 \times 10^{-6}\ atm = 7.5006 \times 10^{-3} torr = 7.5 \times 10^{-3}\ mmHg \quad (17)$$

Figure 28:
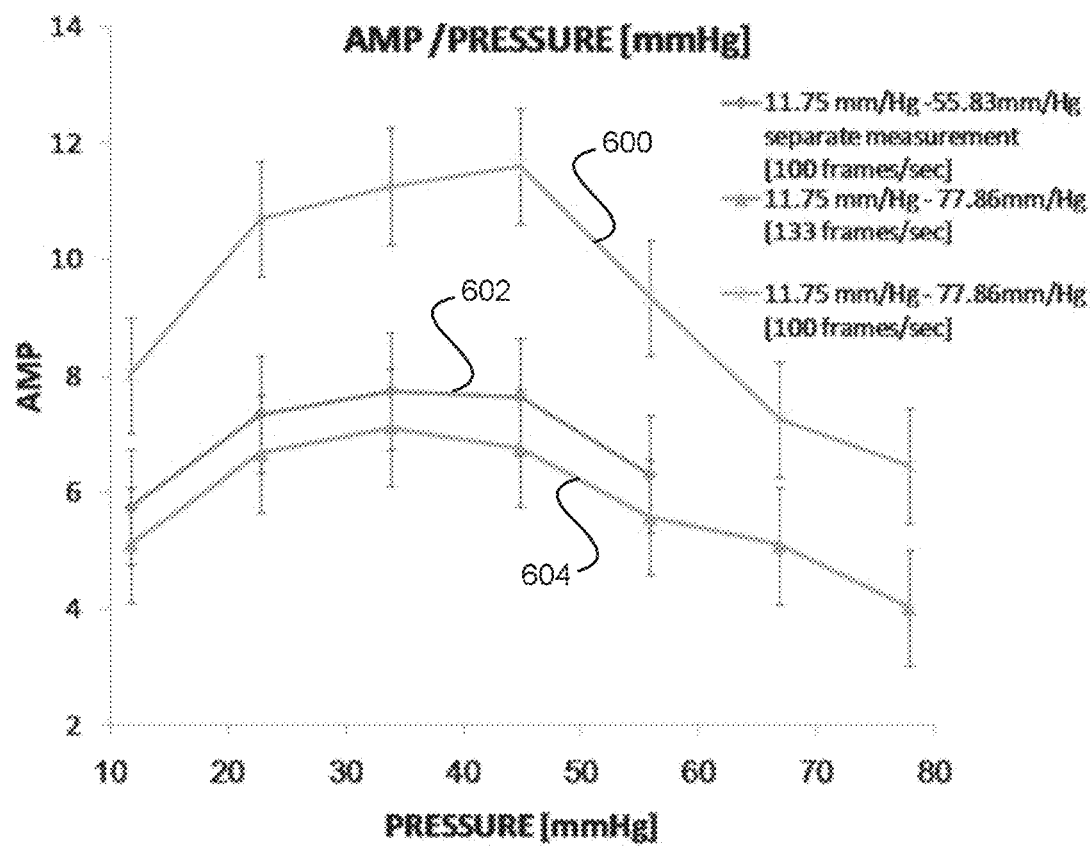
FIG. 28 is a graph illustrating the oscillation amplitude of a function indicative of the eye's vibration as a function of intra-ocular pressure (IOP), measured using the system of FIG. 1B using a 10 mW laser.

Referring to FIG. 28, there is depicted a graph illustrating the oscillation amplitude of a time-varying function describing the time varying position for the spatial correlation function's peak being indicative of the eye's vibration as a function of intra-ocular pressure (IOP), where the time varying-function was generated via the above-described system using a 2 mW laser.

One may see the relation between the oscillation amplitude of the time varying position of the spatial correlation function's peak obtained by using the above mentioned experimental system and the IOP in mmHg units computed according to Eq. 7 and 8 (based on the height difference between the infusion bag and the eye of the rabbit).

The graph illustrates three different sets of measurements, each set being performed according to a different technique. The uppermost curve 600 was obtained by sampling at rate of 100 frames/sec, while each measurement was taken separately and not in a continuous manner along the time axis. The middle curve 602 corresponds to a measurement taken at sampling rate of 133 frames/sec in a continuous measuring manner. The lowermost curve 604 was obtained using a continuous measuring but at sampling rate of 100 frames/sec. The bars around each measurement designate the standard deviation that we had after averaging more than 20 measurements. The current to the laser was 0.2 A which means illumination power of about 2 mW.

From the obtained results one may see that the decrease in the optically determined oscillation amplitude of the time varying positions of the peak of the spatial correlation function is obtained for pressure above ~40 mmHg. This is since this was approximately the inherent IOP of the rabbit's eye; when pressure was induced above this IOP value, the decrease was measured since the infusion bag overcame the inherent pressure in the eye of the rabbit. One may also see that in the experiment, the error in measurement is about 15%. But it is important to note that the accuracy of conventional measurement devices is also about 10%-15% while the current technique is a remote non harmful measuring device.

Figure 29:
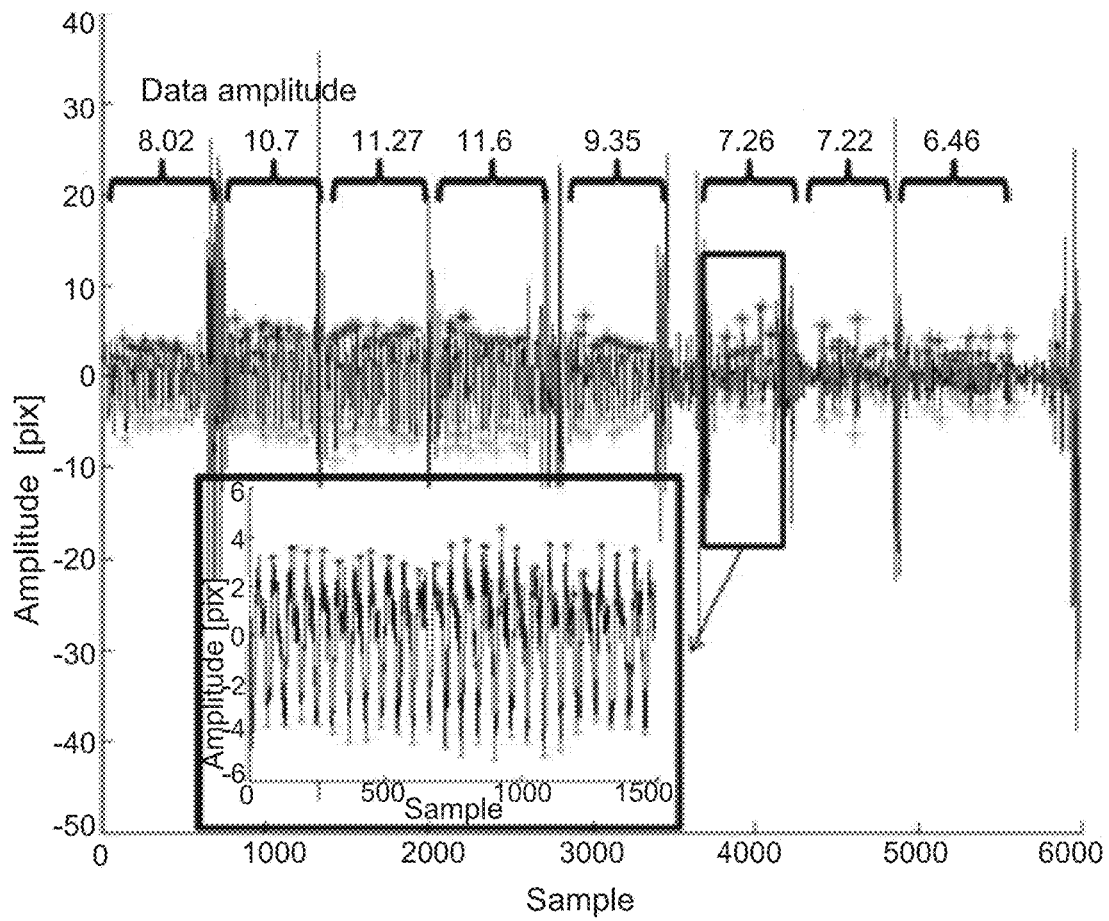
FIG. 29 is a graph illustrating a function indicative of the eye's vibration when IOP is changed in a rabbit's eye.

In order to understand how the values of the amplitude were extracted, reference is made to FIG. 29, which illustrates an example of the obtained readout in one of the performed experiments. In FIG. 29 one may see that a time-varying function describing the time varying position of the peak of the spatial correlation function being indicative of the eye's pulsating motion was generated. Every 500 samples, the elevation of the infusion bag was changed. During these changes, high amplitude artifacts appear due to the change in the elevation of the infusion bag. The oscillation amplitude of the time-varying function was measured and averaged for each set of 500 samples, in order to obtain an average amplitude corresponding to each elevation of the infusion bag (i.e. corresponding to a different IOP).

Figure 30:
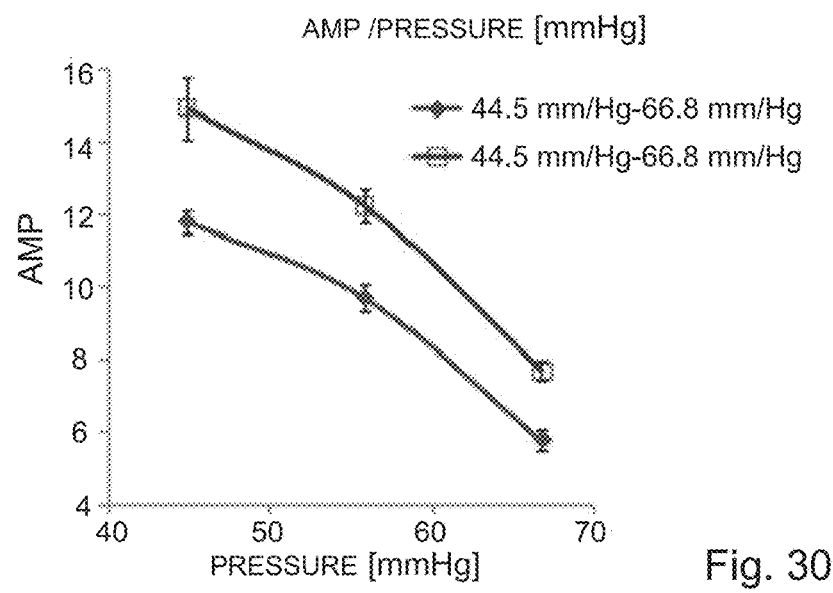
FIG. 30 is a graph illustrating amplitude of a function indicative of the eye's vibration as a function of intra-ocular pressure (IOP), where the function was generated via the system of FIG. 1B using a 2 mW laser.

The same experiment was repeated using a 10 mW laser. The results of this experiment are shown in FIG. 30. One may see that in this case the standard deviation error is much lower and can be estimated to be about 5%. The reason for the improved performance is related to the optical power of the illuminating laser. When the supply current was only 0.2 A the laser was at the threshold of its lasing and thus it was not stable enough. Its instability caused some of the standard deviations fluctuations. When the supply current was 0.25 A the laser was more stable and the results were much more repeatable. Note that the difference between the various curves in each one of the figures of FIGS. 28 and 30 is related to measurements performed at different positions along the sclera or measurements performed for different eyes. The standard variation for each one of the curves in FIGS. 28 and 30 is obtained for measurement performed in the same location for the same rabbit over the duration of the same experiment.

Note that the same measurement can be performed with eye-safe laser at wavelength of 1550 nm.

Figure 31:
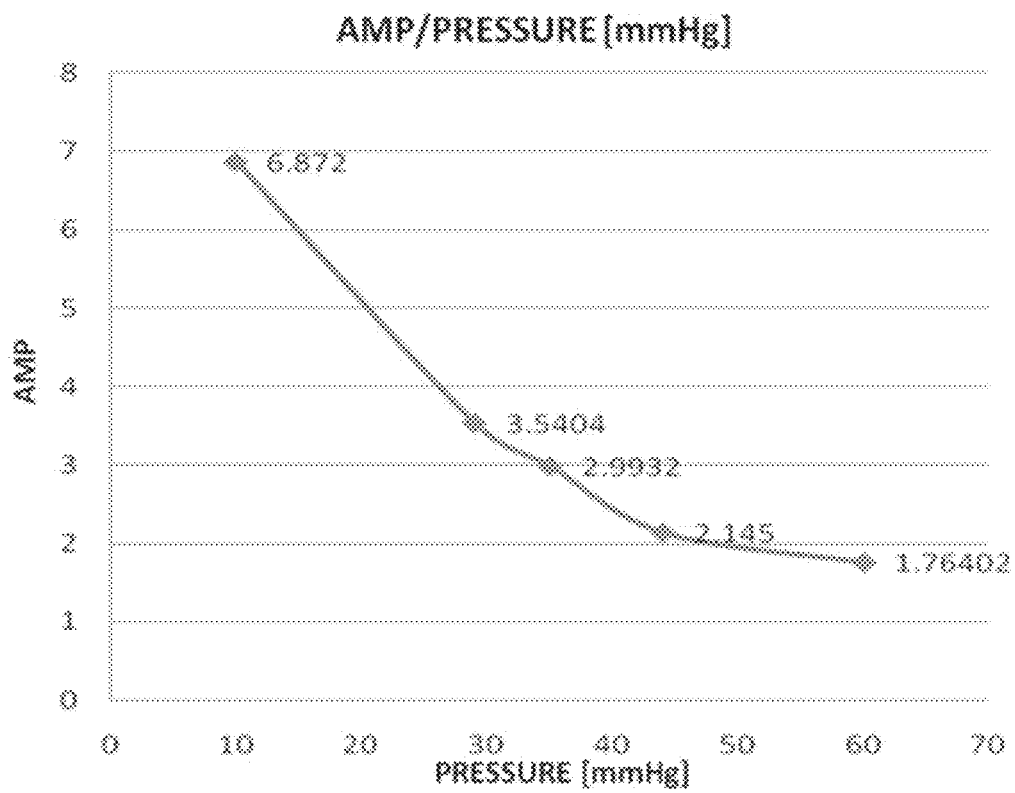
FIG. 31 is a graph illustrating the oscillation amplitude a function indicative of the eye's vibration as a function of intra-ocular pressure (IOP), where the IOP was measured via a Goldmann tonometer.

Referring to FIG. 31, there is depicted a graph illustrating the oscillation amplitude of time-varying function describing a time varying position of the peak of the spatial correlation function (the time-varying function being indicative of the eye's vibration) as a function of intra-ocular pressure (IOP), where the IOP was measured via a Goldmann tonometer.

Another important measurement was performed on a new rabbit following the same measurement procedure as for the experiment of FIG. 30, but this time the extracted results were compared with absolute reference measurement coming from a conventional Goldmann tonometer. The measurement was done as before by illuminating the rabbit's iris.

It must be noted that the measurement at 10 mm/Hg in FIG. 31 was performed before inserting the infusion bag. The measurement presented in FIGS. 28 and 30 were performed on rabbits after tens of attempts of inserting the infusion into their eye. Those attempts deformed the rabbit's eye and changed their inherent IOP. In the measurement of FIG. 31 a new rabbit was used and indeed its IOP was lower. In fact, it was verified, using the reference Goldmann tonometer, that the average IOP of the rabbits used in the experiments of FIGS. 28 and 30, that after finishing the experiment the rabbits' IOP indeed changed from 10 mmHg (before experiment) to around 35 mmHg (right after the experiment).

In FIG. 31, the extracted results show good monotonic relation between the optically measured amplitude and the reference IOP measurement. The amplitude values are smaller than those of FIGS. 28 and 30 since a lens with different focal length was used in the optical device (55 mm in FIG. 31 instead of a lens with focal length of 50 mm used to obtain the results of FIGS. 28 and 30).

From the obtained results included in FIG. 28, it can be seen that that the induced variations in the IOP causes a variation of the reflected speckle patterns at the iris of the rabbit's eye. In two of the experiments (uppermost curve 600 and lowermost curve 604), the monitoring of that variation was performed continuously, while in the third experiment (middle curve 602), the measurements were obtained independently one from each other. In all the three cases, the curve's tendency is the same and it validates the correlation existing between the IOP and the processing applied over the speckle patterns reflected from the iris.

When comparing the continuous monitoring experiments, both curves 600 and 604 have the same aspect but are scaled with respect to the global amplitude value. This is due to the fact that the lower the sampling rate, the lower is the amplitude of the speckle patterns.

In all the cases presented in FIG. 28, the measurement error has standard deviation of about 15%. The results depicted in FIG. 30 show a reduction of the standard deviation error until approximately 5%. The reason for that improved performance is related to the timing of the measurement. In fact, the results of FIG. 30 were obtained in the beginning stage of our experiment, while the results of FIG. 28 were obtained after large number of tests, which affected the structure and therefore also the IOP of the rabbit's eye. Note that the difference between the various curves of FIG. 28 and those of FIG. 30 arises either because the measurements were performed at different positions along the iris or because the measurements were performed on different eyes. The standard deviation for each one of the curves in FIGS. 28 and 30 is obtained for measurements performed in the same location for the same rabbit over the duration of the same experiment. This fact suggests that the standard deviation error may be independent of the measurement point.

The results presented in FIG. 31 show a monotonic and a distinct relation between the absolute reference measurement of the IOP performed by Goldmann tonometer and the amplitude readout produced by the constructed optical device.

The Goldmann tonometer has a measurement error of about 1 mmHg. In contrast, the error of the present technique is about 0.775 mmHg—considering standard deviation error of 5% and a typical IOP values in humans of 15.5 mmHg in average. Therefore, the technique of the present invention provided both a lower measurement error (i.e. higher accuracy), as well as the advantage of remote and continuous monitoring capability.

Furthermore, increase in IOP is the major risk factor for glaucoma, while decrease in IOP indicates fluid leakage and deflation of the eyeball (an undesirable condition in its own right). The results of FIG. 28 show that the technique of the present invention is sensible to both increase and decrease of IOP.

The inventors have further found that IOP measurements using the motion measurements based on de-focused imaging of speckle pattern can be even more improved by utilizing application of external pressure field. To this end, reference is made to the above-described measurement system 500 of FIG. 11A. For the IOP measurements, the region of interest is a subject's eye and the external field source operates as vibration/motion affecting unit and includes an acoustic waves' generator, such as loud speaker(s).

The experimental setup used by the inventors in this case is similar to the regular setup used in the above-described experiments and includes a laser illuminating the cornea and a camera that analyzes the back reflected light. In addition to that, small loud speaker were used generating acoustic pressure waves at a given sound frequency directed towards the cornea. The external pressure waves generated via the loud speakers that are directed towards the cornea press the cornea in a predict manner. The laser and the camera analyze the created movement via the speckle based procedure. The internal IOP depends on how much movement of the cornea occurs due to the external pressure waves since the internal pressure objects the external pressure coming from the loud speakers. The movement is measured via the speckle technique and compared to the calibration data from which an absolute value for the IOP is extracted.

Blood Pulse Pressure

As mentioned above, the technique of the present invention can be used to determine blood pulse pressure. To do this, a system similar to that of FIG. 1B can be used to illuminate a region of a patient's skin adjacent to blood vessel(s) (e.g. the wrist). Variations in the speckle pattern are detected and processed as described above to determine a correlation function and a time variation of a feature (e.g., peak position and/or peak size) of the correlation function. The time variation of the spatial correlation function has a profile similar to that shown as shown in FIG. 6A, and the amplitude of the peaks is indicative of the blood flow in the measurement (illuminated) location. The inventors have found that the amplitude of the main peak (parameter 1 of FIG. 6A) of the time varying spatial correlation function is in good correlation with the patient's blood pulse pressure, owing to the fact the time variation of the measured data (speckle pattern) corresponds to the blood flow (motion) within the measurement location.

Figure 32:
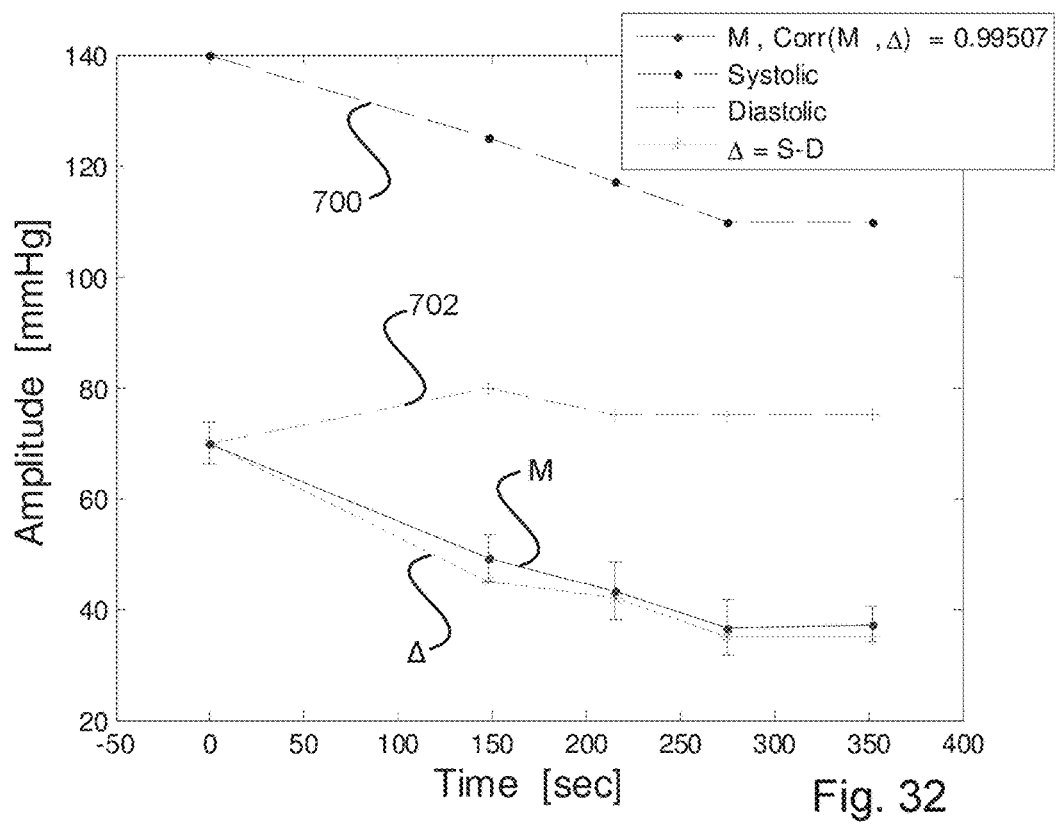
FIG. 32 is a graph illustrating the change of a test subject's pulse amplitude over time, as compared to the test subject's pulse blood pressure.

FIG. 32 is a graph illustrating the change of a test subject's pulse amplitude over time, as compared to the test subject's pulse blood pressure. The reference pulse pressure is shown by the curve denoted as curve Δ, and was obtained by subtracting diastolic pressure (curve 702) from systolic pressure (curve 700), both of which were measured using a manual sleeve-based reference measurement device. The curve (denoted as M) illustrates the value of the pulse amplitude obtained using the proposed optical technique at same time as the above-mentioned reference measurements. The time duration of the experiment was 350 sec. The sampling of the camera (PDA) was performed at 300 Hz. It can be seen that a strong correlation exists between the reference curve Δ and the curve M obtained by the technique of the present invention.

Cattle Monitoring:

The technique of the present invention can also be used to determine biomedical parameters of a ruminant. Ruminant biomedical parameters monitoring such as monitoring of heart beating, pulse count, blood pulse pressure and breathing count can be very important in case of cattle as this information can be used to optimize the milking and the breeding timing of caws. Advantageously, such monitoring is performed without contact which is appreciable when dealing with animals. Applying the opto-phone technology and observing the surface of the skin of the caw, in positions that are close to a main blood artery, may allow—after monitoring of the movement and after proper calibration—to extract the above mentioned biomedical parameters in real time and in a continuous manner.

Temperature Monitoring:

The technique of the present invention can also be used to determine the temperature of a biological tissue. To do this, a system similar to that of FIG. 1B can be used to illuminate the biological tissue (e.g. a portion of skin of a body). Variations in the speckle pattern are detected and processed as described above to determine a correlation function and a time variation of a feature (e.g., peak position and/or peak size) of the correlation function. Indeed, the temperature of a tissue is related to the temporal movement profile of the tissue. Therefore, by extracting this profile and after proper calibration it is possible to estimate the temperature of the inspected tissue.

Flow Velocity and Volume Monitoring

The technique of the present invention can also be used to monitor the flow velocity and volume. The flow velocity and volume may be correlated to temporal variations of the spectral content of the temporal pattern of the correlation peak extracted from a correlation function between successive defocused images of a speckle pattern generated at a surface of an organ in which the flow is monitored. Indeed, by insetting nanoparticles through the flowing liquid and inspecting the temporal change in the speckle patterns generated due to the scattering from those nanoparticles, one may estimate the velocity and the volume of the flow because e.g. faster flow may generate faster movement of the speckle patterns. Thus, the velocity of flow is proportional to the temporal flickering of the inspected speckle patterns. This flickering can be computed in real time by correlation based processing.

The measurement of the opto phone provides sensing of the temporal movement profile of the inspected surface. It can be applied in plurality of wavelengths and in plurality of spatial positions. When plurality of wavelengths is applied, e.g. two, the measurements can be useful for application as oxymetry where the difference or the ratio of the temporal behavior at two wavelengths of absorption is inspected.

In case of flow velocity the measurement can be done in one of two possible ways. In a first method, measurement of the temporal profile may be simultaneously performed at two (or more) spatial positions with a known distance between them. By correlating the temporal sequence of pulses extracted from the two spatial positions, the temporal relative shift between the two sets of pulses may be computed. This temporal shift when dividing by the a priori known spatial distance between the two measurement points provides the flow velocity. In a second method, the measurement of the flow velocity can be done by doing only one measurement in a single spatial location. In this case the exact temporal profile of the pulsation is measured at high temporal resolution (with fast detector at sampling rate of e.g. GHz). Since the flow velocity affects the flow profile along the blood artery as explained above, the high precision extraction of the temporal pulsation profile can be related to the flow velocity. In all cases of measurement of the flow velocity and oxymetry etc, it is preferred to perform the measurement near principle blood artery where the pulsation affects are significantly more evident.

Bone Fractures Measurement

The inventors have conducted experiments aimed at measuring/detecting bone fractures. To this end, a measurement system similar to the above-described system 500 of FIG. 11A is used, where the external field source 502 operates as a vibration/motion affecting unit and includes a pressure source generator, such as loud speakers, placed close to a body portion, e.g. patient's hand, for applying acoustic waves during the de-focused imaging of speckle pattern. The loud speakers generate acoustic signals, i.e. pressure waves, which cause vibrations to the patient's hand. The movement of the bone having fractures is different from one without fractures. The above-described opto phone (measurement unit) was used to inspect the movement of the skin and the bone (generate a sequence of the speckle patterns), and the control unit processes this data to identify whether there is a deviation from the calibrated value (which can be the second and the non broken hand. The intensity of the speaker depends on the distance at which the speakers are positioned. Positioning the speakers a few centimeters from the patient's hand (generally a body portion) and applying intensity of about 90 dB provides that the speakers vibrate the hand, and if the bone has fractures it does not vibrate as a healthy hand does. This can be identified by doing proper calibration (i.e. mapping the hand before it was broken) or comparing the optical response between the two hands that are supposed to be substantially symmetrical. Thus, to implement the technique of the present invention for identifying/detection fractions in a bone, first, the unbroken bone of the subject is inspected in means of vibration profile and frequencies domain. This measurement is used as a reference measurement. Later, the broken bone (or the one which is supposed to be broken) is inspected, while its vibration profile and frequencies are compared to the reference measurement in order to extract the differences and to define wherever the bone is broken or not. Upon identifying the existence of fracture, the laser spot scans the hand and maps it point by point. This technique can be used as a replacement for or addition to a Roentgen image for observing fractures. This can be an indication for luck of calcium in bones in elderly woman etc.

Figure 33A:
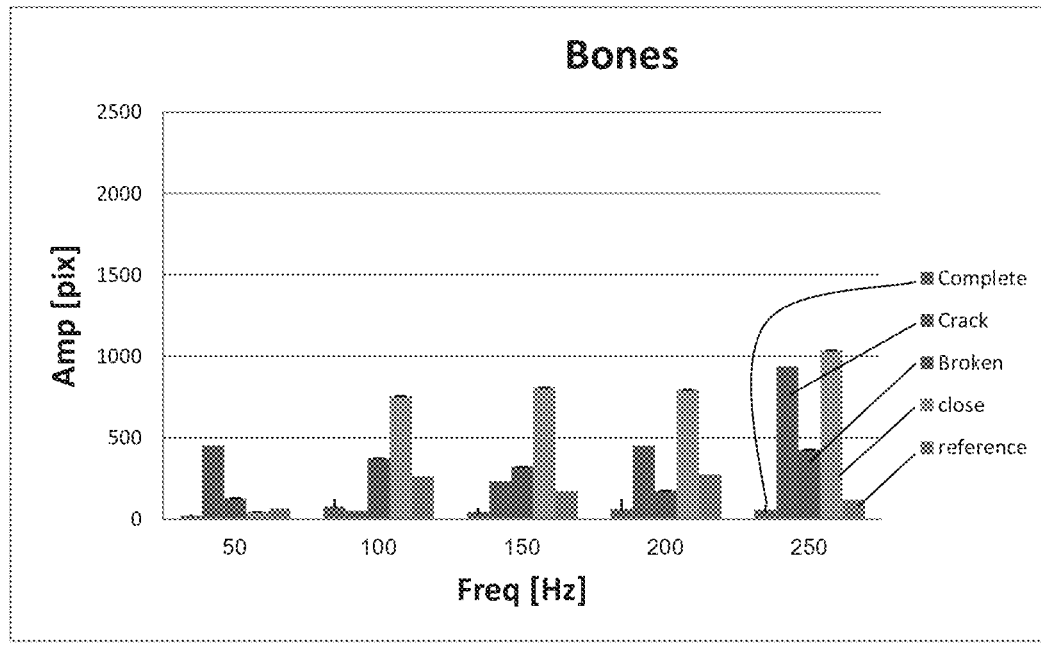
FIGS. 33A and 33B illustrate experimental results for using the system of FIG. 11A for bone-fractures measurement.
Figure 33B:
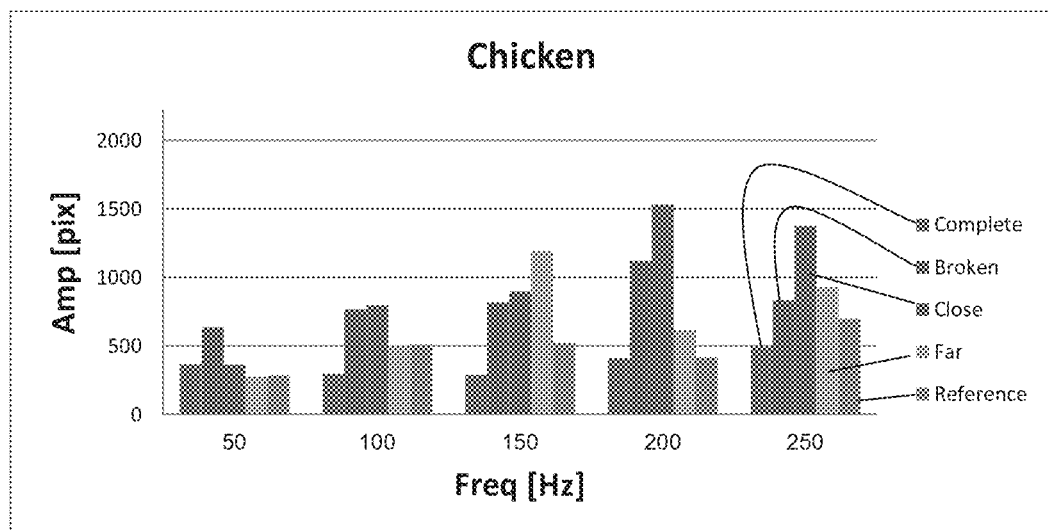

FIGS. 33A and 33B illustrate the results of experiments conducted by the inventors. In these experiments, the bones undergo shaking at different frequencies (50 Hz, 100 Hz, 150 Hz, 200 Hz, 250 Hz); the camera (PixelLink PL-E531) captures images of the secondary speckle pattern reflected from the bone at the rate of 700 frames per second (fps); the distance from the laser to the bone is approximately 5 cm; and the laser output power is approximately 5 mW. After extracting the speckle pattern in each frame, the correlation is calculated and the change in the 2-D position of the peak versus time is obtained.

FIG. 33A shows the results of the first part of the experiment illustrating the Complete, Crack, Broken, Close, Far and Reference measurements, were Complete is an optical measurement result for the illumination of a spot of complete bone, Crack is an optical measurement result of cracked bone (the cracked spot is the same spot that is illuminated on the complete bone), Broken is an optical measurement result of a fracture spot, Close is an optical measurement result of a close spot to the fracture, Far is an optical measurement result of a far spot to the fracture, Reference is an optical measurement result of a reference bone. It is shown that that the reference bone result is lower than a broken and crack bone, the ratio between close point results to complete one is much higher than the ratio between close point results to broken and crack one. In order to diagnose if there is a crack or fracture one can see that at 50 Hz and 100 Hz experiments result in higher response to a crack than a fracture one.

FIG. 33B shows the results of the second part of the experiment where a piece of chicken is illuminated while the beam is aimed to one of the chicken's bones. After illuminating on a complete bone, the bone has been broken and the same experiment was repeated on a piece of chicken while the bone of the chicken is broken. The conditions of this part were the same as the first one.

As shown in the figure, the reference result is lower than a broken one; the complete result is lower than a broken one; the ratio between a close point experiment to a reference experiment is much higher than the ratio between close point experiment to a fracture point experiment.

The parameters in the graphs are the average of all of the experimental results, where the complete and the broken parameters were measured 8 times, the reference parameter were measured 6 times, and the far and close parameters were measured 4 times (each experiment was done 4 times).

As described above, the technique of the present invention provides for measuring various bio-chemical parameters of a subject, by properly obtaining data indicative of a shift in a speckle pattern (resulting from de-focused imaging) caused by motion/vibrations within a region of interest of the subject's body, and properly analyzing data indicative of the vibration profile. Several such parameters can be measured simultaneously. In a case of heart beats rate, the time between the beats (between two highest amplitudes in the local time slot) is identified. In a case of breathing, a biased sinusoidal profile at slow frequency (less than 0.5 Hz)

is identified, being easily separated from heart beats rate by the shape and the frequency (also by analyzing the frequency domain diagram). For the blood pulse pressure measurements, the difference in the dynamic range of the heart beat peak (the difference between the positive and the negative peaks of the vibration profile) is identified. For the oximetry monitoring, the standard deviation of the 10 seconds time window in the vibration profile is determined. For performing the coagulation analysis, a collection of each pulse profile one over another in the same time domain is first constructed, being something similar to "eye" diagram used in communication equipment (eye diagram is an indicator of the quality of signals in high-speed digital transmissions). For construction of the "eye" diagram, each one of the OCG (Opto cardiography) pulses is cut from the time vibration vector according to the shape and all of the pulses are pasted one on another (i.e. construction of an "eye diagram" shape), and this step is repeated for every optical sample.

In the embodiments of the invention in which external temporally periodic stimulation is applied (as in IOP with loud speakers, bones fractures, glucose with AC magnetic field), the position of the correlation peak between adjacent speckle images is determined and the temporal chart of the change in the position of the correlation peak is obtained. Then, the Fourier transform of this temporal chart is determined and its spectrum is obtained, thereby enabling to examine the amplitude value of the spectrum at the stimulation frequency of the external simulator.

Thus, the present invention provides a novel, simple and effective technique for monitoring/measuring various conditions of a subject's body. Those skilled in the art will readily appreciate that various modifications and changes can be applied to the embodiments of the invention as hereinbefore exemplified without departing from its scope defined in and by the appended claims.

The invention claimed is:

1. A system for use in monitoring intra ocular pressure (IOP) of a subject, the system comprising:
    a measurement unit comprising: a pressure field generator configured and controllably operable to generate a pressure field of a predetermined profile and apply said pressure field to each of one or more portions of a cornea surface of the subject during a certain time period as an external stimulation; and an imaging device configured and operable to perform one or more measurement sessions on said one or more portions of the subject's cornea surface and obtain defocused images of secondary speckle pattern responses of each of said one or more portions to coherent illumination during said certain time period of the application of the pressure field, and generating measured image data in the form of a sequence of speckle patterns; and
    a control unit configured for data communication with the measurement unit to receive the measured image data and data indicative of the pressure field, the control unit comprising a processor utility configured to carry out the following:
        translating each of said sequences of the speckle patterns into a time varying spatial correlation function, being a time-varying function of at least one spatial feature of a correlation peak characterizing a spatial correlation function between successive speckle patterns in the sequence and being indicative of the change of the speckle pattern over time;
        analyzing said time varying spatial correlation function to determine, from said change of the speckle pattern over time, motion data indicative of movement of each of said one or more portions of the cornea surface occurring due to the external stimulation by said pressure field of the predetermined profile, and determining the IOP of the subject; and
        generating output data indicative of said determined IOP of the subject.

2. The system according to claim 1, wherein said analyzing of the time varying spatial correlation function to determine the IOP comprises: applying to said time varying spatial correlation function at least one predetermined model comprising model data indicative of a relation between one or more measurable parameters and one or more conditions of a subject including IOP condition, said applying of the at least one predetermined model comprising selecting at least one spatial feature of the time varying spatial correlation function corresponding to a parameter of the pressure field profile, and using said at least one selected spatial feature as the measurable parameter in the model to determine the IOP of the subject.

3. The system according to claim 1, wherein said pressure field comprises an acoustic field.

4. The system according to claim 1, wherein said translating of said sequence of the speckle patterns into the time varying spatial correlation function comprises: determining the spatial correlation function between each two successive speckle patterns, thereby obtaining a sequence of two or more spatial correlation functions each characterized by the correlation peak; and determining the time variation of the at least one spatial feature of the correlation peak between the adjacent speckle patterns, said at least one spatial feature comprising at least one of a position and value of the correlation peak.

5. The system according to claim 1, wherein said selecting and use of the at least one spatial feature of the time varying spatial correlation function corresponding to the parameter of the pressure field profile comprises determining Fourier transform of the time varying spatial correlation function and obtaining a spectrum of said function, and analyzing an amplitude value of the spectrum at a stimulation frequency of the pressure field applied during collection of the image measured data.

6. The system according to claim 1, wherein said selecting and use of the at least one spatial feature of the time varying spatial correlation function corresponding to the parameter of the pressure field profile comprises determining Fourier transform of the time varying spatial correlation function and obtaining a spectrum of said function, and analyzing an amplitude value of the spectrum at a stimulation frequency of the pressure field applied during collection of the image measured data for each of said one or more portions of the cornea surface.

7. The system according to claim 1, wherein the control unit is configured for data communication with a storage device to access data indicative of said at least one predetermined model stored in said storage device.

8. The system according to claim 1, wherein the control unit comprises a memory utility for storing said at least one predetermined model.

9. The system according to claim 1, wherein said imaging device comprises a coherent light source producing illumination of a predetermined number of wavelengths according to a certain sampling time pattern, and a pixel detector array configured and operable to detect the secondary speckle pattern responses of the illuminated portion of the body and generate the measured image data indicative of the detected sequence of the secondary speckle patterns.

10. The system according to claim 1, wherein said pressure field generator comprises an acoustic field source.

11. The system according to claim 1, wherein said processor utility is configured and operable to translate the time varying spatial correlation function into a temporal evolution of the at least one spatial feature of the correlation peak characterizing the spatial correlation function between the successive speckle patterns; and calculating an attribute of the temporal evolution for a predetermined period of time.

12. The system according to claim 11, wherein said model data comprises data indicative of the relation between one or more conditions of a subject including the IOP condition, and one or more measurable parameters including either one or both of the spatial feature of the correlation peak and the attribute of the temporal evolution of said spatial feature.

13. The system according to claim 11, wherein the at least one spatial feature comprises at least one of a position of the correlation peak and an intensity or value of the correlation peak.

14. The system according to claim 11, wherein the attribute comprises at least one of the following: an amplitude of a pulse in the spatial feature, a ratio between positive and negative peak amplitudes in the measured pulse, a period between peaks in the measured pulse, a standard deviation of a background noise, area under various temporal sections within the pulse.

15. The system of claim 1, wherein said processor utility is further configured to apply component analysis to the time varying spatial correlation function in order to characterize and separate between temporal characteristics of the correlation peak for reflections related to different values of the IOP.

16. A measurement system for non-invasive measurement of one or more conditions of a subject's body, said one or more conditions comprising an intra ocular pressure (IOP) of the subject, the system comprising:
a pressure field source configured to generate a pressure field of a predetermined profile and operable to apply said pressure field to one or more portions of a subject's cornea surface during a certain time period;
an imaging device configured and operable to perform one or more measurement sessions on each of the one or more portions of the subject's cornea surface during said certain time period and generating measured image data comprising a sequence of defocused images of secondary speckle pattern responses of each of said one or more portions to coherent illumination during said certain time period; and
a control unit configured as a computer system comprising a processor utility configured and operable to process the measured image data and determine the IOP of the subject, the processor utility being configured to carry out the following:
translating each of the sequences of the speckle patterns of the measured image data into a time varying spatial correlation function, said time varying spatial correlation function being a time-varying function of at least one spatial feature of a spatial correlation function between successive speckle patterns in the sequence and being indicative of the change of the speckle pattern over time;
applying to said time varying spatial correlation function at least one predetermined model to determine an intra-ocular pressure (IOP) of the subject, said at least one predetermined model comprising model data indicative of a relation between one or more measurable parameters and one or more conditions of a subject including IOP condition, said applying of the at least one predetermined model comprising selecting at least one spatial feature of the time varying spatial correlation function corresponding to a parameter of the pressure field profile, and using said at least one selected spatial feature as the measurable parameter to determine the IOP of the subject; and
generating output data indicative of said determined IOP of the subject.

* * * * *